US006808922B1

(12) United States Patent
Bebbington et al.

(10) Patent No.: US 6,808,922 B1

(45) Date of Patent: Oct. 26, 2004

(54) RETROVIRAL VECTORS COMPRISING A FUNCTIONAL SPLICE DONOR SITE AND A FUNCTIONAL SPLICE ACCEPTOR SITE

(75) Inventors: Christopher Robert Bebbington, Berkshire (GB); Susan Mary Kingsman, Oxon (GB); Mark Uden, Oxon (GB); Alan John Kingsman, Oxon (GB); Kyriacos Mitrophanos, Oxon (GB)

(73) Assignee: Oxford Biomedica Limited, Oxford (GB)

( * ) Notice: Subject to any disclaimer, the term of this patent is extended or adjusted under 35 U.S.C. 154(b) by 0 days.

(21) Appl. No.: 09/508,516

(22) PCT Filed: Sep. 23, 1998

(86) PCT No.: PCT/GB98/02867

§ 371 (c)(1),
(2), (4) Date: Jun. 8, 2000

(87) PCT Pub. No.: WO99/15683

PCT Pub. Date: Apr. 1, 1999

(30) Foreign Application Priority Data

Sep. 25, 1997 (GB) ............................................ 9720465

(51) Int. Cl.[7] ........................ C12N 15/63; C12N 15/85; A61K 35/00

(52) U.S. Cl. ................... 435/320.1; 435/325; 424/93.1; 424/93.2; 424/93.21

(58) Field of Search ............................... 424/93.1, 93.2, 424/93.21; 514/44; 435/320.1, 325

(56) References Cited

U.S. PATENT DOCUMENTS 6,544,771 B1 4/2003 Riviere et al.

FOREIGN PATENT DOCUMENTS

| | | | |
|---|---|---|---|
| WO | WO 94/29470 | A1 | 12/1994 |
| WO | 96/28563 | | 9/1996 |
| WO | 98/15636 | | 4/1998 |

OTHER PUBLICATIONS

Ismail et al. Split–intron retroviral vectors: enhanced expression with improved safety vol. 74,No. 5 p. 2365–2371 2000.*

Kriegler et al. Transformation mediated by the SV40 T antigens: separation of the overlapping SV40 early genes with a retroviral vector vol. 38, p. 483–491 Sep. 1984.*

Takeda et al. Construction of chimaeric processed immunoglobulin genes containing mouse variable and human constant region sequences vol. 314 Apr. 1985.*

Lochelt et al. The human foamy virus internal promoter directs the expression of the functional bel 1 transactivator and bet protein early after infection Feb. 1994 p. 638–645.*

(List continued on next page.)

*Primary Examiner*—Michael C. Wilson
(74) *Attorney, Agent, or Firm*—Frommer Laurence & Haug; Thomas J. Kowalski

(57) ABSTRACT

A retroviral vector is described. The retroviral vector comprises a functional splice donor site and a functional splice acceptor site; wherein the functional splice donor site and the functional splice acceptor site flank a first nucleotide sequence of interest ("NOI"); wherein the functional splice donor site is upstream of the functional splice acceptor site; wherein the retroviral vector is derived from a retroviral pro-vector; wherein the retroviral pro-vector comprises a first nucleotide sequence ("NS") capable of yielding the functional splice donor site and a second NS capable of yielding the functional splice acceptor site; wherein the first NS is downstream of the second NS; such that the retroviral vector is formed as a result of reverse transcription of the retroviral pro-vector.

41 Claims, 34 Drawing Sheets

OTHER PUBLICATIONS

Morgenstern, JP and Land, H (1990) Advanced mammalian gene transfer:high titre retroviral vectors with multiple drug selection markers and a complementary helper–free packaging cell line. Nucleic Acids Research 18(12):3587–96.*

Takeda S–I et al (1985) Construction of chimeric processed immunoglobulin genes containing mouse variable and human constant region sequences Nature 314: 452–454.*

Kriegler, M et al (1984) Transformation mediated by the SV40 T antigens: seperation of the overlapping SV40 early genes with a retroviral vector Cell 38:483–91.*

Ismail SI et al (2000) Split–intron retroviral vectors:enhanced expression with improved safety features. Journal of Virology 74(5):2365–2371.*

Verma, IM and Somia N (1997) Gene therapy promises and prospects. Nature 389:239–242.*

Patterson, A (2000) see: http://www4.od.nih.gov/oba/patterson2–00.pdf.*

Eck et al (1996) Gene–Based Therapy in The Pharmaceutical Basis of Therapeutics, 9th ed McGraw Hill.*

Jolly D, (1994)Viral vector systems for gene therapy. Cancer Gene Therapy 1(1):51–54.*

McIvor RS, (1990) Deletion in a recombinant retroviral vector resulting from a cryptic splice donor signal in the MoMLV envelope gene. Virology 176:652–55.*

Zaboikin MM and Scheuning FG, (1998) Poor expression of MDR1 transgene in HeLa cells by bicistronic MoMLV–based vector. Human Gene Therapy, 9:2263–2275.*

Sorrentino et al (1995) Blood 15;86(2):491–501.*

Constance L. Cepko et al., "Construction and Applications of a Highly Transmissible Murine Retrovirus Shuttle Vector.", Cell, vol. 37, pp. 1053–1062, 1984.

Jay P. Morgenstern et al., "Advanced mammalian gene transfer: high titre retroviral vectors with multiple drug selection markers and a complementary helper–free packaging cell line.", Nucleic Acids Research, vol. 18, pp. 3587–3596, 1990.

A. Dusty Miller et al., "Improved Retroviral Vectors for Gene Transfer and Expression.", BioTechniques, vol. 7, No. 9, pp. 980–990, 1989.

Glenn Dranoff et al., "Vaccination with irradiated tumor cells engineered to secrete murine granulocyte–macrophage colony–stimulating factor stimulates potent, specific and long–lasting anti–tumor immunity.", Proceedings of the National Academy of Science, vol. 90, pp. 3539–3543, 1993.

W.J. Krall et al., "Increased levels of spliced RNA account for augmented expression from the MFG retroviral vector in hematopoietic cells.", Gene Therapy, vol. 3, pp. 37–48, 1996.

Frank Lee et al., "Glucocorticoids regulate expression of dihydrofolate reductase cDNA in mouse mammary tumour virus chimaeric plasmids.", Nature, vol. 294, pp. 228–232, 1981.

John A. Lewis, "Structure and Expression of the Chinese Hamster Thymidine Kinase Gene.", Molecular and Cellular Biology, vol. 6, pp. 1998–2010, 1986.

Barbara S. Chapman et al., "Effect of intron A from human cytomegalovirus (Towne) immediate–early gene on heterologous expression in mammalian cells.", Nucleic Acids Research vol. 19, No. 14, pp. 3979–3986, 1991.

Morgenstern J.P., et al, Advanced mammalian gene transfer: high titre retroviral vectors with multiple drug selection markers and a complementary helper–free packaging cell line, *Nucleic Acids Research,* vol. 18, No. 12, pp. 3587–3596, (May 7, 1990).

Bilbao, G., et al, Adenoviral/retroviral vector chimeras: a novel strategy to achieve high–efficiency stable transduction in vivo, *The FASEB Journal,* vol. 11, pp. 624–634, (Jul. 11, 1997).

*Promega Product Catalog,* "Mammalian Expression", pp. 254 and 255, (1997).

Zheng, B, et al., "Increment of hFIX expression with endogenous intron 1 in vitro[1]", *Cell Research,* vol. 7, No. 1, pp. 21–29, (Jun. 1997).

* cited by examiner

Figure 5

GCTAGCTTAAGTAACGCCACTTTGCAAGGCATGGAAAAATACATAACTGAGAATAGAAAAGTTCAGATCAAGGTCAGGAACAAAGAAACAGCTGAATACCAAACAGGATATCTGTGGTAAGCGGTTCCTGCCCC
GGCTCAGGGCCAAGAACAGATGAGACAGCTGAGTGATGGGCCAAACAGGATATCTGTGGTAAGCAGTTCCTGCCCCGGCTCGGGGCCAAGAACAGATGGTCCCCAGATGCGGTCCAGCCCTCAGCAGTTTCTAG
TGAATCATCAGATGTTTCCAGGGTGCCCCAAGGACCTGAAAATGACCCTGTACCTTATTTGAACTAACCAATCAGTTCGCTTCTCGCTTCTGTTCGCGCGCTTCCGCTCTCCGAGCTCAATAAAAGAGCCCACA
ACCCCTCACTCGGCGCGCCAGTCTTCCGATAGACTGCGTCGCCCGGGTACCCGTATTCCCAATAAAGCCTCTTGCTGTTTGCATCCGAATCGTGGTCTCGCTGTTCCTTGGGAGGGTCTCCTCTGAGTGATTGA
CTACCCACGACGGGGGTCTTTCATTTGGGGGCTCGTCCGGGATTTGGAGACCCCTGCCCAGGGACCACCGACCCACCACCGGGAGGCAAGCTGGCCAGCAACTTATCTGTGTCTGTCCGATTGTCTAGTGTCTA
TGTTTGATGTTATGCGCCTGCGTCTGTACTAGTTAGCTAACTAGCTCTGTATCTGGCGGACCCGTGGTGGAACTGACGAGTTCTGAACACCCGGCCGCAACCCTGGGAGACGTCCCAGGGACTTTGGGGGCCGT
TTTTGTGGCCCGACCTGAGGAAGGGAGTCGATGTGGAATCCGACCCCGTCAGGATATGTGGTTCTGGTAGGAGACGAGAACCTAAAACAGTTCCCGCCTCCGTCTGAATTTTTGCTTTCGGTTTGGAACCGAAG
CCGCGCGTCTTGTCTGCTGCAGCGCTGCAGCATCGTTCTGTGTTGTCTCTGTCTGACTGTGTTTCTGTATTTGTCTGAAAATTAGGGCCAGACTGTTACCACTCCCTTAAGTTTGACCTTAGGTCACTGGAAAG
ATGTCGAGCGGATCGCTCACAACCAGTCGGTAGATGTCAAGAAGAGACGTTGGGTTACCTTCTGCTCTGCAGAATGGCCAACCTTTAACGTCGGATGGCCGCGAGACGGCACCTTTAACCGAGACCTCATCACC
CAGGTTAAGATCAAGGTCTTTTCACCTGGCCCGCATGGACACCCAGACCAGGTCCCCTACATCGTGACCTGGGAAGCCTTGGCTTTTGACCCCCCTCCCTGGGTCAAGCCCTTTGTACACCCTAAGCCTCCGCC
TCCTCTTCCTCCATCCGCCCCGTCTCTCCCCCTTGAACCTCCTCGTTCGACCCCGCCTCGATCCTCCCTTTATCCAGCCCTCACTCCTTCTCTAGGCGCCGGAATTCGTTAACTCGAGGATCTAACCTAGGTCT
CGAGTGTTTAAACACTGGGCTTGTCGAGACAGAGAAGACTCTTGCGTTTCTGATAGGCACCTATTGGTCTTACTGACATCCACTTTGCCTTTCTCTCCACAGGTGAGGCCTAGGCTTTTGCAAAAAGCTTGGGC
TGCAGGTCGAGGCGGATCTGATCAAGAGACAGGATGAGGATCGTTTCGCATGATTGAACAAGATGGATTGCACGCAGGTTCTCCGGCCGCTTGGGTGGAGAGGCTATTCGGCTATGACTGGGCACAACAGACAA
TCGGCTGCTCTGATGCCGCCGTGTTCCGGCTGTCAGCGCAGGGGCGCCCGGTTCTTTTTGTCAAGACCGACCTGTCCGGTGCCCTGAATGAACTGCAGGACGAGGCAGCGCGGCTATCGTGGCTGGCCACGACG
GGCGTTCCTTGCGCAGCTGTGCTCGACGTTGTCACTGAAGCGGGAAGGGACTGGCTGCTATTGGGCGAAGTGCCGGGGCAGGATCTCCTGTCATCTCACCTTGCTCCTGCCGAGAAAGTATCCATCATGGCTGA
TGCAATGCGGCGGCTGCATACGCTTGATCCGGCTACCTGCCCATTCGACCACCAAGCGAAACATCGCATCGAGCGAGCACGTACTCGGATGGAAGCCGGTCTTGTCGATCAGGATGATCTGGACGAAGAGCATC
AGGGGCTCGCGCCAGCCGAACTGTTCGCCAGGCTCAAGGCGCGCATGCCCGACGGCGAGGATCTCGTCGTGACCCATGGCGATGCCTGCTTGCCGAATATCATGGTGGAAAATGGCCGCTTTTCTGGATTCATC
GACTGTGGCCGGCTGGGTGTGGCGGACCGCTATCAGGACATAGCGTTGGCTACCCGTGATATTGCTGAAGAGCTTGGCGGCGAATGGGCTGACCGCTTCCTCGTGCTTTACGGTATCGCCGCTCCCGATTCGCA
GCGCATCGCCTTCTATCGCCTTCTTGACGAGTTCTTCTGAGCGGGACTCTGGGGTTCGATAAAATAAAAGATTTTATTTAGTCTCCAGAAAAAGGGGGGAATGAAAGACCCCACCTGTAGGTTTGGCAAGCTAG
CTTAAGTAACGCCATTTTGCAAGGCATGGAAAAATACATAACTGAGAATAGAGAAGTTCAGATCAAGGTCAGGAACAGATGGAACAGCTGAATATGGGCCAAACAGGATATCTGTGGTAAGCAGTTCCTGCCCC
GGCTCAGGGCCAAGAACAGATGGAACAGCTGAATATGGGCCAAACAGGATATCTGTGGTAAGCAGTTCCTGCCCCGGCTCAGGGCCAAGAACAGATGGTCCCCAGATGCGGTCCAGCCCTCAGCAGTTTCTAGA
GAACCATCAGATGTTTCCAGGGTGCCCCAAGGACCTGAAATGACCCTGTGCCTTATTTGAACTAACCAATCAGTTCGCTTCTCGCTTCTGTTCGCGCGCTTCTGCTCCCCGAGCTCAATAAAAGAGCCCACAAC
CCCTCACTCGGGGCGCCGTTAACACTAGTAAGCTTGCTCTAAGGTAAATATGTCGACAGGCCTGCGCCAGTCCTCCGATTGACTGAGTCGCCCGGGTACCCGTGTATCCAATAAACCCTCTTGCAGTTGCATCC
GACTTGTGGTCTCGCTGTTCCTTGGGAGGGTCTCCTCTGAGTGATTGACTACCCGTCAGCGGGGGTCTTTCATTTGGGGGCTCGTCCGGGATCGGGAGACCCCTGCCCAGGGACCACCGACCCACCACCGGGAG
GTAAGCTGGCTGCCTCGCGCGTTTCGGTGATGACGGTGAAAACCTCTGACACATGCAGCTCCCGGAGACGGTCACAGCTTGTCTGTAAGCGGATGCCGGGAGCAGACAAGCCCGTCAGGGCGCGTCAGCGGGTG
TTGGCGGGTGTCGGGGCGCAGCCATGACCCAGTCACGTAGCGATAGCGGAGTGTATACTGGCTTAACTATGCGGCATCAGAGCAGATTGTACTGAGAGTGCACCATATGCGGTGTGAAATACCGCACAGATGCG
TAAGGAGAAAATACCGCATCAGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
CACGACTTATCGCCACTGGCAGCAGCCACTGGTAACAGGATTAGCAGAGCGAGGTATGTAGGCGGTGCTACAGAGTTCTTGAAGTGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATC
CTTTGATCTTTTCTACGGGGTCTGACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAA
AGTATATATGAGTAAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCAACGTTGTTGCCATTGCTGCAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTGAGAATAGTGTATGCGGCGACCGAGTTGCTCTTGCCCGGCGTCAACACGGGATAATACCGCGCCACATA
GCAGAACTTTAAAAGTGCTCATCATTGGAAAACGTTCTTCGGGGCGAAAACTCTCAAGGATCTTACCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAAATGTTGAATACTCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCGCACATTTCCCCGAAAAGTGCCACCTGACGTCTAAGAAACCATTATTATCATGACATTAACCTATAAAAATAGGCGTA
TCACGAGGCCCTTTCGTCTTCAAGAATTCATACCAGATCACCGAAAACTGTCCTCCAAATGTGTCCCCCTCACACTCCCAAATTCGCGGGCTTCTGCCTCTTAGACCACTCTACCCTATTCCCCACACTCACCG
GAGCCAAAGCCGCGGCCCTTCCGTTTCTTTGCTTTTGAAAGACCCCACCCGTAGGTGGCAA

Figure 11A

*pEICUT-LacZ sequence*

TGAATAATAAAATGTGTGTTTGTCCGAAATACGCGTTTTGAGATTTCTGTCGCCGACTAAATTCATGTCGCGCGATAGTGGTGTTTATCGCCGATAGAGATGGCGATATTGGAAAAATTGATATTTGAAAATATGGCATATTGAAA
ATGTCGCCGATGTGAGTTTCTGTGTAACTGATATCGCCATTTTTCCAAAAGTGATTTTTGGGCATACGCGATATCTGGCGATAGCGCTTATATCGTTTACGGGGGATGGCGATAGACGACTTTGGTGACTTGGGCGATTCTGTGTG
TCGCAAATATCGCAGTTTCGATATAGGTGACAGACGATATGAGGCTATATCGCCGATAGAGGCGACATCAAGCTGGCACATGGCCAATGCATATCGATCTATACATTGAATCAATATTGGCCATTAGCCATATTATTCATTGGTTA
TATAGCATAAATCAATATTGGCTATTGGCCATTGCATACGTTGTATCCATATCGTAATATGTACATTTATATTGGCTCATGTCCAACATTACCGCCATGTTGACATTGATTATTGACTAGTTATTAATAGTAATCAATTACGGGGT
CATTAGTTCATAGCCCATATATGGAGTTCCGCGTTACATAACTTACGGTAAATGGCCCGCCTGGCTGACCGCCCAACGACCCCCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGCCAAGTCCGCCCCCTATTGACGTCAATGACGGTAAATGGCCCGCCTGGCATTATGCCCAGTACATGACCTTACGGGACTTTCC
TACTTGGCAGTACATCTACGTATTAGTCATCGCTATTACCATGGTGATGCGGTTTTGGCAGTACACCAATGGGCGTGGATAGCGGTTTGACTCACGGGGATTTCCAAGTCTCCACCCCATTGACGTCAATGGGAGTTTGTTTTGGC
ACCAAAATCAACGGGACTTTCCAAAATGTCGTAACAACTGCGATCGCCCGCCCCGTTGACGCAAATGGGCGGTAGGCGTGTACGGTGGGAGGTCTATATAAGCAGAGCTCGTTTAGTGAACCGGGCACTCAGATTCTGCGGTCTGA
GTCCCTTCTCTGCTGGGCTGAAAAGGCCTTTGTAATAAATATAATTCTCTACTCAGTCCCTGTCTCTAGTTTGTCTGTTCGAGATCCTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTCCTGGCCAGAACACAGGAGGACAGGTAAGATGGGAGACCCTTTGACATGGAGCAAGGCGCTCAAGAAGTTAGAGAAGGTGACGGTAC
AAGGGTCTCAGAAATTAACTACTGGTAACTGTAATTGGGCGCTAAGTCTAGTAGACTTATTTCATGATACCAACTTTGTAAAAGAAAAGGACTCTAGAGTCGACCCCCTCGACGTTTAAACACTGGGCTTGTCGAGACAGAGAAGA
CTCTTGCGTTTCTGATAGGCACCTATTGGTCTTACTGACATCCACTTTGCCTTTCTCTCCACAGGTCACGTGAAGCTAGCCTCGAGGATCTGCGGATCCGGGGAATTCCCCAGTCTCAGGATCCACCATGGGGGATCCCGTCGTTT
TACAACGTCGTGACTGGGAAAACCCTGGCGTTACCCAACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGCGAATGGCGC
TTTGCCTGGTTTCCGGCACCAGAAGCGGTGCCGGAAAGCTGGCTGGAGTGCGATCTTCCTGAGGCCGATACTGTCGTCGTCCCCTCAAACTGGCAGATGCACGGTTACGATGCGCCCATCTACACCAACGTAACCTATCCCATTAC
GGTCAATCCGCCGTTTGTTCCCACGGAGAATCCGACGGGTTGTTACTCGCTCACATTTAATGTTGATGAAAGCTGGCTACAGGAAGGCCAGACGCGAATTATTTTTGATGGCGTTAACTCGGCGTTTCATCTGTGGTGCAACGGGC
GCTGGGTCGGTTACGGCCAGGACAGTCGTTTGCCGTCTGAATTTGACCTGAGCGCATTTTTACGCGCCGGAGAAAACCGCCTCGCGGTGATGGTGCTGCGTTGGAGTGACGGCAGTTATCTGGAAGATCAGGATATGTGGCGGATG
AGCGGCATTTTCCGTGACGTCTCGTTGCTGCATAAACCGACTACACAAATCAGCGATTTCCATGTTGCCACTCGCTTTAATGATGATTTCAGCCGCGCTGTACTGGAGGCTGAAGTTCAGATGTGCGGCGAGTTGCGTGACTACCT
ACGGGTAACAGTTTCTTTATGGCAGGGTGAAACGCAGGTCGCCAGCGGCACCGCGCCTTTCGGCGGTGAAATTATCGATGAGCGTGGTGGTTATGCCGATCGCGTCACACTACGTCTGAACGTCGAAAACCCGAAACTGTGGAGCG
CCGAAATCCCGAATCTCTATCGTGCGGTGGTTGAACTGCACACCGCCGACGGCACGCTGATTGAAGCAGAAGCCTGCGATGTCGGTTTCCGCGAGGTGCGGATTGAAAATGGTCTGCTGCTGCTGAACGGCAAGCCGTTGCTGATT
CGAGGCGTTAACCGTCACGAGCATCATCCTCTGCATGGTCAGGTCATGGATGAGCAGACGATGGTGCAGGATATCCTGCTGATGAAGCAGAACAACTTTAACGCCGTGCGCTGTTCGCATTATCCGAACCATCCGCTGTGGTACAC
GCTGTGCGACCGCTACGGCCTGTATGTGGTGGATGAAGCCAATATTGAAACCCACGGCATGGTGCCAATGAATCGTCTGACCGATGATCCGCGCTGGCTACCGGCGATGAGCGAACGCGTAACGCGAATGGTGCAGCGCGATCGTA
ATCACCCGAGTGTGATCATCTGGTCGCTGGGGAATGAATCAGGCCACGGCGCTAATCACGACGCGCTGTATCGCTGGATCAAATCTGTCGATCCTTCCCGCCCGGTGCAGTATGAAGGCGGCGGAGCCGACACCACGGCCACCGAT
ATTATTTGCCCGATGTACGCGCGCGTGGATGAAGACCAGCCCTTCCCGGCTGTGCCGAAATGGTCCATCAAAAAATGGCTTTCGCTACCTGGAGAGACGCGCCCGCTGATCCTTTGCGAATACGCCCACGCGATGGGTAACAGTCT
TGGCGGTTTCGCTAAATACTGGCAGGCGTTTCGTCAGTATCCCCGTTTACAGGGCGGCTTCGTCTGGGACTGGGTGGATCAGTCGCTGATTAAATATGATGAAAACGGCAACCCGTGGTCGGCTTACGGCGGTGATTTTGGCGATA
CGCCGAACGATCGCCAGTTCTGTATGAACGGTCTGGTCTTTGCCGACCGCACGCCGCATCCAGCGCTGACGGAAGCAAAACACCAGCAGCAGTTTTTCCAGTTCCGTTTATCCGGGCAAACCATCGAAGTGACCAGCGAATACCTG
TTCCGTCATAGCGATAACGAGCTCCTGCACTGGATGGTGGCGCTGGATGGTAAGCCGCTGGCAAGCGGTGAAGTGCCTCTGGATGTCGCTCCACAAGGTAAACAGTTGATTGAACTGCCTGAACTACCGCAGCCGGAGAGCGCCGG
GCAACTCTGGCTCACAGTACGCGTAGTGCAACCGAACGCGACCGCATGGTCAGAAGCCGGGCACATCAGCGCCTGGCAGCAGTGGCGTCTGGCGGAAAACCTCAGTGTGACGCTCCCCGCCGCGTCCCACGCCATCCCGCATCTGA
CCACCAGCGAAATGGATTTTTGCATCGAGCTGGGTAATAAGCGTTGGCAATTTAACCGCCAGTCAGGCTTTCTTTCACAGATGTGGATTGGCGATAAAAAACAACTGCTGACGCCGCTGCGCGATCAGTTCACCCGTGCACCGCTG
GATAACGACATTGGCGTAAGTGAAGCGACCCGCATTGACCCTAACGCCTGGGTCGAACGCTGGAAGGCGGCGGGCCATTACCAGGCCGAAGCAGCGTTGTTGCAGTGCACGGCAGATACACTTGCTGATGCGGTGCTGATTACGAC
CGCTCACGCGTGGCAGCATCAGGGGAAAACCTTATTTATCAGCCGGAAAACCTACCGGATTGATGGTAGTGGTCAAATGGCGATTACCGTTGATGTTGAAGTGGCGAGCGATACACCGCATCCGGCGCGGATTGGCCTGAACTGCC
AGCTGGCGCAGGTAGCAGAGCGGGTAAACTGGCTCGGATTAGGGCCGCAAGAAAACTATCCCGACCGCCTTACTGCCGCCTGTTTTGACCGCTGGGATCTGCCATTGTCAGACATGTATACCCCGTACGTCTTCCCGAGCGAAAAC
GGTCTGCGCTGCGGGACGCGCGAATTGAATTATGGCCCACACCAGTGGCGCGGCGACTTCCAGTTCAACATCAGCCGCTACAGTCAACAGCAACTGATGGAAACCAGCCATCGCCATCTGCTGCACGCGGAAGAAGGCACATGGCT
GAATATCGACGGTTTCCATATGGGGATTGGTGGCGACGACTCCTGGAGCCCGTCAGTATCGGCGGAATTCCAGCTGAGCGCCGGTCGCTACCATTACCAGTTGGTCTGGTGTCAAAAATAATAATAACCGGGCAGGGGGGATCCGC
AGATCCGGCTGTGGAATGTGTGTCAGTTAGGGTGTGGAAAGTCCCCAGGCTCCCCAGCAGGCAGAAGTATGCAAAGCATGCCTGCAGCCCGGGGGATCCACTAGTGTATGTTTAGAAAAACAAGGGGGGAACTGTGGGGTTTTTAT
GAGGGGTTTTATAAATGATTATAAGAGTAAAAAGAAAGTTGCTGATGCTCTCATAACCTTGTATAACCCAAAGGACTAGCTCATGTTGCTAGGCAACTAAACCGCAATAACCGCATTTGTGACGCGAGTTCCCCATTGGTGACGCG
TTTTGAGATTTCTGTCGCCGACTAAATTCATGTCGCGCGATAGTGGTGTTTATCGCCGATAGAGATGGCGATATTGGAAAAATTGATATTTGAAAATATGGCATATTGAAAATGTCGCCGATGTGAGTTTCTGTGTAACTGATATC
GCCATTTTTCCAAAAGTGATTTTTGGGCATACGCGATATCTGGCGATAGCGCTTATATCGTTTACGGGGGATGGCGATAGACGACTTTGGTGACTTGGGCGATTCTGTGTGTCGCCAAATATCGCAGTTTCGATATAGGTGACAGA
CGATATGAGGCTATATCGCCGATAGAGGCGACATCAAGCTGGCACATGGCCAATGCATATCGATCTATACATTGAATCAATATTGGCCATTAGCCATATTATTCATTGGTTATATAGCATAAATCAATATTGGCTATTGGCCATTG
CATACGTTGTATCCATATCGTAATATGTACATTTATATTGGCTCATGTCCAACATTACCGCCATGTTGACATTGATTATTGACTA

Figure 11B

GTTATTAATAGTAATCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACGGTAAACTGCCCACTTGGCAGTACATCAAGTGTATCATATGCCAAGTCCGCCCCCTATTGACGTCAATGACGGTAAATGGCCCGC
CTGGCATTATGCCCAGTACATGACCTTACGGGACTTTCCTACTTGGCAGTACATCTACGTATTAGTCATCGCTATTACCATGGTGATGCGGTTTTGGCAGTACACCAATGGGCGTGGATAGCGGTTTGACTCACGGGGAT
TTCCAAGTCTCCACCCCATTGACGTCAATGGGAGTTTGTTTTGGCACCAAAATCAACGGGACTTTCCAAAATGTCGTAACAACTGCGATCGCCCGCCCCGTTGACGCAAATGGGCGGTAGGCGTGTACGGTGGGAGGTCT
ATATAAGCAGAGCTCGTTTAGTGAACCGACTTAAGTCTTCCTGCAGGGGCTCTAAGGTAAATAGGGCACTCAGATTCTGCGGTCTGAGTCCCTTCTCTGCTGGGCTGAAAAGGCCTTTGTAATAAATATAATTCTCTACT
CAGTCCCTGTCTCTAGTTTGTCTGTTCGAGATCCTACAGTTGGCGCCCGAACAGGGACCTGAGAGGGGCGCAGACCCTACCTGTTGAACCTGGCTGATCGTAGGATCCCCGGCCAGGTGTGGAAAGTCCCCAGGCTCCCC
AGCAGGCAGAAGTATGCAAAGCATGCATCTCAATTAGTCAGCAACCATAGTCCCGCCCCTAACTCCGCCCATCCCGCCCCTAACTCCGCCCAGTTCCGCCCATTCTCCGCCCCATGGCTGACTAATTTTTTTTATTTATG
CAGAGGCCGAGGCCGCCTCGGCCTCTGAGCTATTCCAGAAGTAGTGAGGAGGCTTTTTTGGAGGCCTAGGCTTTTGCAAAAAGCTTGATTCTTCTGACACAACAGTCTCGAACTTAAGGCTAGAGCCACCATGATTGAAC
AAGATGGATTGCACGCAGGTTCTCCGGCCGCTTGGGTGGAGAGGCTATTCGGCTATGACTGGGCACAACAGACAATCGGCTGCTCTGATGCCGCCGTGTTCCGGCTGTCAGCGCAGGGGCGCCCGGTTCTTTTTGTCAAG
ACCGACCTGTCCGGTGCCCTGAATGAACTGCAGGACGAGGCAGCGCGGCTATCGTGGCTGGCCACGACGGGCGTTCCTTGCGCAGCTGTGCTCGACGTTGTCACTGAAGCGGGAAGGGACTGGCTGCTATTGGGCGAAGT
GCCGGGGCAGGATCTCCTGTCATCTCACCTTGCTCCTGCCGAGAAAGTATCCATCATGGCTGATGCAATGCGGCGGCTGCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGGCTCGCGCCAGCCGAACTGTTCGCCAGGCTCAAGGCGCGCATGCCCGACGGCGAGGATCTCGTCGTGACCCATGGCGAT
GCCTGCTTGCCGAATATCATGGTGGAAAATGGCCGCTTTTCTGGATTCATCGACTGTGGCCGGCTGGGTGTGGCGGACCGCTATCAGGACATAGCGTTGGCTACCCGTGATATTGCTGAAGAGCTTGGCGGCGAATGGGC
TGACCGCTTCCTCGTGCTTTACGGTATCGCCGCTCCCGATTCGCAGCGCATCGCCTTCTATCGCCTTCTTGACGAGTTCTTCTGAGCGGGACTCTGGGGTTCGAAATGACCGACCAAGCGACGCCCAACCTGCCATCACG
ATGGCCGCAATAAAATATCTTTATTTTCATTACATCTGTGTGTTGGTTTTTTGTGTGAATCGATAGCGATAAGGATCGATCCGCGTATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGCTTACAGACAAGCTGTGACCGTCTCCGGGAGCTGCATGTGTCAGAGGTTTTCACCGTCATCACCGAAACGCGCGAGACGAAAGG
GCCTCGTGATACGCCTATTTTTATAGGTTAATGTCATGATAATAATGGTTTCTTAGACGTCAGGTGGCACTTTTCGGGGAAATGTGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATGAGTATTCAACATTTCCGTGTCGCCCTTATTCCCTTTTTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAACTGGATCTCAACAGCGGTAAGATCCTTGAGAGTTTTCGCCCCGAAGAACGTTTTCCAATGATGAGCACTTTTAAAGTTCTGCTATGTGGCG
CGGTATTATCCCGTATTGACGCCGGGCAAGAGCAACTCGGTCGCCGCATACACTATTCTCAGAATGACTTGGTTGAGTACTCACCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGC
CATACCAAACGACGAGCGTGACACCACGATGCCTGTAGCAATGGCAACAACGTTGCGCAAACTATTAACTGGCGAACTACTTACTCTAGCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAGTTATCTACACGACGGGG
AGTCAGGCAACTATGGATGAACGAAATAGACAGATCGCTGAGATAGGTGCCTCACTGATTAAGCATTGGTAACTGTCAGACCAAGTTTACTCATATATACTTTAGATTGATTTAAAACTTCATTTTTAATTTAAAAGGAT
CTAGGTGAAGATCCTTTTTGATAATCTCATGACCAAAATCCCTTAACGTGAGTTTTCGTTCCACTGAGCGTCAGACCCCGTAGAAAAGATCAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTGTAGCCGTAGTTAGGCCACCAC
TTCAAGAACTCTGTAGCACCGCCTACATACCTCGCTCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTGTCGGGTTTCGCCACTCTGACTTGAGCGTCGATTTTTGTGATGCTCGTCAGGGGGGCGGAGCCTATGGAAAAACGCCAGCA
ACGCGGCCTTTTTACGGTTCCTGGCCTTTTGCTGGCCTTTTGCTCACATGGCTCGACAGATCT

Figure 15

```
3'end of pol      5'-ATG CGT TCA ACG CTC TCA AAA CCC CTT AAA AAT AAG
5'altered 4070A   5'-ATG GCC AGA AGC ACC CTG AGC AAG CCA CCC CAG GAC

                     GTT AAC CCG CGA GGC CCC CTA ATC CCC-3'
                     AAA AAT CCC TGG AAA CCT CTG ATC GTC-3'
```

Figure 16

ATGGCCAGAA GCACCCTGAG CAAGCCACCC CAGGACAAAA TCAATCCCTG GAAACCTCTG
ATCGTCATGG GAGTCCTGTT AGGAGTAGGG ATGGCAGAGA GCCCCCATC AGGTC
TTTAATGTAA CCTGGAGAGT CACCAACCTG
ATGACTGGGC GTACCGCCAA TGCCACCTCC CTCCTGGGAA CTGTACAAGA TGCCTTCCCA
AAATTATATT TTGATCTATG TGATCTGGTC GGAGAGGAGT GGGACCCTTC AGACCAGGAA
CCGTATGTCG GGTATGGCTG CAAGTACCCC GCAGGGAGAC AGCGGACCCG GACTTTTGAC
TTTTACGTGT GCCCTGGGCA TACCGTAAAG TCGGGGTGTG GGGGACCAGG AGAGGGCTAC
TGTGGTAAAT GGGGGTGTGA AACCACCGGA CAGGCTTACT GGAAGCCCAC ATCATCGTGG
GACCTAATCT CCCTTAAGCG CGGTAACACC CCCTGGGACA CGGGATGCTC TAAAGTTGCC
TGTGGCCCCT GCTACGACCT CTCCAAAGTA TCCAATTCCT TCCAAGGGGC TACTCGAGGG
GGCAGATGCA ACCCTCTAGT CCTAGAATTC ACTGATGCAG GAAAAAAGGC TAACTGGGAC
GGGCCCAAAT CGTGGGGACT GAGACTGTAC CGGACAGGAA CAGATCCTAT TACCATGTTC
TCCCTGACCC GGCAGGTCCT TAATGTGGGA CCCCGAGTCC CCATAGGGCC CAACCCAGTA
TTACCCGACC AAAGACTCCC TTCCTCACCA ATAGAGATTG TACCGGCTCC ACAGCCACCT
AGCCCCCTCA ATACCAGTTA CCCCCCTTCC ACTACCAGTA CACCCTCAAC CTCCCCTACA
AGTCCAAGTG TCCCACAGCC ACCCCCAGGA ACTGGAGATA GACTACTAGC TCTAGTCAAA
GGAGCCTATC AGGCGCTTAA CCTCACCAAT CCCGACAAGA CCCAAGAATG TTGGCTGTGC
TTAGTGTCGG GACCTCCTTA TTACGAAGGA GTAGCGGTCG TGGGCACTTA TACCAATCAT
TCCACCGCTC CGGCCAACTG TACGGCCACT TCCCAACATA AGCTTACCCT ATCTGAAGTG
ACAGGACAGG GCCTATGCAT GGGGGCAGTA CCTAAAACTC ACCAGGCCTT ATGTAACACC
ACCCAAAGCG CCGGCTCAGG ATCCTACTAC CTTGCAGCAC CCGCCGGAAC AATGTGGGCT
TGCAGCACTG GATTGACTCC CTGCTTGTCC ACCACGGTGC TCAATCTAAC CACAGATTAT
TGTGTATTAG TTGAACTCTG GCCCAGAGTA ATTTACCACT CCCCCGATTA TATGTATGGT
CAGCTTGAAC AGCGTACCAA ATATAAAAGA GAGCCAGTAT CATTGACCCT GGCCCTTCTA
CTAGGAGGAT TAACCATGGG AGGGATTGCA GCTGGAATAG GGACGGGGAC CACTGCCTTA
ATTAAAACCC AGCAGTTTGA GCAGCTTCAT GCCGCTATCC AGACAGACCT CAACGAAGTC
GAAAAGTCAA TTACCAACCT AGAAAAGTCA CTGACCTCGT TGTCTGAAGT AGTCCTACAG
AACCGCAGAG GCCTAGATTT GCTATTCCTA AAGGAGGGAG GTCTCTGCGC AGCCCTAAAA
GAAGAATGTT GTTTTTATGC AGACCACACG GGGCTAGTGA GAGACAGCAT GGCCAAATTA
AGAGAAAGGC TTAATCAGAG ACAAAAACTA TTTGAGACAG GCCAAGGATG GTTCGAAGGG
CTGTTTAATA GATCCCCCTG GTTTACCACC TTAATCTCCA CCATCATGGG ACCTCTAATA
GTACTCTTAC TGATCTTACT CTTTGGACCT TGCATTCTCA ATCGATTGGT CCAATTTGTT
AAAGACAGGA TCTCAGTGGT CCAGGCTCTG GTTTTGACTC AGCAATATC CCAGCTAAAA
CCCATAGAGT ACGAGCCATG A

SD = Splice donor
~~SD~~ = non functional splice donor
SA = Splice acceptor
(sa) = cryptic splice acceptor
ψ = packaging site
IRES = internal ribosome entry site (optional)

RETROVIRAL VECTORS COMPRISING A FUNCTIONAL SPLICE DONOR SITE AND A FUNCTIONAL SPLICE ACCEPTOR SITE

The present invention relates to a vector.

In particular, the present invention relates to a novel system for packaging and expressing genetic material in a retroviral particle.

More in particular, the present invention relates to a novel system capable of expressing a retroviral particle that is capable of delivering a nucleotide sequence of interest (hereinafter abbreviated as "NOI")—or even a plurality of NOIs—to one or more target sites.

In addition, the present invention relates to inter alia a novel retroviral vector useful in gene therapy.

BACKGROUND OF THE INVENTION

Gene therapy may include any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology (Ed Robert Meyers, Pub VCH, such as pages 556–558).

By way of further example, gene therapy can also provide a means by which any one or more of: a nucleotide sequence, such as a gene, can be applied to replace or supplement a defective gene; a pathogenic nucleotide sequence, such as a gene, or expression product thereof can be eliminated; a nucleotide sequence, such as a gene, or expression product thereof, can be added or introduced in order, for example, to create a more favourable phenotype; a nucleotide sequence, such as a gene, or expression product thereof can be added or introduced, for example, for selection purposes (i.e. to select transformed cells and the like over non-transformed cells); cells can be manipulated at the molecular level to treat, cure or prevent disease conditions—such as cancer (Schmidt-Wolf and Schmidt-Wolf, 1994, Annals of Hematology 69;273–279) or other disease conditions, such as immune, cardiovascular, neurological, inflammatory or infectious disorders; antigens can be manipulated and/or introduced to elicit an immune response, such as genetic vaccination.

In recent years, retroviruses have been proposed for use in gene therapy. Essentially, retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse so transcriptase enzyme. The DNA copy serves as a template for the production of new RNA genomes and virally encoded proteins necessary for the assembly of infectious viral particles.

There are many retroviruses and examples include: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758–763).

Details on the genomic structure of some retroviruses may be found in the art. By way of example, details on HIV may be found from the NCBI Genbank (i.e. Genome Accession No. AF033819).

Essentially, all wild type retroviruses contain three major coding domains, gag, pol, env, which code for essential virion proteins. Nevertheless, retroviruses may be broadly divided into two categories: namely, "simple" and "complex". These categories are distinguishable by the organisation of their genomes. Simple retroviruses usually carry only elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: S M Coffin, S M Hughes, H E Varmus pp 1–25).

All oncogenic members except the human T-cell leukemia virus-bovine leukemia virus group (HTLV-BLV) are simple retroviruses. HTLV, BLV and the lentiviruses and spumaviruses are complex. Some of the best studied oncogenic retroviruses are Rous sarcoma virus (RSV), mouse mammary tumour virus (MMTV) and murine leukemia virus (MLV) and the human T-cell leukemia virus (HTLV).

The lentivirus group can be split even further into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIR) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053–3058; Lewis and Emerman 1994 J. Virol. 68: 510–516). In contrast, other retroviruses—such as MLV—are unable to infect non-dividing cells such as those that make up, for example, muscle, brain, lung and liver tissue.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called "budding".

As already indicated, each retroviral genome comprises genes called gag, pol and env which code for virion proteins and enzymes. In the provirus, these genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For ease of understanding, simple, generic structures (not to scale) of the RNA and the DNA forms of the retroviral genome are presented below in which the elementary features of the LTRs and the relative positioning of gag, pol and env are indicated.

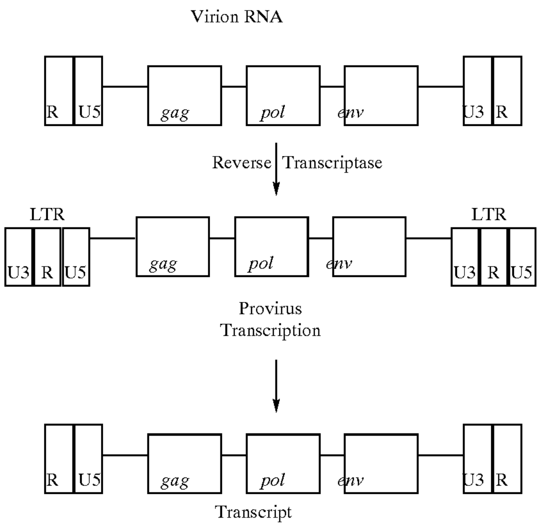

As shown in the diagram above, the basic molecular organisation of an infectious retroviral RNA genome is (5') R—U5—gag, pol, env—U3-R (3'). In a defective retroviral vector genome gag, pol and env may be absent or not functional. The R regions at both ends of the RNA are repeated sequences. U5 and U3 represent unique sequences at the 5' and 3'ends of the RNA genome respectively.

Reverse transcription of the virion RNA into double stranded DNA takes place in the cytoplasm and involves two jumps of the reverse transcriptase from the 5' terminus to the 3'terminus of the template molecule. The result of these jumps is a duplication of sequences located at the 5' and 3'ends of the virion RNA. These sequences then occur fused in tandem on both ends of the viral DNA, forming the long terminal repeats (LTRs) which comprise R U5 and U3 regions. On completion of the reverse transcription, the viral DNA is translocated into the nucleus where the linear copy of the retroviral genome, called a preintegration complex (PIC), is randomly inserted into chromosomal DNA with the aid of the virion integrase to form a stable provirus. The number of possible sites of integration into the host cellular genome is very large and very widely distributed.

The control of proviral transcription remains largely with the noncoding sequences of the viral LTR. The site of transcription initiation is at the boundary between U3 and R in the left hand side LTR (as shown above) and the site of poly (A) addition (termination) is at the boundary between R and U5 in the right hand side LTR (as shown above). U3 contains most of the transcriptional control elements of the provirus, which include the promoter and multiple enhancer sequences responsive to cellular and in some cases, viral transcriptional activator proteins. Some retroviruses have any one or more of the following genes such as tat, rev, tax and rex that code for proteins that are involved in the regulation of gene expression.

Transcription of proviral DNA recreates the full length viral RNA genomic and subgenomic-sized RNA molecules that are generated by RNA processing. Typically, all RNA products serve as templates for the production of viral proteins. The expression of the RNA products is achieved by a combination of RNA transcript splicing and ribosomal framshifting during translation.

RNA splicing is the process by which intervening or “intronic” RNA sequences are removed and the remaining “exonic” sequences are ligated to provide continuous reading frames for translation. The primary transcript of retroviral DNA is modified in several ways and closely resembles a cellular mRNA. However, unlike most cellular mRNAs, in which all introns are efficiently spliced, newly synthesised retroviral RNA must be diverted into two populations. One population remains unspliced to serve as the genomic RNA and the other population is spliced to provide subgenomic RNA.

The full-length unspliced retroviral RNA transcripts serve two functions: (i) they encode the gag and pol gene products and (ii) they are packaged into progeny virion particles as genomic RNA. Sub-genomic-sized RNA molecules provide mRNA for the remainder of the viral gene products. All spliced retroviral transcripts bear the first exon, which spans the U5 region of the 5' LTR. The final exon always retains the U3 and R regions encoded by the 3'LTR although it varies in size. The composition of the remainder of the RNA structure depends on the number of splicing events and the choice of alternative splice sites.

In simple retroviruses, one population of newly synthesised retroviral RNA remains unspliced to serve as the genomic RNA and as mRNA for gag and pol. The other population is spliced, fusing the 5' portion of the genomic RNA to the downstream genes, most commonly env. Splicing is achieved with the use of a splice donor positioned upstream of gag and a splice acceptor near the 3'terminus of pol. The intron between the splice donor and splice acceptor that is removed by splicing contains the gag and pol genes. This splicing event creates the mRNA for envelope (Env) protein.

Typically the splice donor is upstream of gag but in some viruses, such as ASLV, the splice donor is positioned a few codons into the gag gene resulting in a primary Env translation product that includes a few amino-terminal amino acid residues in common with Gag. The Env protein is synthesised on membrane-bound polyribosomes and transported by the cell’s vesicular traffic to the plasma membrane, where it is incorporated into viral particles.

Complex retroviruses generate both singly and multiply spliced transcripts that encode not only the env gene products but also the sets of regulatory and accessory proteins unique to these viruses. Compex retroviruses such as the lentiviruses, and especially HIV, provide striking examples of the complexity of alternative splicing that can occur during retroviral infection. For example, it is now known that HIV-1 is capable of producing over 30 different mRNAs by sub-optimal splicing from primary genomic transcripts. This selection process appears to be regulated as mutations that disrupt competing splice acceptors can cause shifts in the splicing patterns and can affect viral infectivity (Purcell and Martin 1993 J Virol 67: 6365–378).

The relative proportions of full-length RNA and subgenomic-sized RNAs vary in infected cells and modulation of the levels of these transcripts is a potential control step during retroviral gene expression. For retroviral gene expression, both unspliced and spliced RNAs must be transported to the cytoplasm and the proper ratio of spliced and unspliced RNA must be maintained for efficient retroviral gene expression. Different classes of retroviruses have evolved distinct solutions to this problem. The simple retroviruses, which use only full-length and singly spliced RNAs regulate the cytoplasmic ratios of these species either by the use of variably efficient splice sites or by the incorporation of several cis-acting elements, that have been only partially defined, into their genome. The complex retroviruses, which direct the synthesis of both singly and multiply spliced RNA, regulate the transport and possibly splicing of the different genomic and subgenomic-sized RNA species through the interaction of sequences on the RNA with the protein product of one of the accessory genes, such as rev in HIV-1 and rex in HTLV-1.

With regard to the structural genes gag, pol and env themselves and in slightly more detail, gag encodes the internal structural protein of the virus. Gag is proteolytically processed into the mature proteins MA (matrix), CA (capsid) and NC (nucleocapsid). The pol gene encodes the reverse transcriptase (RT), which contains both DNA polymerase, and associated RNase H activities and integrase (IN), which mediates replication of the genome. The env gene encodes the surface (SU) glycoprotein and the transmembrane (TM) protein of the virion, which form a complex that interacts specifically with cellular receptor proteins. This interaction leads ultimately to fusion of the viral membrane with the cell membrane.

The Env protein is a viral protein which coats the viral particle and plays an essential role in permitting viral entry into a target cell. The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesised in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they play an essential role in the entry process. In this regard, the SU domain binds to a receptor molecule, often a specific receptor molecule, on the target cell. It is believed that this binding event activates the membrane fusion-inducing potential of the TM protein after which the viral and cell membranes fuse. In some viruses, notably MLV, a cleavage event, resulting in the removal of a short portion of the cytoplasmic tail of TM, is thought to play a key role in uncovering the full fusion activity of the protein (Brody et al 1994 J Virol 68: 4620–4627; Rein et al 1994 J Virol 68: 1773–1781). This cytoplasmic "tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. Here, transduction includes a process of using a viral vector to deliver a non-viral gene to a target cell. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an Env protein with an erythropoietin segement produced a recombinant retrovirus which then binds specifically to human cells that express the erythropoietin receptor on their surface, such as red blood cell precursors (Maulik and Patel 1997 "Molecular Biotechnology: Therapeutic Applications and Strategies" 1997 Wiley-Liss Inc. pp 45).

In addition to gag, pol and env, the complex retroviruses also contain "accessory" genes which code for accessory or auxiliary proteins. Accessory or auxiliary proteins are defined as those proteins encoded by the accessory genes in addition to those encoded by the usual replicative or structural genes, gag, pol and env. These accessory proteins are distinct from those involved in the regulation of gene expression, like those encoded by tat, rev, tax and rex. Examples of accessory genes include one or more of vif, vpr, vpx, vpu and nef. These accessory genes can be found in, for example, HIV (see, for example pages 802 and 803 of "Retroviruses" Ed. Coffin et al Pub. CSHL 1997). Non-essential accessory proteins may function in specialised cell types, providing functions that are at least in part duplicative of a function provided by a cellular protein. Typically, the accessory genes are located between pot and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral rat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (otherwise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158:1–24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic and/or a diagnostic effect. Thus, the transfer of a NOI into a site of interest is typically achieved by: integrating the NOI into the recombinant viral vector; packaging the modified viral vector into a virion coat; and allowing transduction of a site of interest—such as a targeted cell or a targeted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to transduce cells to introduce the NOI into the genome of the cells. The recombinant virus whose genome lacks all genes required to make viral proteins can tranduce only once and cannot propagate. These viral vectors which are only capable of a single round of transduction of target cells are known as replication defective vectors. Hence, the NOI is introduced into the host/target cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production. More recently, packaging cells have been developed in which the gag, pol and env viral coding regions are carried on separate expression plasmids that are independently transfected into a packaging cell line so that three recombinant events are required for wild type viral production. This reduces the potential for production of a replication-competent virus. This strategy is sometimes referred to as the three plasmid transfection method (Soneoka et al 1995 Nucl. Acids Res. 23: 628–33).

Transient transfection can also be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI. Vector production involves transient transfection of one or more of these components into cells containing the other required components. If the vector encodes toxic genes or genes that interfere with the replication of the host cell, such as inhibitors of the cell cycle or genes that induce apotosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, Proc Natl Acad Sci 90:8392–8396).

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatis virus (VSV). Insertion of the Env protein of VSV facilitates vector concentration as HIV/VSV-G vectors with titres of $5\times10^5$ ($10^8$ after concentration) have been generated by transient transfection (Naldini et al 1996 Science 272: 263–267). Thus, transient transfection of HIV vectors may provide a useful strategy for the generation of high titre vectors (Yee et al 1994 PNAS. 91: 9564–9568).

With regard to vector titre, the practical uses of retroviral vectors have been limited largely by the titres of transducing particles which can be attained in vitro culture (typically not more than $10^8$ particles/ml) and the sensitivity of many enveloped viruses to traditional biochemical and physicochemical techniques for concentrating and purifying viruses.

By way of example, several methods for concentration of retroviral vectors have been developed, including the use of centrifugation (Fekete and Cepko 1993 Mol Cell Biol 13: 2604–2613), hollow fibre filtration (Paul et al 1993 Hum Gene Ther 4: 609–615) and tangential flow filtration (Kotani et al 1994 Hum Gene Ther 5: 19–28). Although a 20-fold increase in viral titre can be achieved, the relative fragility of retroviral Env protein limits the ability to concentrate retroviral vectors and concentrating the virus usually results in a poor recovery of infectious virions. While this problem can be overcome by substitution of the retroviral Env protein with the more stable VSV-G protein, as described above, which allows for more effective vector concentration with better yields, it suffers from the drawback that the VSV-G protein is quite toxic to cells.

Although helper-virus free vector titres of $10^7$ cfu/ml are obtainable with currently available vectors, experiments can often be done with much lower-titre vector stocks. However, for practical reasons, high-titre virus is desirable, especially when a large number of cells must be infected. In addition, high titres are a requirement for transduction of a large percentage of certain cell types. For example, the frequency of human hematopoietic progenitor cell infection is strongly dependent on vector titre, and useful frequencies of infection occur only with very high-titre stocks (Hock and Miller 1986 Nature 320: 275–277; Hogge and Humphries 1987 Blood 69: 611–617). In these cases, it is not sufficient simply to expose the cells to a larger volume of virus to compensate for a low virus titre. On the contrary, in some cases, the concentration of infectious vector virions may be critical to promote efficient transduction.

Workers are trying to create high titre vectors for use in gene delivery. By way of example, a comparison of different vector designs has proved useful in helping to define the essential elements required for high-titre viral production. Early work on different retroviral vector design showed that almost all of the internal protein-encoding regions of MLVs could be deleted without abolishing the infectivity of the vector (Miller et al 1983 Proc Natl Acad Sci 80: 4709–4713). These early vectors retained only a small portion of the 3' end of the env-coding region. Subsequent work has shown that all of the env-gene-coding sequences can be removed without further reduction in vector titre (Miller and Rosman 1989 Biotechnique 7: 980–990; Morgenstern and Land 1990 Nucleic Acids Res 18: 3587–3596). Only the viral LTRs and short regions adjoining the LTRs, including the segments needed for plus- and minus-strand DNA priming and a region required for selective packaging of viral RNA into virions (the psi site; Mann et al 1983 Cell 33: 153–159) were deemed necessary for vector transmission. Nevertheless, viral titres obtained with these early vectors were still about tenfold lower than the parental helper virus titre.

Additional experiments indicated that retention of sequences at the 5' end of the gag gene significantly raised viral vector titres and that this was due to an increase in the packaging efficiency of viral RNA into virions (Armentano et al 1987 J Virol 61: 1647–1650; Bender et al 1987 J Virol 61: 1639–1646; Adam and Miller 1988 J Virol 62: 3802–3806). This effect was not due to viral protein synthesis from the gag region of the vector because disruption of the gag reading frame or mutating the gag codon to a top codon had no effect on vector titre (Bender et at 1987 ibid). These experiments demonstrated that the sequences required for efficient packaging of genomic RNA in MLV were larger than the psi signal previously defined by deletion analysis (Mann et al 1983 ibid). In order to obtain high titres ($10^6$ to $>10^7$), it was shown to be important that this larger, signal, called psi plus, be included in retroviral vectors. It has now been demonstrated that this signal spans from upstream of the splice donor to downstream of the gag start codon (Bender et al 1987 ibid). Because of this position, in spliced env expressing transcripts this signal is deleted. This ensures that only full length transcripts containing all three essential genes for viral life cycle are packaged.

In addition to manipulating the retroviral vector with a view to increasing vector titre, retroviral vectors have also been designed to induce the production of a specific NOI (usually a marker protein) in transduced cells. As already mentioned, the most common retroviral vector design involves the replacement of retroviral sequences with one or more NOIs to create replication-defective vectors. The simplest approach has been to use the promoter in the retroviral 5' LTR to control the expresssion of a cDNA encoding an NOI or to alter the enhancer/promoter of the LTR to provide tissue-specific expression or inducibility. Alternatively, a single coding region has been expressed by using an internal promoter which permits more flexibility in promoter selection.

These strategies for expression of a gene of interest have been most easily implemented when the NOI is a selectable marker, as in the case of hypoxanthine-guanine phosphoribosyl transferase (hprt) (Miller et al 1983 Proc Natl Acad Sci 80: 4709–4713) which facilitates the selection of vector transduced cells. If the vector contains an NOI that is not a selectable marker, the vector can be introduced into packaging cells by co-transfection with a selectable marker present on a separate plasmid. This strategy has an appealing advantage for gene therapy in that a single protein is expressed in the ultimate target cells and possible toxicity or antigenicity of a selectable marker is avoided. However, when the inserted gene is not selectable, this approach has the disadvantage that it is more difficult to generate cells that produce a high titre vector stock. In addition it is usually more difficult to determine the titre of the vector.

The current methodologies used to design retroviral vectors that express two or more proteins have relied on three general strategies. These include: (i) the expression of different proteins from alternatively spliced mRNAs transcribed from one promoter; (ii) the use of the promoter in the 5' LTR and internal promoters to drive transcription of different cDNAs and (iii) the use of internal ribosomal entry site (IRES) elements to allow translation of multiple coding regions from either a single mRNA or from fusion proteins that can then be expressed from an open reading frame.

Vectors containing internal promoters have been widely used to express multiple genes. An internal promoter makes it possible to exploit the promoter/enhancer combinations other than the viral LTR for driving gene expression. Multiple internal promoters can be included in a retroviral vector and it has proved possible to express at least three different cDNAs each from its own promoter (Overell et al 1988 Mol Cell Biol 8: 1803–1808).

While there now exist many such modified retroviral vectors which may be used for the expression of NOIs in a variety of mammalian cells, most of these retroviral vectors are derived from simple retroviruses such as murine oncoretroviruses that are incapable of transducing non-dividing cells.

By way of example, a widely used vector that employs alternative splicing to express genes from the viral LTR SV(X) (Cepko et al 1984 Cell 37: 1053–1062) contains the neomycin phosphotransferase gene as a selectable marker. The model for this type of vector is the parental virus, MO-MLV, in which the Gag and Gag-Pol proteins are translated from the full-length viral mRNA and the Env protein is made from the spliced mRNA. One of the proteins encoded by the vector is translated from the full-length RNA whereas splicing that links the splice donor near the 5' LTR to a splice acceptor just upstream of the second gene produces an RNA from which the second gene product can be translated. One drawback of this strategy is that foreign sequences are inserted into the intron of the spliced gene. This can affect the ratio of spliced to unspliced RNAs or provide alternative splice acceptors that interfere with production of the spliced RNA encoding the second gene product (Korman et al 1987 Proc Natl Acad Sci 84: 2150–2154). Because these effects are unpredictable, they can affect the production of the encoded genes.

Other modified retroviral vectors can be divided into two classes with regards to splicing capabilities.

The first class of modified retroviral vector, typified by the pBABE vectors (Morgenstern et al 1990 Nucleic Acid Research 18: 3587–3596), contain mutations within the splice donor (GT to GC) that inhibit splicing of viral transcripts. Such splicing inhibition is beneficial for two reasons: Firstly, it ensures all viral transcripts contain a packaging signal and thus all can be packaged in the producer cell. Secondly, it prevents potential aberrant splicing between viral splice donors and possible cryptic splice acceptors of inserted genes.

The second class of modified retroviral vector, typified by both N2 (Miller et at 1989 Biotechniques 7: 980–990) and the more recent MFG (Dranoff et al 1993 Proc Natl Acad Sci 19: 3979–3986), contain functional introns. Both of these vectors use the normal splice donor found within the packaging signal. However, their respective splice acceptors (SAs) differ. For N2, the SA is found within the "extended" packaging signal (Bender et al 1987 ibid). For MFG, the natural SA (found within pol, see FIG. 1 thereof) is used. For both these vectors, it has been demonstrated that splicing greatly enhances gene expression in transduced cells (Miller et al 1989 ibid; Krall et al 1996 Gene Therapy 3: 37–48). Such observations support previous findings that, in general, splicing can enhance mRNA translation (Lee et al 1981 Nature 294: 228–232; Lewis et al 1986 Mol Cell Biol 6:

1998–2010; Chapman et al 1991 Nucleic Acids Res 19: 3979–3986). One likely reason for this is that the same machinery involved in transcript splicing may also aid in transcript export from the nucleus.

Unlike the modified retroviral vectors described above, there has been very little work on alternative splicing in the retroviral lentiviral systems which are capable of infecting non-dividing cells (Naldini et al 1996 Science 272: 263–267). To date the only published lentiviral vectors are those derived from HIV-1 (Kim et al 1997 J Virol 72: 811–816) and FIV (Poeschla et al 1998 Nat Med 4: 354–357). These vectors still contain virally derived splice donor and acceptor sequences (Naldini et al 1996 ibid).

Some alternative approaches to developing high titre vectors for gene delivery have included the use of: (i) defective viral vectors such as adenoviruses, adeno-associated virus (AAV), herpes viruses, and pox viruses and (ii) modified retroviral vector designs.

The adenovirus is a double-stranded, linear DNA virus that does not go through an RNA intermediate. There are over 50 different human serotypes of adenovirus divided into 6 subgroups based on the genetic sequence homology. The natural target of adenovirus is the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses are nonenveloped, regular icosohedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

Entry of adenovirus into cells involves a series of distinct events. Attachment of the virus to the cell occurs via an interaction between the viral fibre (37 nm) and the fibre receptors on the cell. This receptor has recently been identified for Ad2/5 serotypes and designated as CAR (Coxsackie and Adeno Receptor, Tomko et al (1997 Proc Natl Acad Sci 94: 3352–2258). Internalisation of the virus into the endosome via the cellular $\alpha v\beta 3$ and $\alpha v\beta 5$ integrins is mediated by and viral RGD sequence in the penton-base capsid protein (Wickham et al., 1993 Cell 73: 309–319). Following Internalisation, the endosome is disrupted by a process known as endosomolysis, an event which is believed to be preferentially promoted by the cellular $\alpha v\beta 5$ integrin (Wickham et al., 1994 J Cell Biol 127: 257–264). In addition, there is recent evidence that the Ad5 fibre knob binds with high affinity to the MHC class 1 $\alpha 2$ domain at the surface of certain cell types including human epithelial and B lymphoblast cells (Hong et al., 1997 EMBO 16; 2294–2306).

Subsequently the virus is translocated to the nucleus where activation of the early regions occurs and is shortly followed by DNA replication and activation of the late regions. Transcription, replication and packaging of the adenoviral DNA requires both host and viral functional protein machinery.

Viral gene expression can be divided into early (E) and late (L) phases. The late phase is defined by the onset of viral DNA replication. Adenovirus structural proteins are generally synthesised during the late phase. Following adenovirus infection, host cellular mRNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events but it entails essentially the synthesis of viral RNAs prior to the onset of DNA replication.

The Schematic diagram below is of the adenovirus genome showing the relative direction and position of early and late gene transcription:

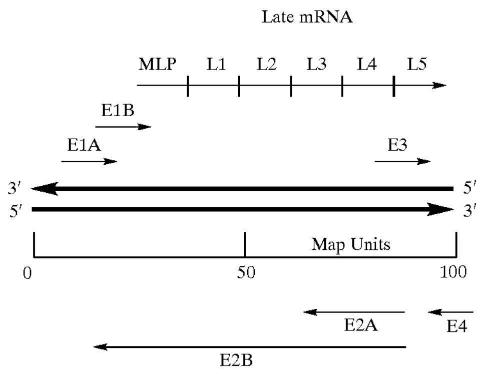

The organisation of the adenovirus genome is similiar in all of the adenovirus groups and specific functions are generally positioned at identical locations for each serotype studied. Early cytoplasmic messenger RNAs are complementary to four defined, noncontiguous regions on the viral DNA. These regions are designated E1-E4. The early transcripts have been classified into an array of intermediate early (E1a), delayed early (E1b, E2a, E2b, E3 and E4), and intermediate regions.

The early genes are expressed about 6–8 hours after infection and are driven from 7 promoters in gene blocks E1–4.

The E1a region is involved in transcriptional transactivation of viral and cellular genes as well as transcriptional repression of other sequences. The E1a gene exerts an important control function on all of the other early adenovirus messenger RNAs. In normal tisssues, in order to transcribe regions E1b, E2a, E2b, E3 or E4 efficiently, active E1a product is required. However, the E1a function may be bypassed. Cells may be manipulated to provide E1a-like functions or may naturally contain such functions. The virus may also be manipulated to bypass the E1a function. The viral packaging signal overlaps with the E1a enhancer (194–358 nt).

The E1b region influences viral and cellular metabolism and host protein shut-off. It also includes the gene encoding the pIX protein (3525–4088 nt) which is required for packaging of the full length viral DNA and is important for the thermostability of the virus. The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection. E1b is required for altering functions of the host cell such that processing and transport are shifted in favour of viral late gene products. These products then result in viral packaging and release of virions. E1b produces a 19 kD protein that prevents apoptosis. E1b also produces a 55 kD protein that binds to p53. For a review on adenoviruses and their replication, see WO 96/17053.

The E2 region is essential as it encodes the 72 kDa DNA binding protein, DNA polymerase and the 80 kDa precurser of the 55 kDa Terminal Protein (TP) needed for protein priming to initiate DNA synthesis.

A 19 kDa protein (gp19K) is encoded within the E3 region and has been implicated in modulating the host immune response to the virus. Expression of this protein is upregulated in response to TNF alpha during the first phase of the infection and this then binds and prevents migration of the MHC class I antigens to the epithelial surface, thereby dampening the recognition of the adenoviral infected cells by the cytotoxic T lymphocytes. The E3 region is dispensible in in vitro studies and can be removed by deletion of a 1.9 kb XbaI fragment.

The E4 region is concerned with decreasing the host protein synthesis and increasing the DNA replication of the virus.

There are 5 families of late genes and all are initiated from the major late promoter. The expression of the late genes includes a very complex post-transcriptional control mechanism involving RNA splicing. The fibre protein is encoded within the L5 region. The adenoviral genome is flanked by the inverted terminal repeat which in Ad5 is 103 bp and is essential for DNA replication. 30–40 hours post infection viral production is complete.

Adenoviruses may be converted for use as vectors for gene transfer by deleting the E1 gene, which is important for the induction of the E2, E3 and E4 promoters. The E1-replication defective virus may be propagated in a cell line that provides the E1 polypeptides in trans, such as the human embryonic kidney cell line 293. A therapeutic gene or genes can be inserted by recombination in place of the E1 gene, Expression of the gene is driven from either the E 1 promoter or a heterologous promoter.

Even more attenuated adenoviral vectors have been developed by deleting some or all of the E4 open reading frames (ORFs). However, certain second generation vectors appear not to give longer-tern gene expression, even though the DNA seems to be maintained. Thus, it appears that the function of one or more of the E4 ORFs may be to enhance gene expression from at least certain viral promoters carried by the virus.

An alternative approach to making a more defective virus has been to "gut" the virus completely maintaining only the terminal repeats required for viral replication. The "gutted" or "gutless" viruses can be grown to high titres with a first generation helper virus in the 293 cell line but it has been difficult to separate the "gutted" vector from the helper virus.

Replication-competent adenoviruses can also be used for gene therapy. For example, the E1A gene can be inserted into a first generation virus under the regulation of a tumour-specific promoter. In thoery, following injection of the virus into a tumour, it could replicated specifically in the tumour but not in the surrounding normal cells. This type of vector could be used either to kill tumour cells directly by lysis or to deliver a "suicide gene" such as the herpes-simplex-virus thymidine-kinase gene (HSV tk) which can kill infected and bystander cells following treatment with ganciclovir. Alternatively, an adenovirus defective only for E1b has been used specifically for antitumour treatment in phase-1 clinical trials. The polypeptides encoded by E1b are able to block p53-mediated apoptosis, preventing the cell from killing itself in response to viral infection. Thus, in normal nontumour cells, in the absence of E1b, the virus is unable to block apoptosis and is thus unable to produce infectious virus and spread. In tumour cells deficient in p53, the E1b defective virus can grow and spread to adjacent p53-defective tumour cells but not to normal cells. Again, this type of vector could also be used to deliver a therapeutic gene such as HSV tk.

The adenovirus provides advantages as a vector for gene delivery over other gene therapy vector systems for the following reasons:

It is a double stranded DNA nonenveloped virus that is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cess and post-mitotically terminally differentiated cells such as neurons (with perhaps the important exception of some lymphoid cells including monocytes).

Adenoviral vectors are also capable of transducing non dividing cells. This is very important for diseases, such as cystic fibrosis, in which the affected cells in the lung epithelium, have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kilobase) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, it functions episomally (independently from the host genome) as a linear genome in the host nucleus. Hence the use of recombinant adenovirus alleviates the problems associated with random integration into the host genome.

There is no association of human malignancy with adenovirus infection. Attenuated adenoviral strains have been developed and have been used in humans as live vaccines.

However, current adenoviral vectors suffer from some major limitations for in vivo therapeutic use. These include: (i) transient gene expression- the adenoviral vector generally remains episomal and does not replicate so that it is not passed onto subsequent progeny (ii) because of its inability to replicate, target cell proliferation can lead to dilution of the vector (iii) an immunological response raised against the adenoviral proteins so that cells expressing adenoviral proteins, even at a low level, are destroyed and (iv) an inability to achieve an effective therapeutic index since in vivo delivery leads to an uptake of the vector and expression of the delivered genes in only a proportion of target cells.

If the features of adenoviruses can be combined with the genetic stability of retro/lentiviruses then essentially the adenovirus can be used to transduce target cells to become transient retroviral producer cells that can stably infect neighbouring cells.

SUMMARY OF THE INVENTION

The present invention seeks to provide a novel retroviral vector.

In particular, the present invention seeks to provide a novel retroviral vector capable of providing efficient expression of a NOI—or even a plurality of NOIs—at one or more desired target sites.

The present invention also seeks to provide a novel system for preparing high titres of vector virion which incorporates safety features for in vivo use and which is capable of providing efficient expression of a NOI—or even a plurality of NOIs—at one or more desired target sites.

According to a first aspect of the present invention, there is provided a retroviral vector comprising a functional splice donor site and a functional splice acceptor site; wherein the functional splice donor site and the functional splice acceptor site flank a first nucleotide sequence of interest ("NOI"); wherein the functional splice donor site is upstream of the functional splice acceptor site; wherein the retroviral vector is derived from a retroviral pro-vector; wherein the retroviral pro-vector comprises a first nucleotide sequence (NS) capable of yielding the functional splice donor site and a second NS capable of yielding the functional splice acceptor site; wherein the first NS is downstream of the second NS; such that the retroviral vector is formed as a result of reverse transcription of the retroviral pro-vector.

According to a second aspect of the present invention, there is provided a retroviral vector wherein the retroviral pro-vector comprises a retroviral packaging signal; and wherein the second NS is located downstream of the retroviral packaging signal such that splicing is preventable at a primary target site.

According to a third aspect of the present invention, there is provided a retroviral vector wherein the second NS is placed downstream of the first NOI such that the first NOI is capable of being expressed at a primary target site.

According to a fourth aspect of the present invention, there is provided a retroviral vector wherein the second NS is placed upstream of a multiple cloning site such that one or more additional NOIs may be inserted.

According to a fifth aspect of the present invention, there is provided a retroviral vector wherein the second NS is a nucleotide sequence coding for an immunological molecule or a part thereof.

According to a sixth aspect of the present invention, there is provided a retroviral vector wherein the immunological molecule is an immunoglobulin.

According to a seventh aspect of the present invention, there is provided a retroviral vector wherein the second NS is a nucleotide sequence coding for an immunoglobulin heavy chain variable region.

According to a eight aspect of the present invention, there is provided a retroviral vector wherein the vector additionally comprises a functional intron.

According to a ninth aspect of the present invention, there is provided a retroviral vector wherein the functional intron is positioned so that it is capable of restricting expression of at least one of the NOIs in a desired target site.

According to a tenth aspect of the present invention, there is provided a retroviral vector wherein the target site is a cell.

According to a eleventh aspect of the present invention, there is provided a retroviral vector wherein the vector or pro-vector is derivable from a murine oncoretrovirus or a lentivirus.

According to a twelfth aspect of the present invention, there is provided a retroviral vector wherein the vector is derivable from MMLV, MSV, MMTV, HIV-1 or EIAV.

According to a thirteenth aspect of the present invention, there is provided a retroviral vector wherein the retroviral vector is an integrated provirus.

According to a fourteenth aspect of the present invention, there is provided a retroviral particle obtainable from a retroviral vector.

According to a fifteenth aspect of the present invention, there is provided a cell transfected or transduced with a retroviral vector.

According to a sixteenth aspect of the present invention there is provided a retroviral vector or a viral particle or a cell for use in medicine.

According to a seventeenth aspect of the present invention there is provided a retroviral vector or a viral particle or a cell for the manufacture of a pharmaceutical composition to deliver one or more NOIs to a target site in need of same.

According to a eighteenth aspect of the present invention there is provided a method comprising transfecting or transducing a cell with a retroviral vector or a viral particle or by use of a cell.

According to a nineteenth aspect of the present invention there is provided a delivery system for a retroviral vector or a viral particle or a cell wherein the delivery system comprises one or more non-retroviral expression vector(s), adenoviruse(s), or plasmid(s) or combinations thereof for delivery of an NOI or a plurality of NOIs to a first target cell and a retroviral vector for delivery of an NOI or a plurality of NOIs to a second target cell.

According to a twentieth aspect of the present invention there is provided a retroviral pro-vector.

According to a twenty first aspect of the present invention there is provided the use of a functional intron to restrict expression of one or more NOIs within a desired target cell.

According to a twenty second aspect of the present invention there is provided the use of a reverse transcriptase to deliver a first NS from the 3' end of a retroviral pro-vector to the 5' end of a retroviral vector.

According to a twenty third aspect of the present invention there is provided a hybrid viral vector system for in vivo gene delivery, which system comprises one or more primary viral vectors which encode a secondary viral vector, the primary vector or vectors capable of infecting a first target cell and of expressing therein the secondary viral vector, which secondary vector is capable of transducing a secondary target cell.

According to a twenty fourth aspect of the present invention there is provided a hybrid viral vector system wherein the primary vector is obtainable from or is based on a adenoviral vector and/or the secondary viral vector is obtainable from or is based on a retroviral vector preferably a lentiviral vector.

According to a twenty fifth aspect of the present invention there is provided a hybrid viral vector system wherein the lentiviral vector comprises or is capable of delivering a split-intron configuration.

According to a twenty sixth aspect of the present invention there is provided a lentiviral vector system wherein the lentiviral vector comprises or is capable of delivering a split-intron configuration.

According to a twenty seventh aspect of the present invention there is provided an adenoviral vector system wherein the adenoviral vector comprises or is capable of delivering a split-intron configuration.

According to a twenty eighth aspect of the present invention there is provided vectors or plasmids basd on or obtained from any one or more of the entities presented as pE1sp1A, pCI-Neo, pE1RevE, pE1HORSE3.1, pE1PEGASUS4, pCI-Rab, pE1Rab.

According to a twenty ninth aspect of the present invention there is provided a retroviral vector capable of differential expression of NOIs in target cells.

Another aspect of the present invention includes a hybrid viral vector system for in vivo gene delivery, which system comprises a primary viral vector which encodes a secondary viral vector, the primary vector capable of infecting a first target cell and of expressing therein the secondary viral vector, which secondary vector is capable of transducing a secondary target cell, wherein the primary vector is obtainable from or is based on a adenoviral vector and the secondary viral vector is obtainable from or is based on a retroviral vector preferably a lentiviral vector.

Another aspect of the present invention includes a hybrid viral vector system for in vivo gene delivery, which system comprises a primary viral vector which encodes a secondary viral vector, the primary vector capable of infecting a first target cell and of expressing therein the secondary viral vector, which secondary vector is capable of transducing a secondary target cell, wherein the primary vector is obtainable from or is based on a adenoviral vector and the secondary viral vector is obtainable from or is based on a retroviral vector preferably a lentiviral vector; wherein the viral vector system comprises a functional splice donor site and a functional splice acceptor site; wherein the functional splice donor site and the functional splice acceptor site flank a first nucleotide sequence of interest ("NOI"); wherein the functional splice donor site is upstream of the functional splice acceptor site; wherein the retroviral vector is derived from a retroviral pro-vector; wherein the retroviral pro-vector comprises a first nucleotide sequence ("NS") capable of yielding the functional splice donor site and a second NS capable of yielding the functional splice acceptor site; wherein the first NS is downstream of the second NS; such that the retroviral vector is formed as a result of reverse transcription of the retroviral pro-vector.

Preferably the retroviral pro-vector comprises a third NS that is upstream of the second nucleotide sequence; wherein the third NS is capable of yielding a non-functional splice donor site.

Preferably the retroviral vector further comprises a second NOI; wherein the second NOI is downstream of the functional splice acceptor site.

Preferably the retroviral pro-vector comprises the second NOI; wherein the second NOI is downstream of the second nucleotide sequence.

Preferably the second NOI, or the expression product thereof, is or comprises a therapeutic agent or a diagnostic agent.

Preferably the first NOI, or the expression product thereof, is or comprises any one or more of an agent conferring selectablity (e.g. a marker element), a viral essential element, or a part thereof, or combinations thereof.

Preferably the first NS is at or near to the 3' end of a retroviral pro-vector; preferably wherein the 3' end comprises a U3 region and an R region; and preferably wherein the first NS is located between the U3 region and the R region.

Preferably the U3 region and/or the first NS of the retroviral pro-vector comprises an NS that is a third NOI; wherein the NOI is any one or more of a transcriptional control element, a coding sequence or a part thereof.

Preferably the first NS is obtainable from a virus.

Preferably the first NS is an intron or a part thereof.

Preferably the intron is obtainable from the small t-intron of SV40 virus.

Preferably the vector components are regulated. In one preferred aspect of the invention, the vector components are regulated by hypoxia.

In another preferred aspect of the invention, the vector components are regulated by tetracycline on/off system.

Thus, the present invention provides a delivery system which utilises a retroviral vector.

DETAILED DESCRIPTION

The retroviral vector of the delivery system of the present invention comprises a functional splice donor site ("FSDS") and a functional splice acceptor site ("FSAS") which flank a first NOI. The retroviral vector is formed as a result of reverse transcription of a retroviral pro-vector which may comprise a plurality of NOIs.

When the FSDS is positioned upstream of the FSAS, any intervening sequence(s) are capable of being spliced. Typically, splicing removes intervening or "intronic" RNA sequences and the remaining "exonic" sequences are ligated to provide continuous sequences for translation.

The splicing process can be pictorially represented as:

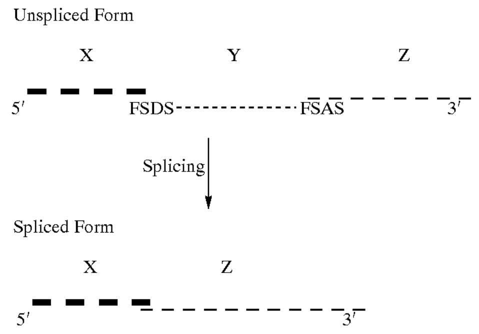

In this pictorial representation, Y represents the intervening sequence that is removed as a result of splicing.

The natural splicing configuration for retroviral vectors is shown in FIG. 27*a*. The splicing configuration of known vectors is shown in FIG. 27*b*. The Splicing configuration according to the present invention is shown in FIG. 27*c*.

In accordance with the present invention, if the FSDS is downstream of the FSAS, then splicing cannot occur.

Likewise, if the FSDS is a non-functional splice donor site (NFSDS) and/or the FSAS is a non-functional acceptor site (NFAS), then splicing cannot occur.

An example of a NFSDS is a mutated FSDS such that the FSDS can no longer be recognised by the splicing mechanism.

In accordance with the present invention, each NS can be any suitable nucleotide sequence. For example, each sequence can be independently DNA or RNA—which may be synthetically prepared or may be prepared by use of recombinant DNA techniques or may be isolated from natural sources or may be combinations thereof. The sequence may be a sense sequence or an antisense sequence. There may be a plurality of sequences, which may be directly or indirectly joined to each other, or combinations thereof.

In accordance with the present invention, each NOI can be any suitable nucleotide sequence. For example, each sequence can be independently DNA or RNA—which may be synthetically prepared or may be prepared by use of recombinant DNA techniques or may be isolated from natural sources or may be combinations thereof. The sequence may be a sense sequence or an antisense sequence. There may be a plurality of sequences, which may be directly or indirectly joined to each other, or combinations thereof.

The first NOI may include any one or more of the following selectable markers which have been used successfully in retroviral vectors: the bacterial neomycin and hygromycin phosphotransferase genes which confer resistance to G418 and hygromycin respectively (Palmer et al 1987 Proc Natl Acad Sci 84: 1055–1059; Yang et al 1987 Mol Cell Biol 7: 3923–3928); a mutant mouse dihydrofolate reductase gene (dhfr) which confers resistance to methotrexate (Miller et al 1985 Mol Cell Biol 5: 431437); the bacterial gpt gene which allows cells to grow in medium containing mycophenolic acid, xanthine and aminopterin (Mann et al 1983 Cell 33: 153–159); the bacterial hisD gene which allows cells to grow in medium without histidine but containing histidinol (Danos and Mulligan 1988 Proc Natl Acad Sci 85: 6460–6464); the multidrug resistance gene (mdr) which confers resistance to a variety of drugs (Guild et al 1988 Proc Natl Acad Sci 85: 1595–1599; Pastan et al 1988 Proc. Natl Acad Sci 85: 4486–4490) and the bacterial genes which confer resistance to puromycin or phleomycin (Morgenstern and Land 1990 Nucleic Acid Res 18: 3587–3596).

All of these markers are dominant selectable markers and allow chemical selection of most cells expressing these genes. β-galactosidase can also be considered a dominant marker; cells expressing β-galactosidase can be selected by using the fluorescence-activated cell sorter. In fact, any cell surface protein can provide a selectable marker for cells not already making the protein. Cells expressing the protein can be selected by using the fluorescent antibody to the protein and a cell sorter. Other selectable markers that have been included in vectors include the hprt and HSV thymidine kinase which allows cells to crow in medium containing hypoxanthine, amethopterin and thymidine.

The first NOI could contain non-coding sequences, for example the retroviral packaging site or non-sense sequences that render the second NOI non-functional in the provector but when they are removed by the splicing the vector the second NOI is revealed for functional expression.

The first NOI may also encode a viral essential element such as env encoding the Env protein which can reduce the complexity of production systems. By way of example, in an adenoviral vector, this allows the retroviral vector genome and the envelope to be configured in a single adenoviral vector under the same promoter control thus providing a simpler system and leaving more capacity in the adenoviral vector for additional sequences. In one aspect, those additional sequences could be the gag-pol cassette itself. Thus in one adenoviral vector one can produce a retroviral vector particle. Previous studies (Feng et al 1997 Nature Biotechnology 15: 866) have required the use of multiple adenoviral vectors.

If the retroviral component includes an env nucleotide sequence, then all or part of that sequence can be optionally replaced with all or part of another env nucleotide sequence such as, by way of example, the amphotropic Env protein designated 4070A or the influenza haemagglutinin (HA) or the vesicular stomatitis virus G (VSV-G) protein. Replacement of the env gene with a heterologous env gene is an example of a technique or strategy called pseudotyping. Pseudotyping is not a new phenomenon and examples may be found in WO-A-98/05759, WO-A-98105754, WO-A-97/17457, WO-A-96109400, WO-A-91/00047 and Mebatsion et al 1997 Cell 90, 841–847.

In one preferred aspect, the retroviral vector of the present invention has been pseudotype. In this regard, pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389:239–242). By way of example, workers have pseudotyped an HIV based vector with the glycoprotein from VSV (Verma and Somia 1997 ibid).

In another alternative, the Env protein may be a modified Env protein such as a mutant or engineered Env protein. Modifications may be made or selected to introduce targeting ability or to reduce toxicity or for another purpose (Valsesia-Wittman et al 1996 J Virol 70: 2056–64; Nilson et al 1996 Gene Therapy 3: 280–6; Fielding et al 1998 Blood 9:1802 and references cited therein).

Suitable second NOI coding sequences include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives therof (such as with an associated reporter group). When included, such coding sequences may be typically operatively linked to a suitable promoter, which may be a promoter driving expression of a ribozyme(s), or a different promoter or promoters.

The second NOI coding sequence may encode a fusion protein or a segment of a coding sequence The retroviral vector of the present invention may be used to deliver a second NOI such as a pro drug activating enzyme to a tumour site for the treatment of a cancer. In each case, a suitable pro-drug is used in the treatment of the individual (such as a patient) in combination with the appropriate pro-drug activating enzyme. An appropriate pro-drug is administered in conjunction with the vector. Examples of pro-drugs include: etoposide phosphate (with alkaline phosphatase, Senter et al 1988 Proc Natl Acad Sci 85: 48424846); 5-fluorocytosine (with cytosine deaminase, Mullen et al 1994 Cancer Res 54: 1503–1506); Doxorubicin-N-p-hydroxyphenoxyacetamide (with Penicillin-V-Amidase, Kerr et al 1990 Cancer Immunol Immunother 31: 202–206); Para-N-bis(2-chloroethyl) aminobenzoyl glutamate (with carboxypeptidase G2); Cephalosporin nitrogen mustard carbamates (with β-lactanase); SRP4233 (with P450 Reducase); Ganciclovir (with HSV thymidine kinase, Borrelli et al 1988 Proc Natl Acad Sci 85: 7572–7576); mustard pro-drugs with nitroreductase (Friedlos et al 1997 J Med Chem 40: 1270–1275) and Cyclophosphamide (with P450 Chen et at 1996 Cancer Res 56: 1331–1340).

The vector of the present invention may be a delivered to a target site by a viral or a non-viral vector.

As it is well known in the art, a vector is a tool that allows or faciliates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Non-viral delivery systems include but are not limited to DNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems, which include but are not limited to DNA transfection methods such as electroporation, DNA biolistics, lipid-mediated transfection, compacted DNA-mediated transfection.

The vector delivery system of the present invention may consist of a primary vector manufactured in vitro which encodes the genes necessary to produce a secondary vector in vivo.

The primary viral vector or vectors may be a variety of different viral vectors, such as retroviral, adenoviral, herpes virus or pox virus vectors, or in the case of multiple primary viral vectors, they may be a mixture of vectors of different viral origin. In whichever case, the primary viral vectors are preferably defective in that they are incapable of independent replication. Thus, they are capable of entering a target cell and delivering the secondary vector sequences, but not of replicating so as to go on to infect further target cells.

In the case where the hybrid viral vector system comprises more than one primary vector to encode the secondary vector, both or all three primary vectors will be used to transfect or transduce a primary target cell population, usually simultaneously.

Preferably, there is a single primary viral vector which encodes all components of the secondary viral vector.

The preferred single or multiple primary viral vectors are adenoviral vectors.

Adenoviral vectors for use in the invention may be derived from a human adenovirus or an adenovirus which does not normally infect humans. Preferably the vectors are derived from adenovirus type 2 or adenovirus type 5 (Ad2 or Ad5) or a mouse adenovirus or an avian adenovirus such as CELO virus (Cotton et al 1993 J Virol 67:3777–3785). The vectors may be replication competent adenoviral vectors but are more preferably defective adenoviral vectors.

Adenoviral vectors may be rendered defective by deletion of one or more components necessary for replication of the virus. Typically, each adenoviral vector contains at least a deletion in the E1 region. For production of infectious adenoviral vector particles, this deletion may be complemented by passage of the virus in a human embryo fibroblast cell line such as human 293 cell line, containing an integrated copy of the left portion of Ad5, including the E1 gene. The capacity for insertion of heterologous DNA into such vectors can be up to approximately 7 kb. Thus such vectors are useful for construction of a system according to the invention comprising three separate recombinant vectors each containing one of the essential transcription units for construction of the retroviral secondary vector.

Alternative adenoviral vectors are known in the art which contain further deletions in other adenoviral genes and these vectors are also suitable for use in the invention. Several of these second generation adenoviral vectors show reduced immunogenicity (eg E1+E2 deletions Gorziglia et al 1996 J Virol 70: 4173–4178; E1+E4 deletions Yeh et al 1996 J Virol 70: 559–565). Extended deletions serve to provide additional cloning capacity for the introduction of multiple genes in the vector. For example a 25 kb deletion has been described (Lieber et al 1996 3 Virol 70: 8944–8960) and a cloning vector deleted of all viral genes has been reported (Fisher et al 1996 Virolology 217: 11–22) which permit the introduction of more than 35 kb of heterologous DNA. Such vectors may be used to generate an adenoviral primary vector according to the invention encoding two or three transcription units for construction of the retroviral secondary vector.

The secondary viral vector is preferably a retroviral vector. The secondary vector is produced by expression of essential genes for assembly and packaging of a defective viral vector particle, within the primary target cells. It is defective in that it is incapable of independent replication. Thus, once the secondary retroviral vector has transduced a secondary target cell, it is incapable of spreading by replication to any further target cells.

The tern "retroviral vector" typically includes a retroviral nucleic acid which is capable of infection, but which is not capable, by itself, of replication. Thus it is replication defective. A retroviral vector typically comprises one or more NOI(s), preferably of non-retroviral origin, for delivery to target cells. A retroviral vector may also comprises a functional splice donor site (FSDS) and a functional splice acceptor site (FSAS) so that when the FSDS is upstream of the FSAS, any intervening sequence(s) are capable of being spliced. A retroviral vector may comprise further non-retroviral sequences, such as non-retroviral control sequences in the U3 region which may influence expression of an NOI(s) once the retroviral vector is integrated as a provirus into a target cell. The retroviral vector need not contain elements from only a single retrovirus. Thus, in accordance with the present invention, it is possible to have elements derivable from two of more different retroviruses or other sources The term "retroviral pro-vector" typically includes a retroviral vector genome as described above but which comprises a first nucleotide sequence (NS) capable of yielding a functional splice donor site (FSDs) and a second NS capable of yielding a functional splice acceptor site (FSAS) such that the first NS is downstream of the second NS so that splicing associated with the first NS and the second NS cannot occur. Upon reverse transcription of the retroviral pro-vector, a retroviral vector is formed.

The term "retroviral vector particle" refers to the packaged retroviral vector, that is preferably capable of binding to and entering target cells. The components of the particle, as already discussed for the vector, may be modified with respect to the wild type retrovirus. For example, the Env proteins in the proteinaceous coat of the particle may be genetically modified in order to alter their targeting specificity or achieve some other desired function.

The retroviral vector of this aspect of the invention may be derivable from a murine oncoretrovirus such as MMLV, MSV or MMTV; or may be derivable from a lentivirus such as HIV-1, EIAV; or may be derivable from another retrovirus.

The retroviral vector of the invention can be modified to render the natural splice donor site of the retrovirus non-functional.

The term "modification" includes the silencing or removal of the natural splice donor. Vectors, such as MLV based vectors, which have the splice donor site removed are known in the art. An example of such a vector is pBABE (Morgenstern et al 1990 ibid).

The secondary vector may be produced from expression of essential genes for retroviral vector production encoded in the DNA of the primary vector. Such genes may include a gag-pol gene from a retrovirus, an env gene from an enveloped virus and a defective retroviral vector containing one or more therapeutic or diagnostic NOI(s). The defective retroviral vector contains in general terms sequences to enable reverse transcription, at least part of a 5' long terminal repeat (LTR), at least part of a 3'LTR and a packaging signal.

If it is desired to render the secondary vector replication defective, that secondary vector may be encoded by a plurality of transcription units, which may be located in a single or in two or more adenoviral or other primary vectors. Thus, there may be a transcription unit encoding the secondary vector genome, a transcription unit encoding gag-pol and a transcription unit encoding env. Alternatively, two or more of these may be combined. For example, nucleic acid sequences encoding gag-pol and env, or env and the genome, may be combined in a single transcription unit. Ways of achieving this are known in the art.

Transcription units as described herein are regions of nucleic acid containing coding sequences and the signals for achieving expression of those coding sequences independently of any other coding sequences. Thus, each transcription unit generally comprises at least a promoter, an enhancer and a polyadenylation signal.

The term "promoter" is used in the normal sense of the art, e.g. an RNA polymerase binding site in the Jacob-Monod theory of gene expression.

The term "enhancer" includes a DNA sequence which binds to other protein components of the transcription initiation complex and thus facilitates the initiation of transcription directed by its associated promoter.

The promoter and enhancer of the transcription units encoding the secondary vector are preferably strongly active, or capable of being strongly induced, in the primary target cells under conditions for production of the secondary viral vector. The promoter and/or enhancer may be constitutively efficient, or may be tissue or temporally restricted in their activity. Examples of suitable tissue restricted promoters/enhancers are those which are highly active in tumour cells such as a promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. One preferred promoter-enhancer combination is a human cytomegalovirus (hCMV) major immediate early (MIE) promoter/enhancer combination.

Other preferred additional components include entities enabling efficient expression of an NOI or a plurality of NOIs.

In one preferred aspect of the present invention, there is hypoxia or ischaemia regulatable expression of the secondary vector components. In this regard, hypoxia is a powerful regulator of gene expression in a wide range of different cell types and acts by the induction of the activity of hypoxia-inducible transcription factors such as hypoxia inducible factor-1 (HIF-1; Wang & Semenza 1993 Proc Natl Acad Sci 90:430), which bind to cognate DNA recognition sites, the hypoxia-responsive elements (HREs) on various gene promoters. Dachs et al (1997 Nature Med 5: 515) have used a multimeric form of the HRE from the mouse phosphoglycerate kinase-1 (PGK-1) gene (Firth et al 1994 Proc Natl Acad Sci 91:6496–6500) to control expression of both marker and therapeutic genes by human fibrosarcoma cells in response to hypoxia in vitro and within solid tumours in vivo (Dachs et al ibid). Alternatively, the fact that marked glucose deprivation is also present in ischaemic areas of tumours can be used to activate heterologous gene expression specifically in tumours. A truncated 632 base pair sequence of the grp 78 gene promoter, known to be activated specifically by glucose deprivation, has also been shown to be capable of driving high level expression of a reporter gene in murine tumours in vivo (Gazit et al 1995 Cancer Res 55:1660).

An alternative method of regulating the expression of such components is by using the tetracycline on/off system described by Gossen and Bujard (1992 Proc Nat; Acad Sci 89: 5547) as described for the production of retroviral gal, pol and VSV-G proteins by Yoshida et al (1997 Biochem Biophys Res Comm 230: 426). Unusually this regulatory system is also used in the present invention to control the production of the pro-vector genome. This ensures that no vector components are expressed from the adenoviral vector in the absence of tetracycline.

Safety features which may be incorporated into the hybrid viral vector system are described below. One or more such features may be present.

The secondary vector is also advantageous for in vivo use in that incorporated into it are one or more features which eliminate the possibility of recombination to produce an infectious virus capable of independent replication. Such features were not included in previous published studies (Feng et al 1997 ibid). In particular, the construction of a retroviral vector from three components as described below was not described by Feng et al (ibid).

Firstly, sequence homology between the sequences encoding the components of the secondary vector may be avoided by deletion of regions of homology. Regions of homology allow genetic recombination to occur. In a particular embodiment, three transcription units are used to construct a secondary retroviral vector. The first transcription unit contains a retroviral gag-pol gene under the control of a non-retroviral promoter and enhancer. The second transcription unit contains a retroviral env gene under the control of a non-retroviral promoter and enhancer. The third transcription unit comprises a defective retroviral genome under the control of a non-retroviral promoter and enhancer. In the native retroviral genome, the packaging signal is located such that part of the gag sequence is required for proper functioning. Normally when retroviral vector systems are constructed therefrom, the packaging signal, including part of the gag gene, remains in the vector genome. In the present case however, the defective retroviral genome contains a minimal packaging signal which does not contain sequences homologous to gag sequences in the first transcription unit. Also, in retroviruses, for example Moloney Murine Leukaemia virus (MMLV), there is a small region of overlap between the 3' end of the pol coding sequence and the 5' end of env. The corresponding region of homology between the first and second transcription units may be removed by altering the sequence of either the 3' end of the pol coding sequence or the 5' end of env so as to change the codon usage but not the amino acid sequence of the encoded proteins.

Secondly, the possibility of replication competent secondary viral vectors may be avoided by pseudotyping the genome of one retrovirus with the Env protein of another retrovirus or another enveloped virus so that regions of homology between the env and gag-pol components are avoided.

In a particular embodiment the retroviral vector is constructed from the following three components: The first transcription unit contains a retroviral gag-pol gene under the control of a non-retroviral promoter and enhancer. The second transcription unit contains the env gene from the alternative enveloped virus, under the control of a non-retroviral promoter and enhancer. The third transcription unit comprises a defective retroviral genome under the control of a non-retroviral promoter and enhancer. The defective retroviral genome contains a minimal packaging signal which does not contain sequences homologous to gag sequences in the first transcription unit.

Thirdly, the possibility of replication competent retroviruses can be eliminated by using two transcription units constructed in a particular way. The first transcription unit contains a gag-pol coding region under the control of a promoter-enhancer active in the primary target cell such as a hCMV promoter-enhancer or a tissue restricted promoter-enhancer. The second transcription unit encodes a retroviral genome RNA capable of being packaged into a retroviral particle. The second transcription unit contains retroviral sequences necessary for packaging, integration and reverse transcription and also contains sequences coding for an env protein of an enveloped virus and the coding sequence of one or more therapeutic genes.

In this example, the transcription of the env and an NOI coding sequences is devised such that the Env protein is preferentially produced in the primary target cell while the NOI expression product is or are preferentially produced in the secondary target cell.

A suitable intron splicing arrangement is described later on in Example 5 and illustrated in FIG. 17 and FIG. 27*c*. Here, a splice donor site is positioned downstream of a splice acceptor site in the retroviral genome sequence delivered by the primary vector to the primary target cell. Splicing will therefore be absent or infrequent in the primary target cell so the Env protein will preferentially be expressed. However, once the vector genome has gone through the process of reverse transcription and integration into the secondary target cell, a functional splice donor sequence will be located in the 5' LTR, upstream of a functional splice acceptor sequence. Splicing occurs to splice out the env sequence and transcripts of the NOI are produced.

In a second arrangement of this example, the expression of an NOI is restricted to the secondary target cell and prevented from being expressed in the primary target cell as follows: This arrangement is described later on in Example 6 and illustrated in FIG. 18. There, a promoter-enhancer and a first fragment of an NOI containing the 5' end of the coding sequence and a natural or artificially derived or derivable splice donor sequence are inserted at the 3' end of the retroviral genome construct upstream of the R-region. A second fragment of the NOI which contains all the sequences required to complete the coding region is placed downstream of a natural or artificially derived or derivable splice acceptor sequence located downstream from the packaging signal in the retroviral genome construct. On reverse transcription and integration of the retroviral genome in the secondary target cell, the promoter 5' fragment of the NOI and the functional splice donor sequence are located upstream of the functional splice acceptor and the 3' end of the NOI. Transcription from the promoter and splicing then permit translation of the NOI in the secondary target cell.

In a preferred embodiment the hybrid viral vector system according to the invention comprises single or multiple adenoviral primary vectors which encodes or encode a retroviral secondary vector.

Preferred embodiments of the present invention described address one of the major problems associated with adenoviral and other viral vectors, namely that gene expression from such vectors is transient. The retroviral particles generated from the primary target cells can transduce secondary target cells and gene expression in the secondary target cells is stably maintained because of the integration of the retroviral vector genome into the host cell genome. The secondary target cells do not express significant amounts of viral protein antigens and so are less immunogenic than cells transduced with adenoviral vector.

The use of a retroviral vector as the secondary vector is advantageous because it allows a degree of cellular discrimination, for instance by permitting the targeting of rapidly dividing cells. Furthermore, retroviral integration permits the stable expression of therapeutic genes in the target tissue, including stable expression in proliferating target cells.

The use of the novel retroviral vector design of the present invention is also advantageous in that gene expression can be limited to a primary or a secondary target site. In this way, single or multiple NOIs can be preferentially expressed at a secondary target site and poorly expressed or not expressed at a biologically significant level at a primary target site. As a result, the possible toxicity or antigenicity of an NOI may be avoided.

Preferably, the primary viral vector preferentially transduces a certain cell type or cell types.

More preferably, the primary vector is a targeted vector, that is it has a tissue tropism which is altered compared to the native virus, so that the vector is targeted to particular cells.

The term "targeted vector" is not necessarily linked to the term "target site" or target cell".

"Target site" refers to a site which a vector, whether native or targeted, is capable of transfecting or transducing.

"Primary target site" refers to a first site which a vector, whether native or targeted, is capable of transfecting or transducing.

"Secondary target site" refers to a second site which a vector, whether native or targeted, is capable of transfecting or transducing.

"Target cell" simply refers to a cell which a vector, whether native or targeted, is capable of transfecting or transducing.

"Primary target cell" refers to a first cell which a vector, whether native or targeted, is capable of transfecting or transducing.

"Secondary target cell" refers to a second cell which a vector, whether native or targeted, is capable of transfecting or transducing.

The preferred, adenoviral primary vector according to the invention is also preferably a targeted vector, in which the tissue tropism of the vector is altered from that of a wild-type adenovirus. Adenoviral vectors can be modified to produce targeted adenoviral vectors for example as described in: Krasnykh et al 1996 J. Virol 70: 6839–6846; Wickham et al 1996 J. Virol 70: 6831–838; Stevenson et al 1997 J. Virol 71: 4782–4790; Wickham et at 1995 Gene Therapy 2: 750–756; Douglas et at 1997 Neuromuscul. Disord 7:284–298; Wickham et at 1996 Nature Biotechnology 14: 1570–1573.

Primary target cells for the vector system according to the invention include s haematopoietic cells (including monocytes, macrophages, lymphocytes, granulocytes or progenitor cells of any of these); endothelial cells; tumour cells; stromal cells; astrocytes or glial cells; muscle cells; and epithelial cells.

Thus, a primary target cell according to the invention, capable of producing the second viral vector, may be of any of the above cell types.

In a preferred embodiment, the primary target cell according to the invention is a monocyte or macrophage transduced by a defective adenoviral vector containing a first transcription unit for a retroviral gag-pol and a second transcription unit capable of producing a packageable defective retroviral genome. In this case at least the second transcription unit is preferably under the control of a promoter-enhancer which is preferentially active in a diseased location within the body such as an ischaemic site or the micro-environment of a solid tumour.

In a particularly preferred embodiment, the second transcription unit is constructed such that on insertion of the genome into the secondary target cell, an intron is generated which serves to reduce expression of a viral essential element, such as the viral env gene, and permit efficient expression of a therapeutic and/or diagnostic NOI or NOIs.

The packaging cell may be an in vivo packaging cell in the body of an individual to be treated or it may be a cell cultured in vitro such as a tissue culture cell line. Suitable cell lines include mammalian cells such as murine fibroblast derived cell lines or human cell lines. Preferably the packaging cell line is a human cell line, such as for example: HEK293, 293-T, TE671, HT1080.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells. Alternatively the packaging and vector components may be administered to the packaging cell in vivo. Methods for introducing retroviral packaging and vector components into cells of an individual are known in the art. For example, one approach is to introduce the different DNA sequences that are required to produce a retroviral vector particle e.g. the env coding sequence, the gag-pol coding sequence and the defective retroviral genome into the cell simultaneously by transient triple transfection (Landau & Littman 1992 J. Virol. 66, 5110; Soneoka et al 1995 Nucleic Acids Res 23:628–633).

The secondary viral vectors may also be targeted vectors. For retroviral vectors, this may be achieved by modifying the Env protein. The Env protein of the retroviral secondary vector needs to be a non-toxic envelope or an envelope which may be produced in non-toxic amounts within the primary target cell, such as for example a MMLV amphotropic envelope or a modified amphotropic envelope. The safety feature in such a case is preferably the deletion of regions or sequence homology between retroviral components.

Preferably the envelope is one which allows transduction of human cells. Examples of suitable env genes include, but are not limited to, VSV-G, a MLV amphotropic env such as the 4070A env, the RD114 feline leukaemia virus env or haemagglutinin (HA) from an influenza virus. The Env protein may be one which is capable of binding to a receptor on a limited number of human cell types and may be an engineered envelope containing targeting moieties. The env and gag-pol coding sequences are transcribed from a promoter and optionally an enhancer active in the chosen packaging cell line and the transcription unit is terminated by a polyadenylation signal. For example, if the packaging cell is a human cell, a suitable promoter-enhancer combination is that from the human cytomegalovirus major immediate early (hCMV-MIE) gene and a polyadenylation signal from SV40 virus may be used. Other suitable promoters and polyadenylation signals are known in the art.

The secondary target cell population may be the same as the primary target cell population. For example delivery of a primary vector of the invention to tumour cells leads to replication and generation of further vector particles which can transduce further tumour cells.

Alternatively, the secondary target cell population may be different from the primary target cell population. In this case the primary target cells serve as an endogenous factory within the body of the treated individual and produce additional vector particles which can transduce the secondary target cell population. For example, the primary target cell population may be haematopoietic cells transduced by the primary vector in vivo or ea vivo. The primary target cells are then delivered to or migrate to a site within the body such as a tumour and produce the secondary vector particles, which are capable of transducing for example mitotically active tumour cells within a solid tumour.

The retroviral vector particle according to the invention will also be capable of transducing cells which are slowly-dividing, and which non-lentiviruses such as MLV would not be able to efficiently transduce. Slowly-dividing cells divide once in about every three to four days including certain tumour cells. Although tumours contain rapidly dividing cells, some tumour cells especially those in the centre of the tumour, divide infrequently. Alternatively the target cell may be a growth-arrested cell capable of undergoing cell division such as a cell in a central portion of a tumour mass or a stem cell such as a haematopoietic stem cell or a CD34-positive cell. As a further alternative, the target cell may be a precursor of a differentiated cell such as a monocyte precursor, a CD33-positive cell, or a myeloid precursor. As a further alternative, the target cell may be a differentiated cell such as a neuron, astrocyte, glial cell, microglial cell, macrophage, monocyte, epithelial cell, endothelial cell, hepatocyte, spermatocyte, spermatid or spermatozoa. Target cells may be transduced either in vitro after isolation from a human individual or may be transduced directly in vivo.

The invention permits the localised production of high titres of defective retroviral vector particles in vivo at or near the site at which action of a therapeutic protein or proteins is required with consequent efficient transduction of secondary target cells. This is more efficient than using either a defective adenoviral vector or a defective retroviral vector alone.

The invention also permits the production of retroviral vectors such as MMLV-based vectors in non-dividing and slowly-dividing cells in vivo. It had previously been possible to produce MMLV-based retroviral vectors only in rapidly dividing cells such as tissue culture-adapted cells proliferating in vitro or rapidly dividing tumour cells in vivo. Extending the range of cell types capable of producing retroviral vectors is advantageous for delivery of genes to the cells of solid tumours, many of which are dividing slowly, and for the use of non-dividing cells such as endothelial cells and cells of various haematopoietic lineages as endogenous factories for the production of therapeutic protein products.

The delivery of one or more therapeutic genes by a vector system according to the present invention may be used alone or in combination with other treatments or components of the treatment.

For example, the retroviral vector of the present invention may be used to deliver one or more NOI(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cacbexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the retroviral vector of the present invention may be used to deliver one or more NOI(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the retroviral vector of the present invention may be used to deliver one or more NOI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other -oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Further provided according to the invention are methods of controlling production of a therapeutic NOI or NOIs such that the therapeutic NOI or NOIs is/are preferentially expressed in a secondary target cell population and is/are poorly expressed or not expressed at a biologically significant level in a primary target cell.

The present invention also provides a pharmaceutical composition for treating an individual by gene therapy, wherein the composition comprises a therapeutically effective amount of the retroviral vector of the present invention comprising one or more deliverable therapeutic and//or diagnostic NOI(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

In a further aspect of the present invention, there is provided a hybrid viral vector system in the general sense (i.e. not necessarily limited to the aforementioned first aspect of the present invention as defined above) for in vivo gene delivery, which system comprises one or more primary viral vectors which encode a secondary viral vector, the primary vector or vectors capable of infecting a first target cell and of expressing therein the secondary viral vector, which secondary vector is capable of transducing a secondary target cell.

With this particular embodiment, the genetic vector of the invention is thus a hybrid viral vector system for gene delivery which is capable of generation of defective infectious particles from within a target cell. Thus a genetic vector of the invention consists of a primary vector manufactured in vitro which encodes the genes necessary to produce a secondary vector in viva. In use, the secondary vector carries one or more selected genes for insertion into the secondary target cell. The selected genes may be one or more marker genes and/or therapeutic genes. Marker genes encode selectable and/or detectable proteins.

More aspects concerning this particular aspect of the present invention now follow—which teachings are also applicable to the aforementioned aspects of the present invention.

In another aspect the invention provides target cells infected by the primary viral vector or vectors and capable of producing infectious secondary viral vector particles.

In a further aspect the invention provides a method of treatment of a human or non-human mammal, which method comprises administering a hybrid viral vector system or target cells infected by the primary viral vector or vectors, as described herein.

The primary viral vector or vectors may be a variety of different viral vectors, such as retroviral, adenoviral, herpes virus or pox virus vectors, or in the case of multiple primary viral vectors, they may be a mixture of vectors of different viral origin. In whichever case, the primary viral vectors are preferably defective in that they are incapable of independent replication. Thus, they are capable of entering a target cell and delivering the secondary vector sequences, but not of replicating so as to go on to infect further target cells.

In the case where the hybrid viral vector system comprises more than one primary vector to encode the secondary vector, both or all three primary vectors will be used to infect a primary target cell population, usually simultaneously. Preferably, there is a single primary viral vector which encodes all components of the secondary viral vector.

The preferred single or multiple primary viral vectors are adenoviral vectors. Adenovirus vectors have significant advantages over other viral vectors in terms of the titres which can be obtained from in vitro cultures. The adenoviral particles are also comparatively stable compared with those of enveloped viruses and are therefore more readily purified and stored. However, current adenoviral vectors suffer from major limitations for in vivo therapeutic use since gene expression from defective adenoviral vectors is only transient.

Because the vector genome does not replicate, target cell proliferation leads to dilution of the vector. Also cells expressing adenoviral proteins, even at a low level, are destroyed by an immunological response raised against the adenoviral proteins.

The secondary viral vector is preferably a retroviral vector. The secondary vector is produced by expression of essential genes for assembly and packaging of a defective viral vector particle, within the primary target cells. It is defective in that it is incapable of independent replication. Thus, once the secondary retroviral vector has transduced a secondary target cell, it is incapable of spreading by replication to any further target cells.

The secondary vector may be produced from expression of essential genes for retroviral vector production encoded in the DNA of the primary vector. Such genes may include a gag-pol gene from a retrovirus, an envelope gene from an enveloped virus and a defective retroviral genome containing one or more therapeutic genes. The defective retroviral genome contains in general terms sequences to enable reverse transcription, at least part of a 5' long terminal repeat (LTR), at least part of a 3'LTR and a packaging signal.

Importantly, the secondary vector is also safe for in vivo use in that incorporated into it are one or more safety features which eliminate the possibility of recombination to produce an infectious virus capable of independent replication.

To ensure that it is replication defective the secondary vector may be encoded by a plurality of transcription units, which may be located in a single or in two or more adenoviral or other primary vectors. Thus, there may be a transcription unit encoding the secondary vector genome, a transcription unit encoding gag-pol and a transcription unit encoding env. Alternatively, two or more of these may be combined. For example, nucleic acid sequences encoding gag-pol and env, or env and the genome, may be combined in a single transcription unit. Ways of achieving this are known in the art.

Transcription units as described herein are regions of nucleic acid containing coding sequences and the signals for achieving expression of those coding sequences independently of any other coding sequences. Thus, each transcription unit generally comprises at least a promoter, an enhancer and a polyadenylation signal. The promoter and enhancer of the transcription units encoding the secondary vector are preferably strongly active, or capable of being strongly induced, in the primary target cells under conditions for production of the secondary viral vector. The promoter and/or enhancer may be constitutively efficient, or may be tissue or temporally restricted in their activity. Examples of suitable tissue restricted promoters/enhancers are those which are highly active in tumour cells such as a promoter/enhancer from a MUC 1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. One preferred promoter-enhancer combination is a human cytomegalovirus (hCMV) major immediate early (MIE) promoter/enhancer combination.

Hypoxia or ischaemia regulatable expression of secondary vector components may be particularly useful under certain circumstances. Hypoxia is a powerful regulator of gene expression in a wide range of different cell types and acts by the induction of the activity of hypoxia-inducible transcription factors such as hypoxia inducible factor-1 (HIF-1; Wang & Semenza (1993). Proc. Natl. Acad. Sci USA 90:430), which bind to cognate DNA recognition sites, the hypoxia-responsive elements (HREs) on various gene promoters. Dachs et al (1997). Nature Med. 5: 515.) have used a multimeric form of the HRE from the mouse phosphoglycerate kinase-1 (PGK-1) gene (Firth et al. (1994). Proc. Natl. Acad. Sci USA 91:6496–6500) to control expression of both marker and therapeutic genes by human fibrosarcoma cells in response to hypoxia in vitro and within solid tumours in vivo (Dachs et al ibid). Alternatively, the fact that marked glucose deprivation is also present in ischaemic areas of tumours can be used to activate heterologous gene expression specifically in tumours. A truncated 632 base pair sequence of the grp 78 gene promoter, known to be activated specifically by glucose deprivation, has also been shown to be capable of driving high level expression of a reporter gene in murine tumours in vivo (Gazit G, et al (1995). Cancer Res. 55:1660).

Safety features which may be incorporated into the hybrid viral vector system are described below. One or more such features may be present.

Firstly, sequence homology between the sequences encoding the components of the secondary vector may be avoided by deletion of regions of homology. Regions of homology allow genetic recombination to occur. In a particular embodiment, three transcription units are used to construct a secondary retroviral vector. A first transcription unit contains a retroviral gag-pol gene under the control of a non-retroviral promoter and enhancer. A second transcription unit contains a retroviral env gene under the control of a non-retroviral promoter and enhancer. A third transcription unit comprises a defective retroviral genome under the control of a non-retroviral promoter and enhancer. In the native retroviral genome, the packaging signal is located such that part of the gag sequence is required for proper functioning. Normally when retroviral vector systems are constructed therefore, the packaging signal, including part of the gag gene, remains in the vector genome. In the present case however, the defective retroviral genome contains a minimal packaging signal which does not contain sequences homologous to gag sequences in the first transcription unit. Also, in retroviruses, for example Moloney Murine Leukaemia virus (MMLV), there is a small region of overlap between the 3' end of the pol coding sequence and the 5' end of env. The corresponding region of homology between the first and second transcription units may be removed by altering the sequence of either the 3' end of the pol coding sequence or the 5' end of env so as to change the codon usage but not the amino acid sequence of the encoded proteins.

Secondly, the possibility of replication competent secondary viral vectors may be avoided by pseudotyping the genome of one retrovirus with the envelope protein of another retrovirus or another enveloped virus so that regions of homology between the env and gag-pol components are avoided. In a particular embodiment the retroviral vector is constructed from the following three components. The first transcription unit contains a retroviral gag-pol gene under the control of a non-retroviral promoter and enhancer. The second transcription unit contains the env gene from the alternative enveloped virus, under the control of a non-retroviral promoter and enhancer. The third transcription unit comprises a defective retroviral genome under the control of a non-retroviral promoter and enhancer. The defective retroviral genome contains a minimal packaging signal which does not contain sequences homologous to gag sequences in the first transcription unit.

Pseudotyping may involve for example a retroviral genome based on a lentivirus such as an HIV or equine infectious anaemia virus (EIAV) and the envelope protein may for example be the amphotropic envelope protein designated 4070A. Alternatively, the retroviral genome may be based on MMLV and the envelope protein may be a protein from another virus which can be produced in non-toxic amounts within the primary target cell such as an Influenza haemagglutinin or vesicular stomatitis virus G protein. In another alternative, the envelope protein may be a modified envelope protein such as a mutant or engineered envelope protein. Modifications may be made or selected to introduce targeting ability or to reduce toxicity or for another purpose.

Thirdly, the possibility of replication competent retroviruses can be eliminated by using two transcription units constructed in a particular way. The first transcription unit contains a gag-pol coding region under the control of a promoter-enhancer active in the primary target cell such as a hCMV promoter-enhancer or a tissue restricted promoter-enhancer. The second transcription unit encodes a retroviral genome RNA capable of being packaged into a retroviral particle. The second transcription unit contains retroviral sequences necessary for packaging, integration and reverse transcription and also contains sequences coding for an env protein of an enveloped virus and the coding sequence of one or more therapeutic genes.

In a preferred embodiment the hybrid viral vector system according to the invention comprises single or multiple adenoviral primary vectors which encodes or encode a retroviral secondary vector. Adenoviral vectors for use in the invention may be derived from a human adenovirus or an adenovirus which does not normally infect humans. Preferably the vectors are derived from Adenovirus Type 2 or adenovirus Type 5 (Ad2 or Ad5) or a mouse adenovirus or an avian adenovirus such as CELO virus (Cotton et al 1993 J. Virol. 67:3777–3785). The vectors may be replication competent adenoviral vectors but are more preferably defective adenoviral vectors. Adenoviral vectors may be rendered defective by deletion of one or more components necessary for replication of the virus. Typically, each adenoviral vector contains at least a deletion in the E1 region. For production of infectious adenoviral vector particles, this deletion may be complemented by passage of the virus in a human embryo fibroblast cell line such as human 293 cell line, containing an integrated copy of the left portion of Ad5, including the E1 gene. The capacity for insertion of heterologous DNA into such vectors can be up to approximately 7 kb. Thus such vectors are useful for construction of a system according to the invention comprising three separate recombinant vectors each containing one of the essential transcription units for construction of the retroviral secondary vector.

Alternative adenoviral vectors are known in the art which contain further deletions in other adenoviral genes and these vectors are also suitable for use in the invention. Several of these second generation adenoviral vectors show reduced immunogenicity (eg E1+E2 deletions Gorziglia et al 1996 J. Virol. 70: 4173–4178; E1+E4 deletions Yeh et al 1996 J. Virol. 70: 559–565). Extended deletions serve to provide additional cloning capacity for the introduction of multiple genes in the vector. For example a 25 kb deletion has been described (Lieber et al. 1996 J. Virol. 70: 8944–8960) and a cloning vector deleted of all viral genes has been reported (Fisher et al 1996 Virolology 217: 11–22) which will permit the introduction of more than 35 kb of heterologous DNA. Such vectors may be used to generate an adenoviral primary vector according to the invention encoding two or three transcription units for construction of the retroviral secondary vector.

Embodiments of the invention described solve one of the major problems associated with adenoviral and other viral vectors, namely that gene expression from such vectors is transient. The retroviral particles generated from the primary target cells can infect secondary target cells and gene expression in the secondary target cells is stably maintained because of the integration of the retroviral vector genome into the host cell genome. The secondary target cells do not express significant amounts of viral protein antigens and so are less immunogenic than the cells transduced with adenoviral vector.

The use of a retroviral vector as the secondary vector is also advantageous because it allows a degree of cellular discrimination, for instance by permitting the targeting of rapidly dividing cells. Furthermore, retroviral integration permits the stable expression of therapeutic genes in the target tissue, including stable expression in proliferating target cells.

Preferably, the primary viral vector preferentially infects a certain cell type or cell types. More preferably, the primary vector is a targeted vector, that is it has a tissue tropism which is altered compared to the native virus, so that the vector is targeted to particular cells. The term "targeted vector" is not necessarily linked to the term "target cell". "target cell" simply refers to a cell which a vector, whether native or targeted, is capable of infecting or transducing.

The preferred, adenoviral primary vector according to the invention is also preferably a targeted vector, in which the tissue tropism of the vector is altered from that of a wild-type adenovirus. Adenoviral vectors can be modified to produce targeted adenoviral vectors for example as described in Krasnykh et al. 1996 J. Virol 70: 6839–6846; Wickham et al 1996 J. Virol 70: 6831–6838; Stevenson et al. 1997 J. Virol. 71: 4782–4790; Wickham et al. 1995 Gene Therapy 2: 750–756; Douglas et al. 1997 Neuromuscul. Disord. 7:284–298; Wickham et al. 1996 Nature Biotechnology 14: 1570–1573.

Primary target cells for the vector system according to the invention include but are not limited to haematopoietic cells (including monocytes, macrophages, lymphocytes, granulocytes or progenitor cells of any of these); endothelial cells; tumour cells; stromal cells; astrocytes or glial cells; muscle cells; and epithelial cells.

Thus, a primary target cell according to the invention, capable of producing the second viral vector, may be of any of the above cell types. In a preferred embodiment, the primary target cell according to the invention is a monocyte or macrophage infected by a defective adenoviral vector containing a first transcription unit for a retroviral gag-pol and a second transcription unit capable of producing a packageable defective retroviral genome. In this case at least the second transcription unit is preferably under the control of a promoter-enhancer which is preferentially active in a diseased location within the body such as an ischaemic site or the micro-environment of a solid tumour. In a particularly preferred embodiment of this aspect of the invention, the second transcription unit is constructed such that on insertion of the genome into the secondary target cell, an intron is generated which serves to reduce expression of the viral env gene and permit efficient expression of a therapeutic gene.

The secondary viral vectors may also be targeted vectors. For retroviral vectors, this may be achieved by modifying the envelope protein. The envelope protein of the retroviral secondary vector needs to be a non-toxic envelope or an envelope which may be produced in non-toxic amounts within the primary target cell, such as for example a MMLV amphotropic envelope or a modified amphotropic envelope. The safety feature in such a case is preferably the deletion of regions or sequence homology between retroviral components.

The secondary target cell population may be the same as the primary target cell population. For example delivery of a primary vector of the invention to tumour cells leads to replication and generation of further vector particles which can transduce further tumour cells. Alternatively, the secondary target cell population may be different from the primary target cell population. In this case the primary target cells serve as an endogenous factory within the body of the treated individual and produce additional vector particles which can infect the secondary target cell population. For example, the primary target cell population may be haematopoietic cells transduced by the primary vector in vivo or ex vivo. The primary target cells are then delivered to or migrate to a site within the body such as a tumour and produce the secondary vector particles, which are capable of transducing for example tumour cells within a solid tumour.

The invention permits the localised production of high titres of defective retroviral vector particles in vivo at or near the site at which action of a therapeutic protein or proteins is required with consequent efficient transduction of secondary target cells. This is more efficient than using either a defective adenoviral vector or a defective retroviral vector alone.

The invention also permits the production of retroviral vectors such as MMLV-based vectors in non-dividing and slowly-dividing cells in vivo. It had previously been possible to produce MMLV-based retroviral vectors only in rapidly dividing cells such as tissue culture-adapted cells proliferating in vitro or rapidly dividing tumour cells in vivo. Extending the range of cell types capable of producing retroviral vectors is advantageous for delivery of genes to the cells of solid tumours, many of which are dividing slowly, and for the use of non dividing cells such as endothelial cells and cells of various haematopoietic lineages as endogenous factories for the production of therapeutic protein products.

The delivery of one or more therapeutic genes by a vector system according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, vasoactive proteins or peptides, cytokines, chemokines, anti-viral proteins, antisense RNA and ribozymes.

In a preferred embodiment of a method of treatment according to the invention, a gene encoding a pro-drug activating enzyme is delivered to a tumour using the vector system of the invention and the individual is subsequently treated with an appropriate pro-drug. Examples of pro-drugs include etoposide phosphate (used with alkaline phosphatase Senter et al., 1988 Proc. Natl. Acad. Sci. 85: 4842–4846); 5-fluorocytosine (with Cytosine deaminase Mullen et al. 1994 Cancer Res. 54: 1503–1506); Doxorubicin-N-p-hydroxyphenoxyacetamide (with Penicillin-V-Amidase (Kerr et al. 1990 Cancer Immunol. Immunother. 31: 202–206); Para-N-bis(2-chloroethyl) aminobenzoyl glutamate (with Carboxypeptidase G2); Cephalosporin nitrogen mustard carbamates (with b-lactamase); SR4233 (with P450 Reducase); Ganciclovir (with HSV thymidine kinase, Borrelli et al. 1988 Proc . Natl. Acad. Sci. 85: 7572–7576) mustard pro-drugs with nitroreductase (Friedlos et al. 1997J Med Chem 40: 1270–1275) and Cyclophosphamide or Ifosfamide (with a cytochrome P450 Chen et al. 1996 Cancer Res 56: 1331–1340).

Further provided according to the invention are methods of controlling production of a therapeutic gene such that the therapeutic gene is preferentially expressed in the secondary target cell population and is poorly expressed or not expressed at a biologically significant level in the primary target cell.

In accordance with the invention, standard molecular biology techniques may be used which are within the level of skill in the art. Such techniques are fully described in the literature. See for example; Sambrook et al (1989) Molecular Cloning; a laboratory manual; Hames and Glover (1985–1997) DNA Cloning: a practical approach, Volumes I–IV (second edition); Methods for the engineering of immunoglobulin genes are given in McCafferty et al (1996) "Antibody Engineering: A Practical Approach".

In summation, the present invention relates to a novel delivery system suitable for introducing one or more NOIs into a target cell.

In one broad aspect the present invention relates to a retroviral vector comprising a functional splice donor site and a functional splice acceptor site; wherein the functional splice donor site and the functional splice acceptor site flank a first nucleotide sequence of interest ("NOI"); wherein the functional splice donor site is upstream of the functional splice acceptor site; wherein the retroviral vector is derived from a retroviral pro-vector; wherein the retroviral pro-vector comprises a first nucleotide sequence ("NS") capable of yielding the functional splice donor site and a second NS capable of yielding the functional splice acceptor site; wherein the first NS is downstream of the second NS; such that the retroviral vector is formed as a result of reverse transcription of the retroviral pro-vector.

In a further broad aspect, the present invention provides a hybrid viral vector system for in vivo gene delivery, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on a adenoviral vector and/or the secondary viral vector is obtainable from or is based on a retroviral vector preferably a lentiviral vector.

The invention will now be further described by way of example in which reference is made to the following Figures:

FIG. 1 which shows the structure of a retroviral proviral genome;

FIG. 2 which shows the addition of a small T splice donor pLTR (SEQ ID NOS 23 and 24, respectively, in order of appearance);

FIG. 3 which shows a diagrammatic representation of pL-SA-N (SEQ ID NOS 25, and 26, respectively, in order of appearance);

FIG. 4 which shows a diagrammatic representation of pL-SA-N with a splice donor deletion (SEQ ID NOS 27 and 28, respectively, in order of appearance); FIG. 5 which shows the sequence of MLV pICUT (SEQ ID NO: 1);

FIG. 6 which shows the insertion of a splice donor at CMV/R junction of ELAV LTR plasmid (SEQ ID NOS 29 and 30, respectively, in order of appearance);

FIG. 7 which shows the insertion of a splice acceptor into pEGASUS-1 (SEQ ID NOS 31 and 32, respectively, in order of appearance);

FIG. 8 which shows the removal of a wild-type splice donor from EIAV vector (SEQ ID NOS 33–36 respectively, in order of appearance);

FIG. 9 which shows the combination of pCMVLTR+SD with pEGASUS+SA (noSD) to create pEICUT-1;

FIG. 10 which shows the construction of pEICUT-LacZ

FIG. 11 which shows the pEICUT-LacZ sequence (SEQ ID NO: 2);

FIG. 12 which shows the vector configuration in both transfected and transduced cells;

FIG. 13 which shows the restriction of gene expression to either packaging or transduced cells;

FIG. 14 which shows the construction of a MLV pICUT Neo-p450 vector that restricts hygromycin expression to producer cells and 2B6 (a p450 isoform) expression to transduced cells;

FIG. 15 which shows a sequence comparison of mutant env (m4070A) (SEQ ID NO: 5) with wild type MMLV sequencer (SEQ ID NO: 4) from the 3' end of the pol gene;

FIG. 16 which shows the complete sequence (SEQ ID NO: 3) of the modified env gene m4070A;

FIG. 17 which shows a restricted gene expression construct; 4070A Envelope to a first cell; p450 to a second cell;

FIG. 18 which shows the use of an intron to restrict NOI (in this example p450) expression to a transduced cell;

FIG. 19 which shows a pictorial representation of the Transfer vector-pE1sp1A;

FIG. 20 which shows a pictorial representation of pE1sp1A construct;

FIG. 21 which shows a pictorial representation of pE1RevE construct;

FIG. 22 which shows a pictorial representation of pE1HORSE3.1-gagpol construct;

FIG. 23 which shows a pictorial representation of pE1PEGASUS4-Genome construct;

FIG. 24 which shows a pictorial representation of pCI-Neo construct;

FIG. 25 which shows a pictorial representation of pCI-Rab construct;

FIG. 26 which shows a pictorial representation of pE1Rab construct;

FIG. 27*a* is a schematic representation of the natural splicing configuration in a retroviral vector;

FIG. 27*b* is a schematic representation of the splicing configuration in known retroviral vectors;

FIG. 27*c* is a schematic representation of the splicing configuration according to the present invention; and FIG. 28 is a schematic representation of the dual hybrid viral vector system according to the present invention.

In slightly more detail:

FIG. 1 shows the structure of a retroviral proviral genome. In this regard, the simplest retroviruses such as the murine oncoretroviruses have three open reading frames; gag, pol and env. Frameshift during gag translation leads to pol translation. Env expression and translation is achieved by splicing between the splice donor (SD) and splice acceptor (SA) shown. The packaging signal is indicated as Psi and is only contained in the full length transcripts—not the env expressing sub-genomic transcripts where this signal is removed during the splicing event.

FIG. 2 schematically shows the addition of small T splice donor to pLTR. Here, the small-t splice donor sequence is inserted into an LTR vector downstream of the start of transcription but upstream of R sequence such that upon reverse transcription (in the final construct) the U3-splice donor-R cassette is 'inherited' to 5' end of the proviral vector and RNA transcripts expressed contain a splice donor sequence near their 5' terminus.

FIG. 3 shows a schematic diagram of pL-SA-N. Both the consensus splice acceptor (T/C)nNC/TAG-G (Mount 1982 Nucleic Acids Res 10: 459–472) and branch point are shown in underline and bold The arrow indicates the intron/exon junction. Here, the consensus splice acceptor sequence is inserted into the Stu1/BamH1 sites of pLXSN. By such positioning this acceptor will therefore interact with any upstream splice donor (in the final RNA transcripts).

FIG. 4 shows a schematic diagram for the construction of pL-SA-N with a splice donor deletion. The gT to gC change is made by performing a PCR reaction on the pL-SA-N vector with the two oligonucleotides shown below. The resulting product is then cloned Spe1-Asc1 into pL-SA-N thus replacing the wild-type splice donor gT with gC. Both Spe1 and Asc1 sites are shown in bold and the mutation in the Spe1 oligonucleotide shown in captial bold.

FIG. 5 shows the sequence of MLV pICUT.

FIG. 6 shows a schematic diagram of the insertion of splice donor at CMV/R junction of EIAV LTR plasmid. PCR is performed with the two oligonulceotides outlined below and the resulting PCR product cloned Sac1-BamH1 into CMVLTR with the equivalent piece removed. In the Sac1 oligonucleotide the arrow indicates the start of transcription, the new insert is shown in capital with splice donor sequence underlined. The start of R is shown in italics.

FIG. 7 shows a schematic diagram of the insertion of splice acceptor into pEGASUS-1. Here, the double stranded oligonucleotide described below is inserted into Xho1-Bpu1102 digested pEGASUS-i to generate plasmid PEGASUS+SA. Both consensus splice acceptor (T/C)nNC/TAG-G (Mount 1982 ibid) and branch point are shown in underline and bold. The arrow indicates the intron/exon junction.

FIG. 8 shows a schematic diagram of the removal of wild-type splice donor from EIAV vector. Splice donor sequence removed by overlapping PCR using the oliognucleotides described below and the template pEGASUS+SA. First separate PCR reactions are performed with oligos1+2 and oligos3+4. The resulting amplified products are then eluted and used combined in a third PCR reaction. After 10 cycles of this third reaction oligo2 and 4 are then added. The resulting product is then cloned Sac1-Sal1 into pEGASUS+SA to create the plasmid pEGASUS+SA (noSD). The position of the splice donor (SD) is indicated. The point mutation changing the wild-type splice donor from GT to GC is shown in bold both in oligol and the complementary oligo3.

FIG. 11 shows the pEICUT-LacZ sequence.

Figure 12:
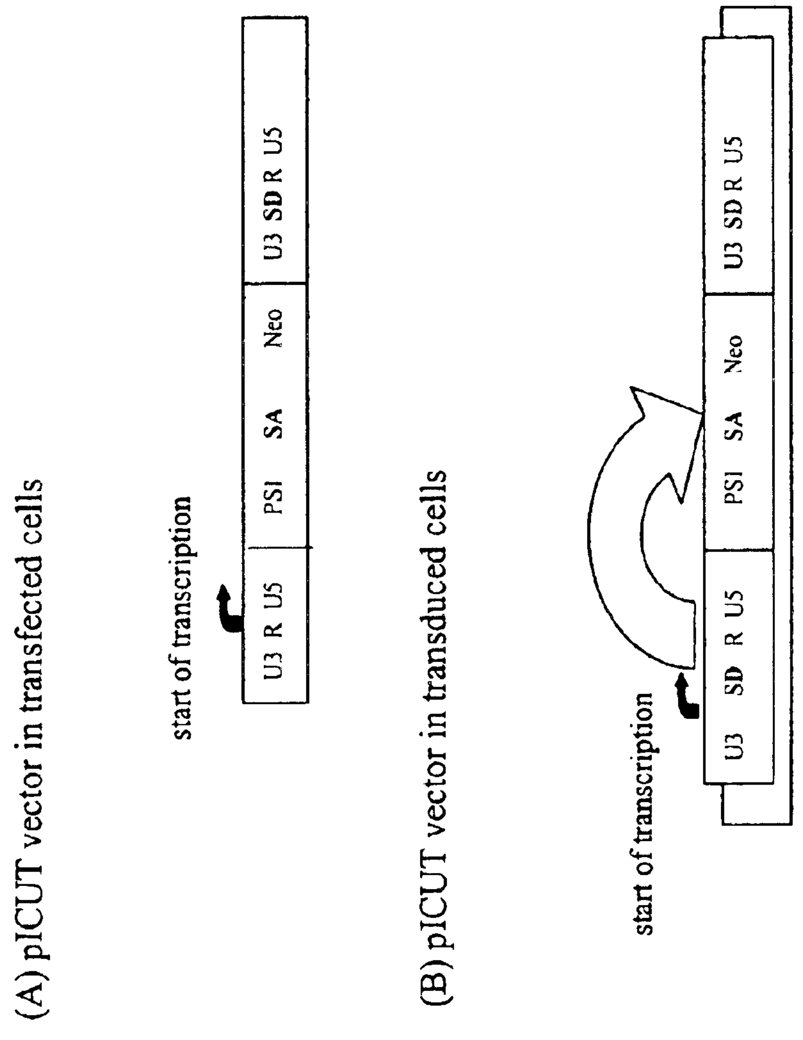

FIG. 12 shows a schematic diagram of the vector configuration in both transfected and transduced cells. Here, the starting pICUT vector contains no splice donor upstream of a splice acceptor (in this instance the consensus splice acceptor derived from IgSA) and therefore the resulting RNA transcripts will not be spliced. Thus all transcripts will be full length transcripts containing a packaging signal (A). Upon transduction however the splice donor (in this instance the small-T spliced donor) is 'inherited' to the 5' of the proviral vector such that all RNA transcripts now produced contain splice donor upstream of a splice acceptor i.e. an intron and thus maximal splicing achieved (B).

Figure 13:
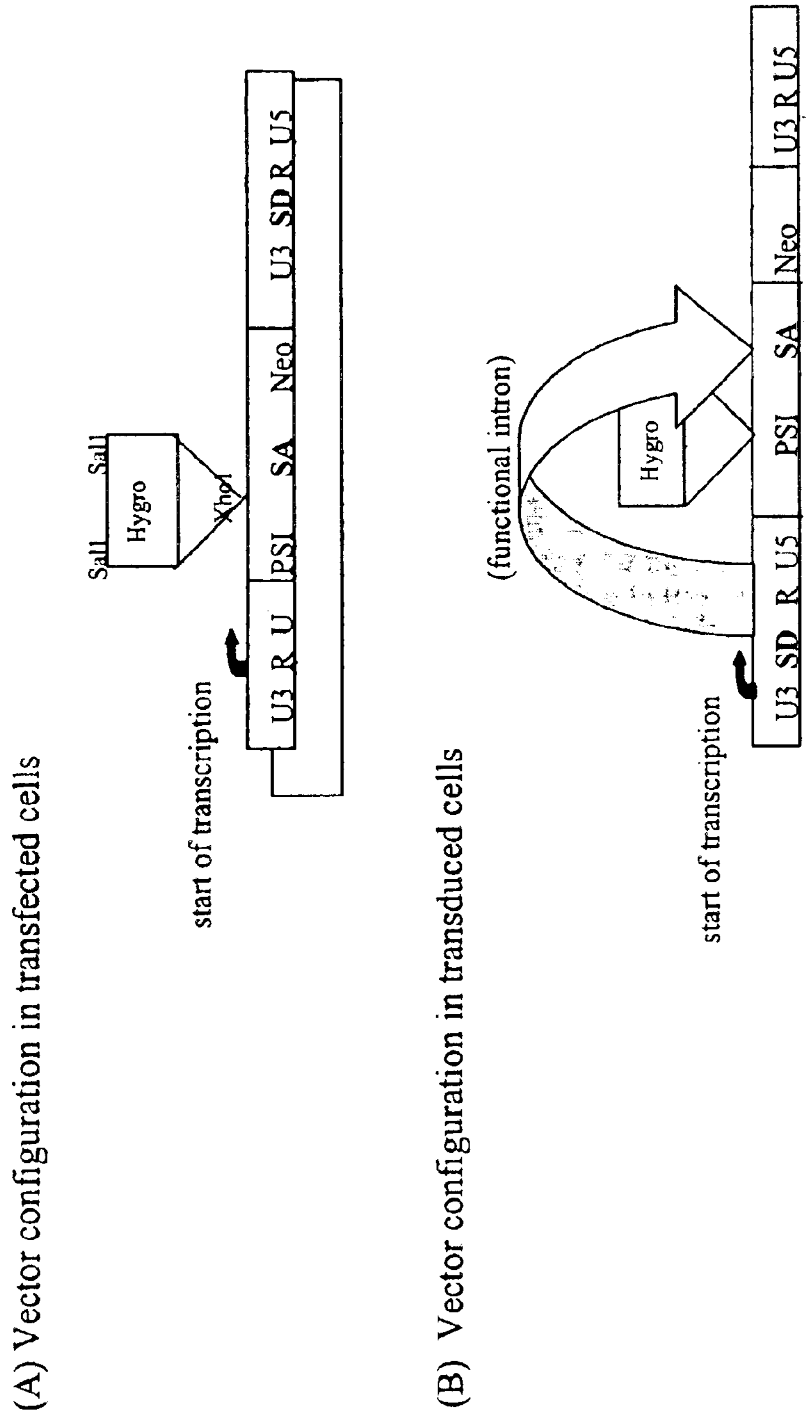

FIG. 13 shows a schematic diagram of the restriction of gene expression to either packaging and transduced cells. Restriction of gene expression in this instance is achieved by placing the hygromycin ORF upstream of the neomycin ORF in MLV pEICUT (a). By this cloning strategy the resulting vector will now express RNA transcripts that express hygromycin only in transfected cells because ribosome 5' cap-dependent translation will read only the upstream ORF efficiently. However upon transduction hygromycin is now contained within a functional intron and is thus deleted from mature transcripts (b) and thus neomycin ORF is now translated in a 5' cap-dependent manner.

Figure 14:
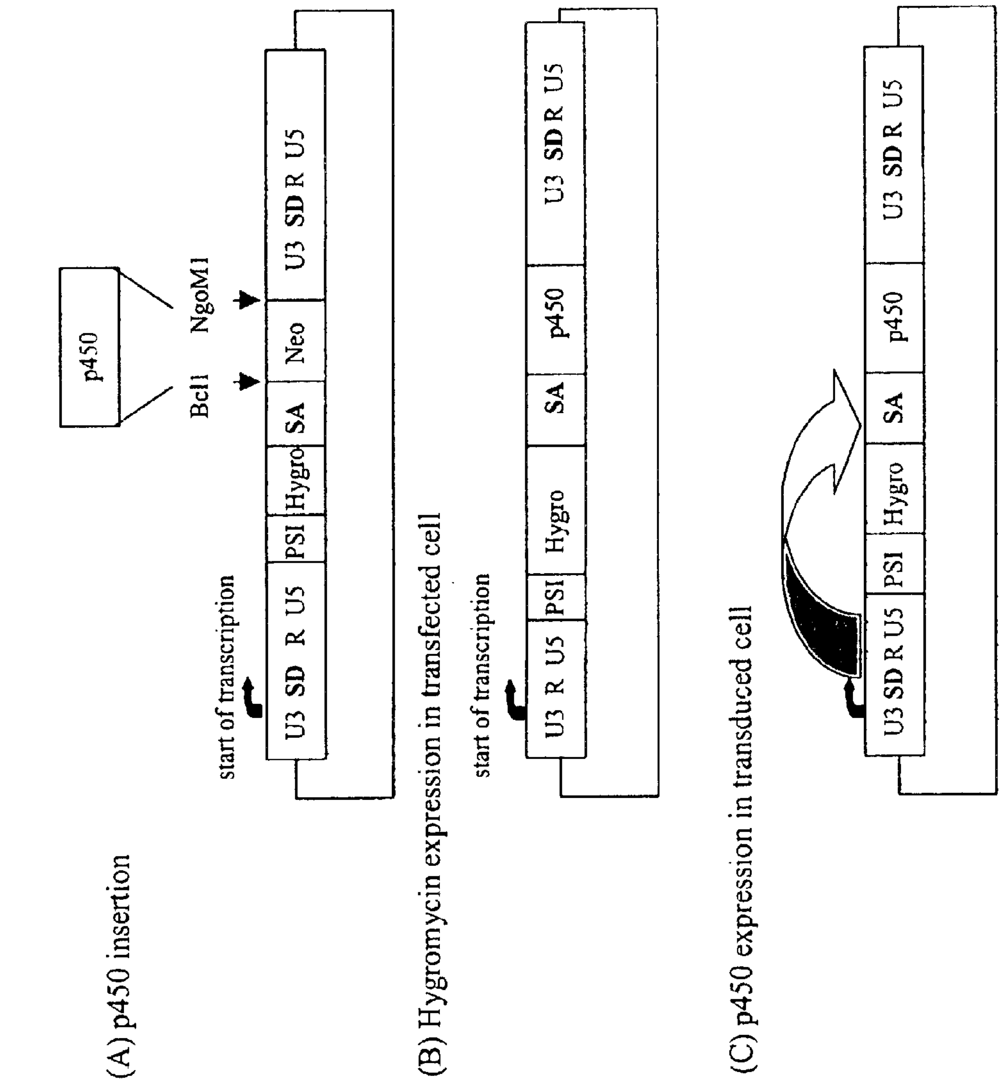

FIG. 14 shows a schematic diagram of the construction of a MLV pICUT Neo-p450 vector that restricts hygromycin expression to producer cells and 2B6 (a p450 isoform) expression to transduced cells. The starting vector for this construction is the pICUT vector of FIG. 13 containing both hygro and neo. The neo gene is replaced with the complete p450 2B6 cDNA as follows: The complete 2B6 cDNA is obtained by RT-PCR on human liver RNA (Clontech) using the following primers (SEQ ID NOS 21 and 22, respectively, in order of appearance);

5'ttcgatgatcaccaccatggaactcagcgtcctcctcttccttgcac3'

5'ttcgagccggctcatcagcggggcaggaagcggatctggtatgttg3'

This generates the complete 2B6 cDNA with an optimised kosak sequence flanked with unique Bcl1 and NgoM1 sites. This cDNA is then cloned into the Bcl1-NgoM1 site of pICUT-Hyg-Neo thus replacing Neo with p450 (see (A) below). Also shown below are the proviral DNA constructs in both transfected (B) and transduced (C) cells.

FIG. 15 is a sequence comparison of mutant env (m4070A) with wild type MMLV sequence from the 3' end of the pol gene.

FIG. 16 is the complete sequence of altered 4070A.

Figure 17:
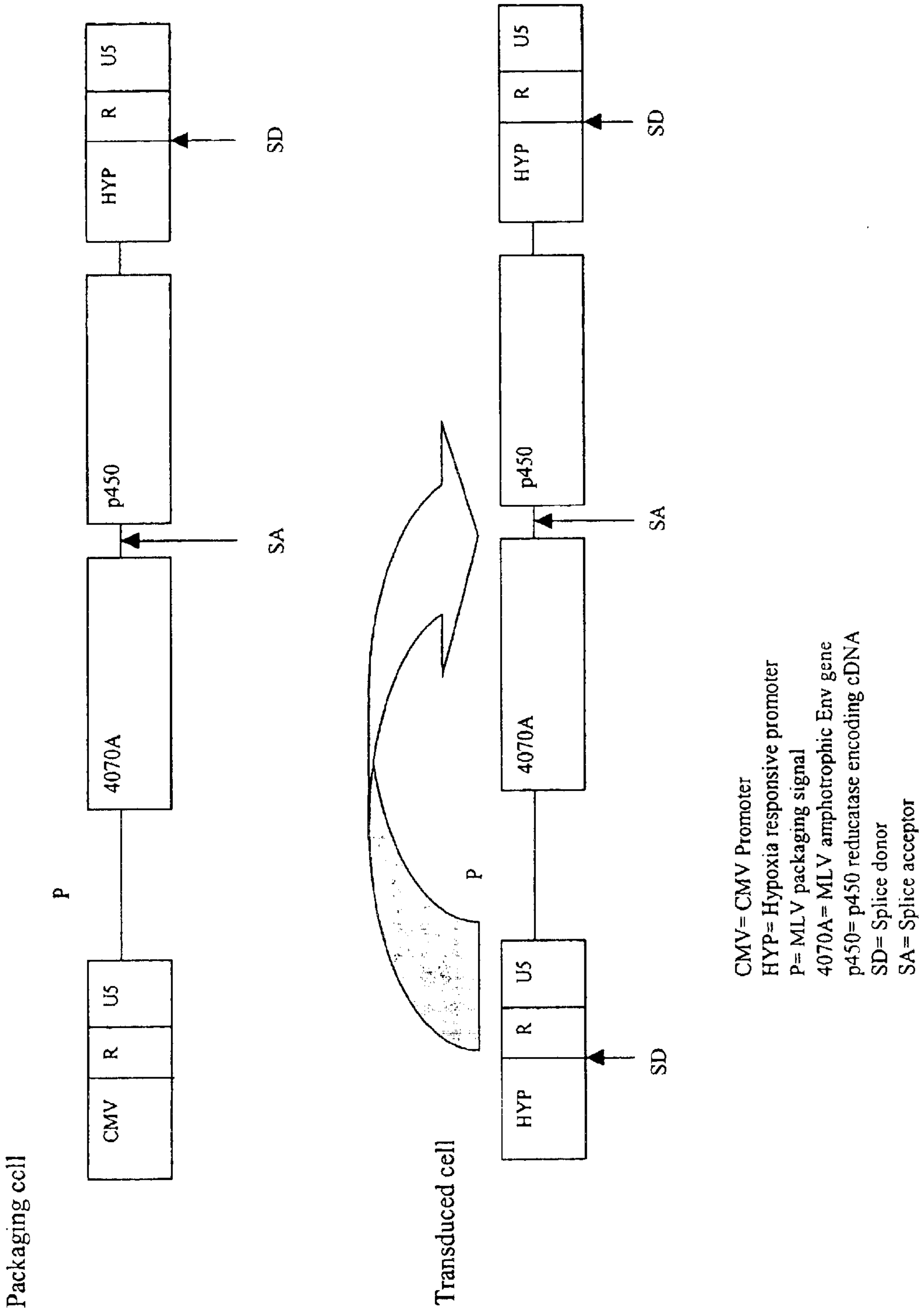

FIG. 17 shows a gene restricted expression retroviral vector whereby the first NOI (the 4070A envelope ORF) is expressed in the initial vector and the second NOI (in this instance p450) is expressed only after vector replication. After replication the 4070A gene is located within a functional intron and thus removed during RNA splicing.

Figure 18:
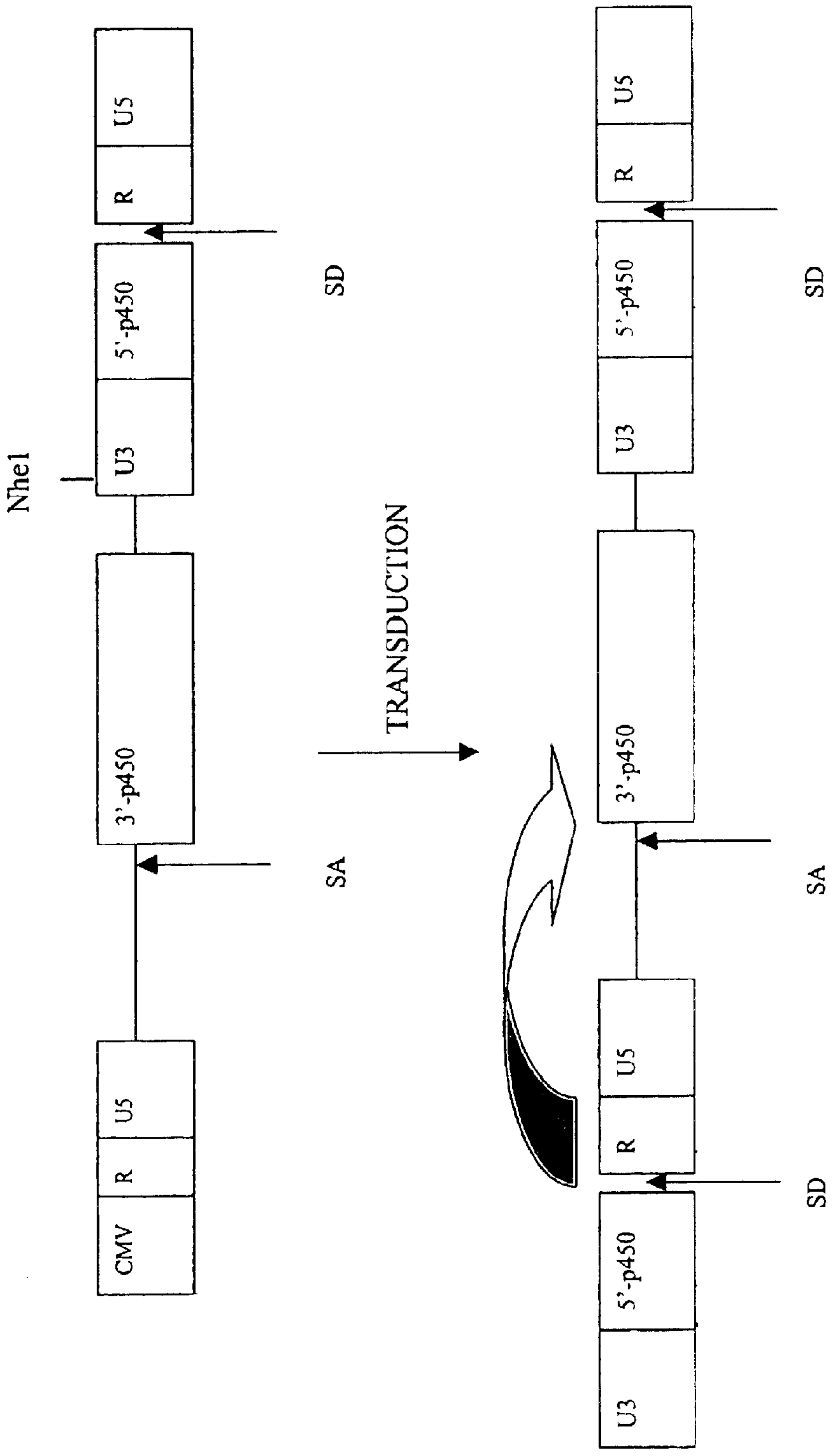

FIG. 18 shows a retroviral expression vector whereby the 5' end of the p450 gene (flush to a splice donor) is only found upstream of the 3' end of the p450 gene (flush to SA) after replication and thus only after replication is a functional p450 gene expressed (from spliced mRNA).

EXAMPLES

Example 1

Figure 2:
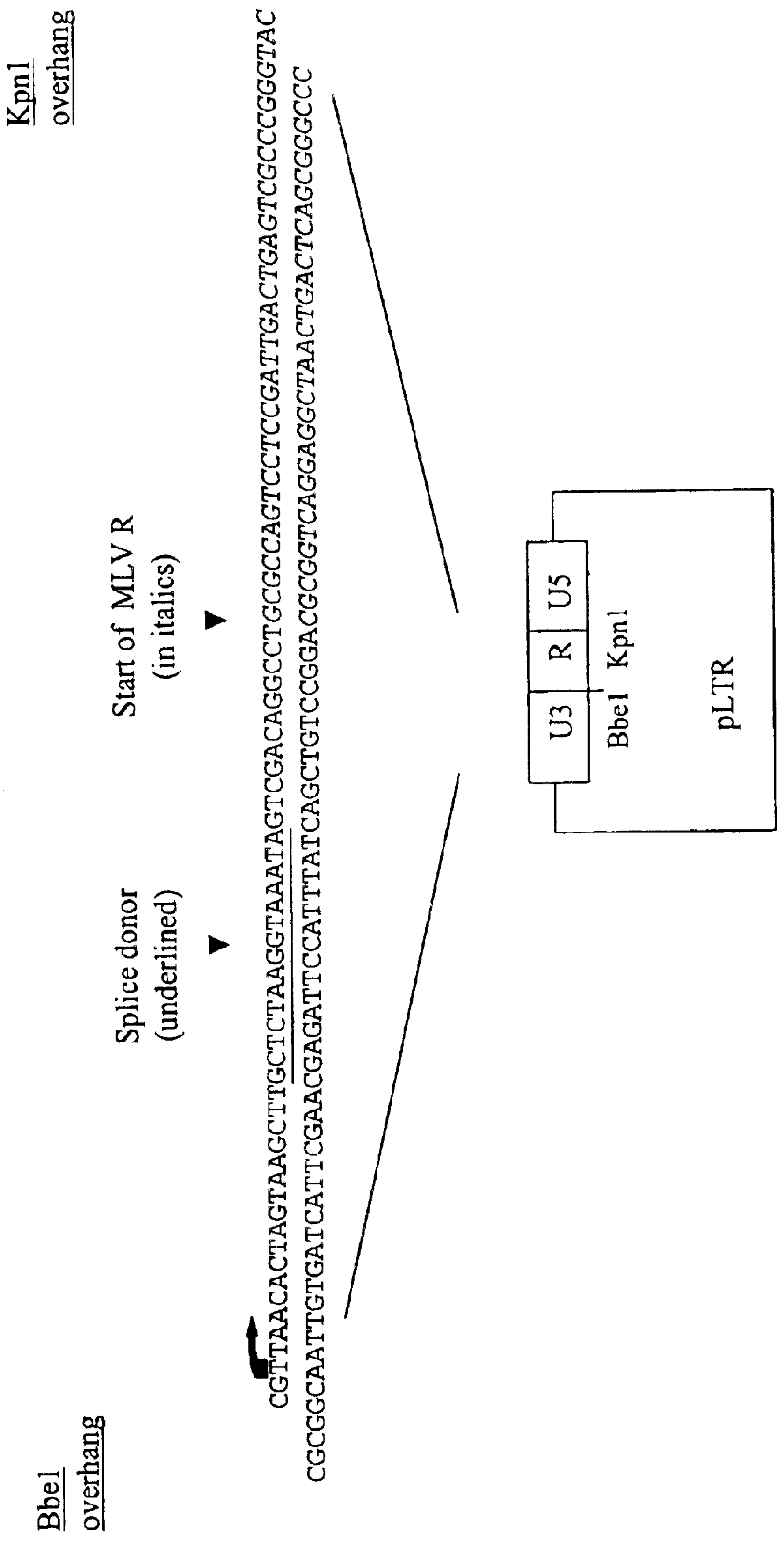

Construction of a Split-intron MLV Vector (i) Addition of Small-T Splice Donor:

The starting plasmid for this construct is pLXSN (Miller et al 1989 ibid); Firstly this construct is digested with Nhe1 and the backbone re-ligated to create an LTR (U3-R-U5) plasmid. Into this plasmid is then inserted an oligonucleotide containing the splice donor sequence between the Kpn1-Bbe1 sites. Also contained within this oligonucleotide, downstream of the splice donor is the MLV R sequence up to the Kpn1. The resulting plasmid is named 3'LTR-SD (see FIG. 2).

Figure 3:
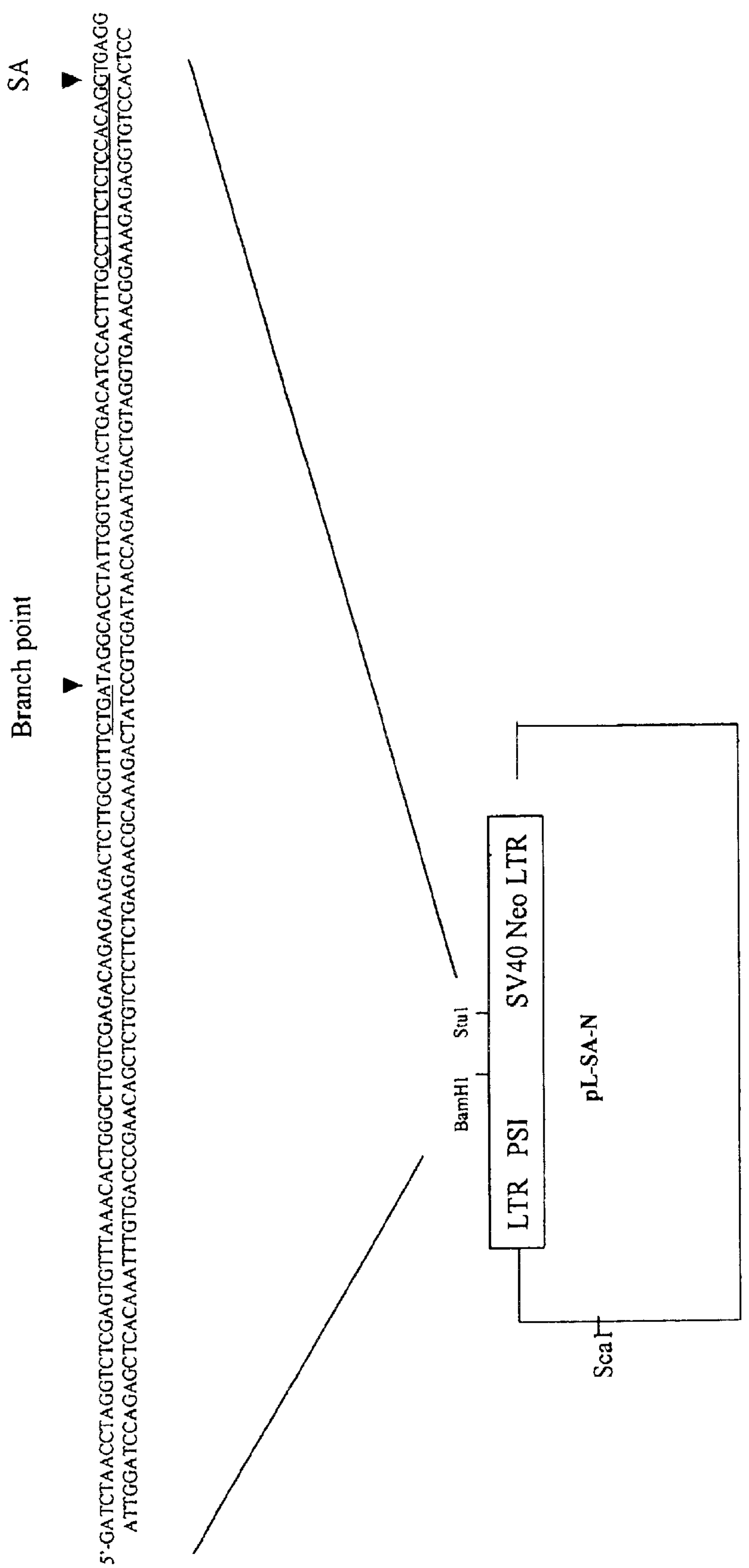

(ii) Addition of Splice Acceptor:

The splice acceptor sequence used in this construct (including the branch point- an A residue between 20 and 40 bases upstream of the splice acceptor involved in intron lariat formation (Aebi et al 1987 Trends in Genetics 3: 102–107) is derived from an immunoglobulin heavy chain variable region mRNA (Bothwell et al 1981 Cell 24: 625–637) but with a consensus/optimised acceptor site. Such a sequence signal is also present in pCI (Promega). This acceptor sequence is firstly inserted into the BamH1-Stu1 sites of pLXSN as double stranded oligonucleotide to create the vector pL-SA-N (note: SV40 promoter is lost from pLNSX during cloning). See FIG. 3 for an outline of the cloning strategy.

(iii) Removal of Original Splice Donor from pL-SA-N.

Figure 4:
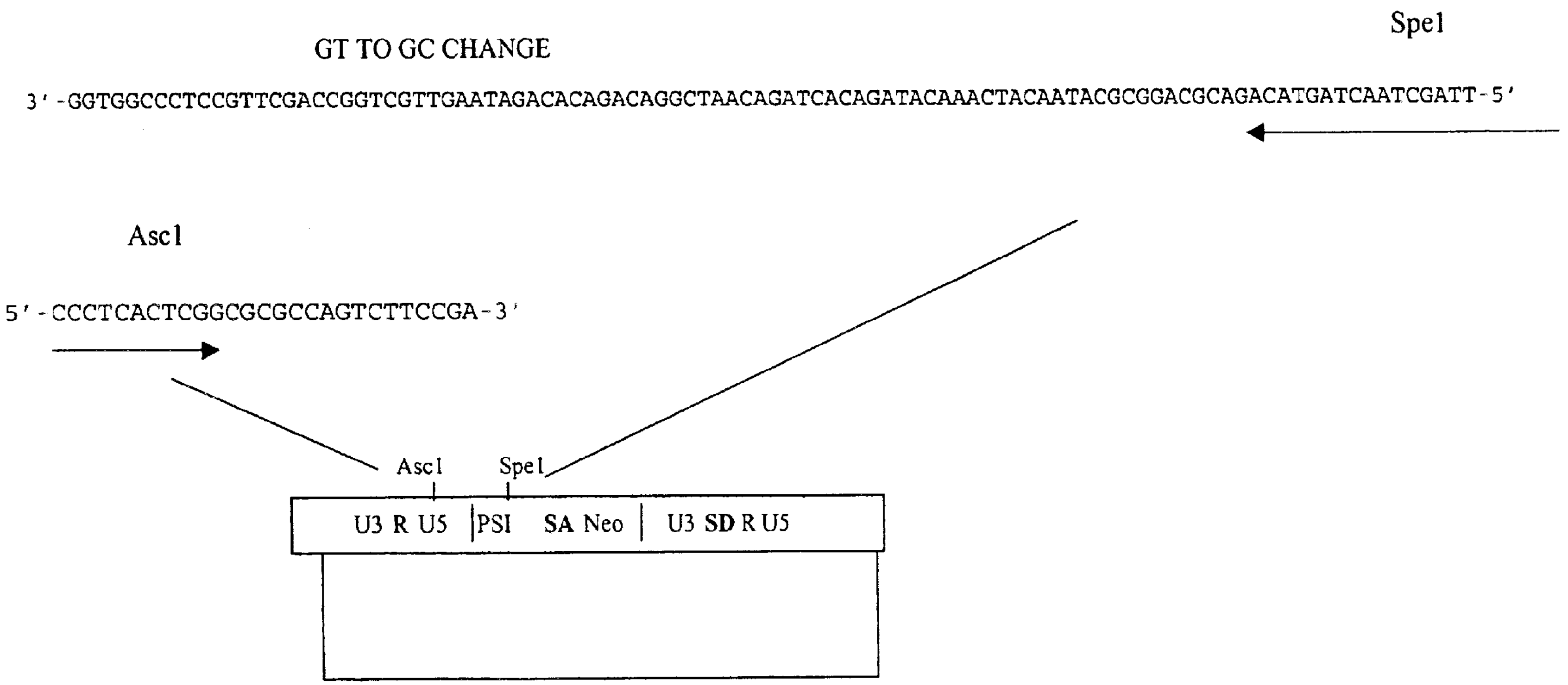

The removal of the splice donor contained within the gag sequence of pL-SA-N is achieved by PCR based site directed mutagenesis. Two oligonucleotides are used to PCR amplify the region spanning the Asc1 and Spe1 uniques sites of pL-SA-N. Also incorporated in the Spe1-spanning olgonucleotide is the agGTaag to agGCaag change also found in the splicing negative pBABE vectors (Morgenstern et al 1990 ibid). See FIG. 4 for cloning strategy outline.

(iv) Combining pL(noSD)-SA-N with 3'LTR-SD.

The pL(noSD)SA-N plasmid contains a normal MLV derived 3'LTR. This is replaced with the 3'LTR-SD sequence by taking the Nhe1 insert from pL(noSD)SA-N and dropping it into the Nhel digested 3'LTR-SD vector. The resulting plasmid, named pICUT (Intron Created Upon Transduction) contains all the features of this new generation of retroviral vector (see FIG. 5 for sequence data)

Example 2

Construction of a Split-intron Lentivector

Construction of Initial EIAV Lentiviral Expression Vector (also see patent application GB9727135.7)

Figure 1:
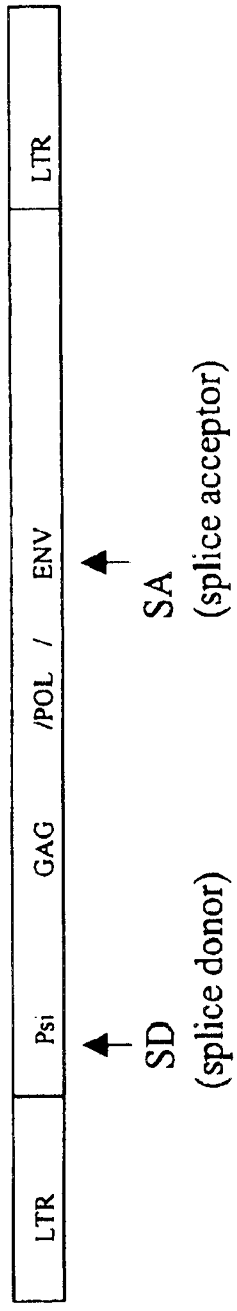

For the construction of a split-function lentiviral vector the starting point is the vector named pEGASUS-1 (see patent application GB 9727135.7). This vector is derived from infectious proviral EIAV clone pSPEIAV19 (accession number: U01866; Payne et al 1994). Its construction is outlined as follows: First; the EIAV LTR, amplified by PCR, is cloned into pBluescript II KS+ (Stratagene). The MluI/MluI (216/8124) fragment of pSEIAV19 is then inserted to generate a wild-type proviral clone (pONY2) in pBluescript II KS+ (FIG. 1). The env region is then deleted by removal of the Hind III/Hind III fragment to generate pONY2-H. In addition, a BglII/NcoI fragment within pol (1901/4949) is deleted and a β-galactosidase gene driven by the HCMV IE enhancer/promoter inserted in its place. This is designated pONY2.10nlsLacZ. To reduce EIAV sequence to 759 base pairs and to drive primary transcript off a CMV promoter: First; sequence encompassing the EIAV polypurine tract (PPT) and the 3'LTR are PCR amplified from pONY2.10LacZ using primers (SEQ ID NOS 18 and 19 respectively, in order of appearance):

PPTEIAV+ (Y8198): GACTACGACTAGTGTATGTTTAGAAAAACAAGG, and

3'NEGSpeI(Y8199): CTAGGCTACTAGTACTGTAGGATCTCGAACAG.

The PCR product is then cloned into the Spe1 site of pBS II KS$^+$; orientated such that U5 is proximal to Not1 in the pBlueScript II KS$^+$ Next, for the reporter gene cassette, a CMV promoter/LacZ from pONY 2.10nlsLacZ is removed by Pst1 digest and cloned into the Pst1 site of pBS.3'LTR orientated such that LacZ gene is proximal to the 3'LTR, this vector is named pBS CMVLacZ.3'LTR.

The 5'region of the EIAV vector is constructed in the expression vector pCIEneo which is derivative of pCIneo (Promega)-modified by the inclusion of approximately 400 base pairs derived from the 5'end of the full CMV promoter as defined previously. This 400 base pair fragment is obtained by PCR amplifcation using primers (SEQ ID NOS 20 and 6 respectively, in order of appearance):

VSAT1: (GGGCTATATGAGATGAATAATAAAATGTGT) and

VSAT2: (TATTAATAACTAGT) and pHIT60 (Soneoka et al 1995 Nucleic Acids Res 23: 628–633) as template. The product is digested with BglII and SpeI and cloned into the BglII/SpeI sites of pCIE-Neo.

A fragment of the EIAV genome running from the R region to nt 150 of the gag coding region (nt 268 to 675) is amplified from pSEIAV with primers:

CMV5'EIAV2 (SEQ ID NO: 7):

(ZO591)(GCTACGCAGAGCTCGTTTAGTGAACC GGGCACTCAGATTCTG: (sequences underlined anneals to the EIAV R region) and (SEQ ID NO: 8)

3'PSI. NEG (GCTGAGCTCTAGAGTCCTTTTCTTTT-ACAAAGTTGG).

The resulting PCR product is flanked by Xba1 and Sac1 sites. This is then cut and cloned into the pCIE-Neo Xba1-SacI sites. The resulting plasmid, termed pCIEneo5'EIAV now contains the start of the EIAV R region at the transcriptional start point of the CMV promoter. The CMVLacZ/3LTR cassette is then inserted into the pCIEneo5'EIAV plasmid by taking the Apa1 to Nor1 fragment from pBS.CMVLacZ.3LTR and cloning it into the Sal1-Not1 digested pCIEneo.5'EIAV (the Sal1 and Apa1 sites is T4 "polished" to create blunt the ends prior to the vector and insert respective Not1 digests). The resulting plasmid is named pEGASUS-1.

For use as a gene delivery vector pEGASUS-1 requires both gag/pol and env expression provided in trans by a packaging cell. For the source of gag/pol an EIAV gagpol expression plasmid (pONY3) is made by inserting the Mlu I/Mlu I fragment from pONY2-H into the mammalian expression plasmid pCI-neo (Promega) such that the gag-pol gene is expressed from the hCMV-MIE promoter-enhancer and contains no LTR sequences. For the source of env; the pRV583 VSV-G expression plasmid is routinely used. These three vectors are used in a three plasmid co-transfection as described for MLV-based vectors (Soneoka et al 1995 Nucl. Acids Res. 23:628–633) the resulting virus routinely titres at between $10^4$ and $10^5$ lacZ forming units per ml on D17 fibroblasts.

Construction of a EIAV Lentiviral Version Vector of pICUT; Named pEICUT

Figure 6:
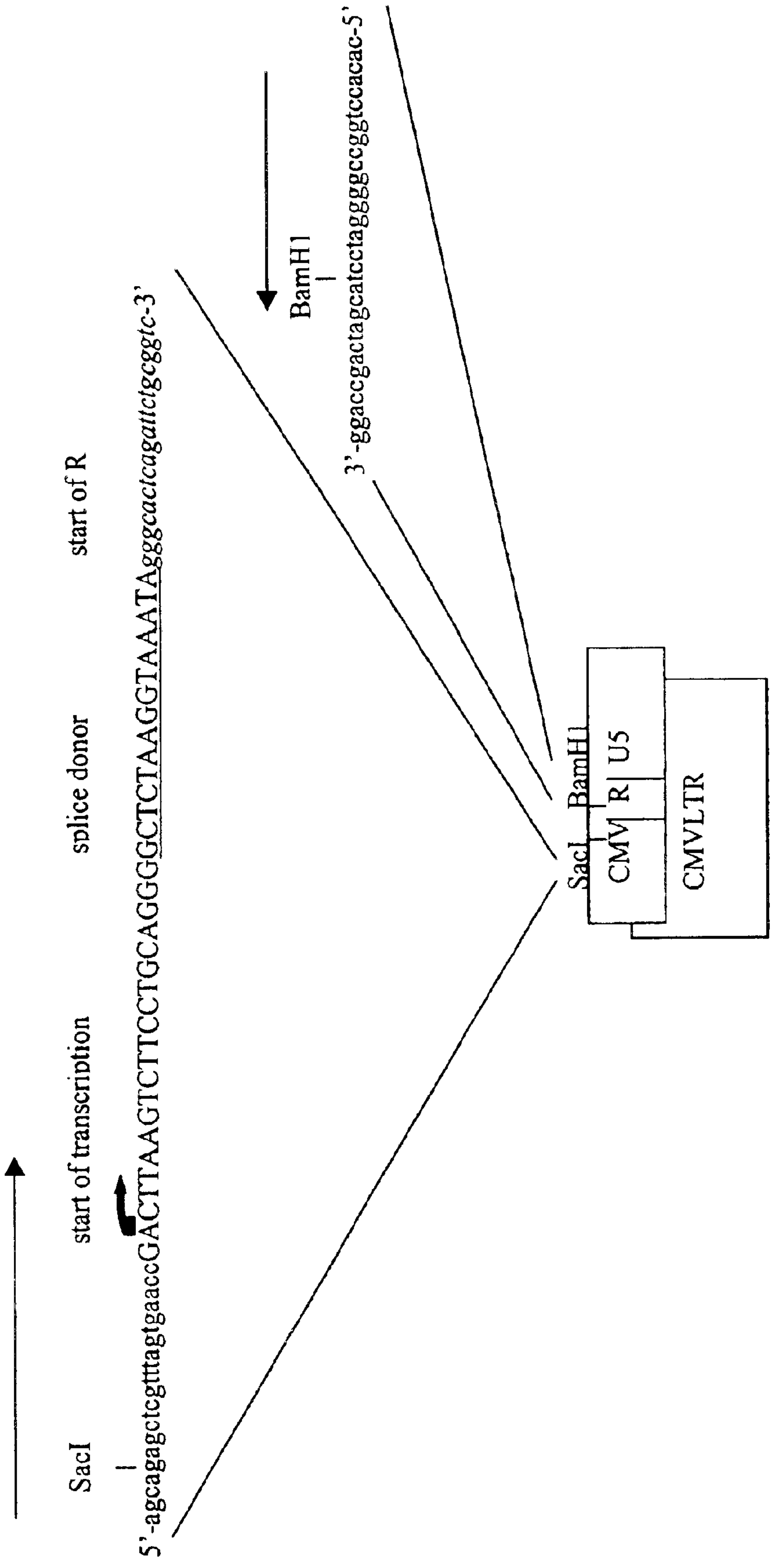
Figure 7:
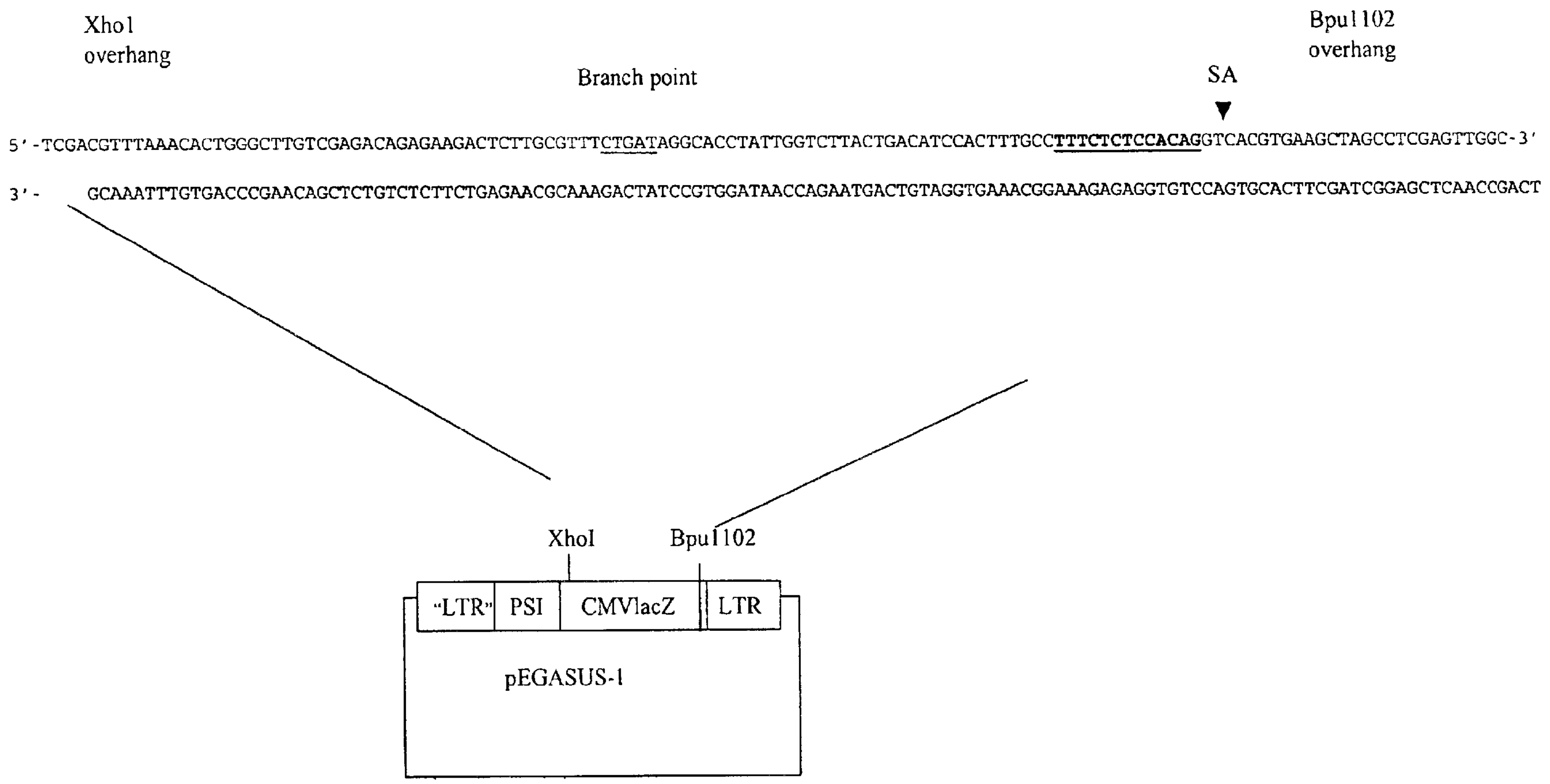
Figure 8:
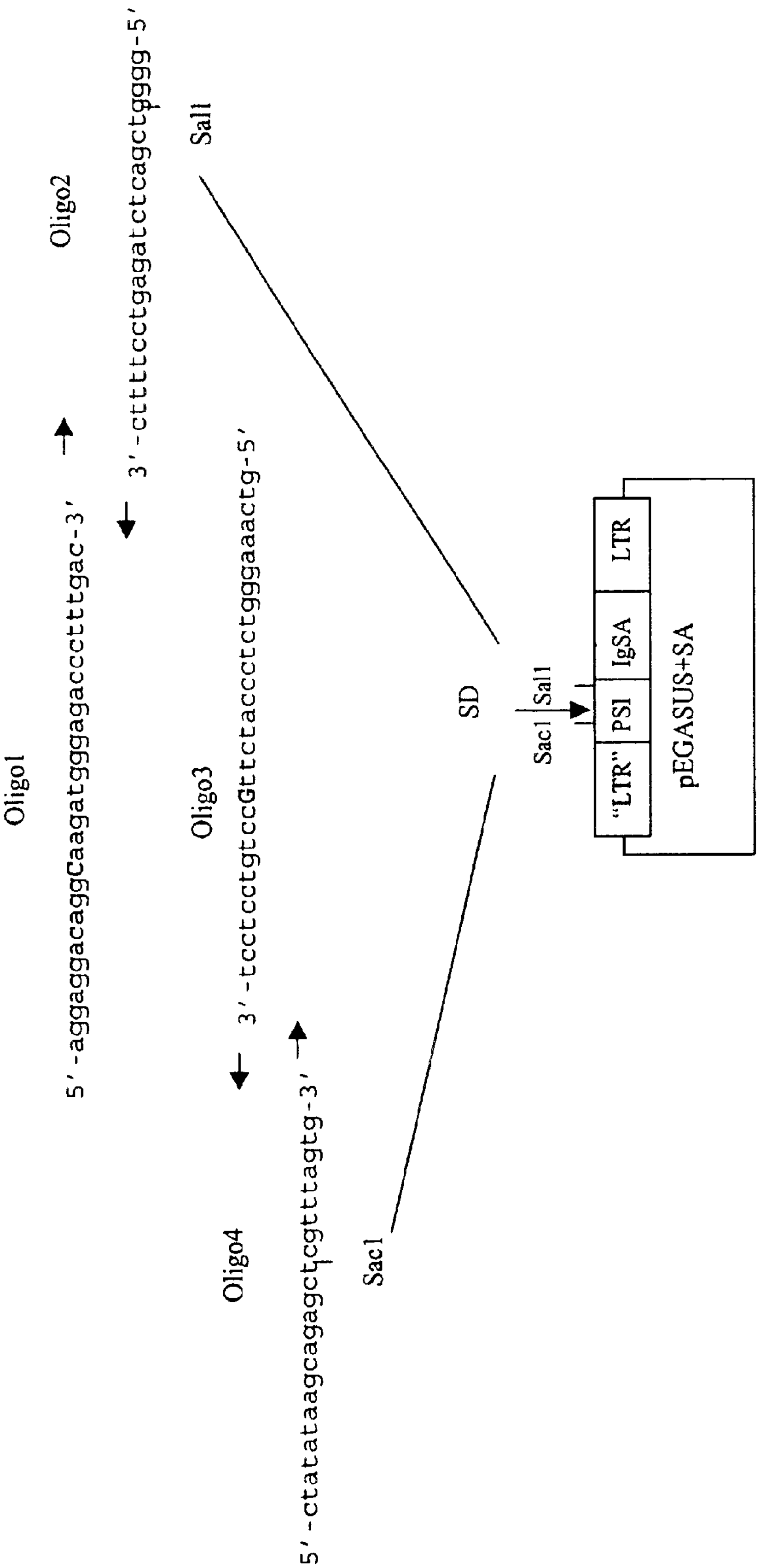
Figure 9:
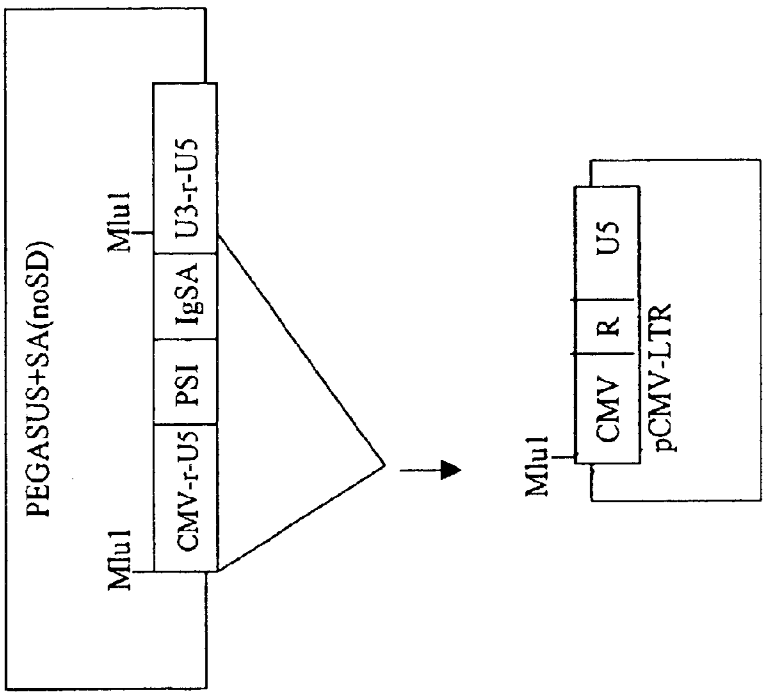
FIG. 9 shows a schematic diagram of combining pCMVLTR+SD with pEGASUS+SA(noSD) to create pEICUT-1. Here, one inserts the Mil1 fragment of pEGASUS+SA(noSD) into the unique Mil1 site of pCMV-LTR.
Figure 10:
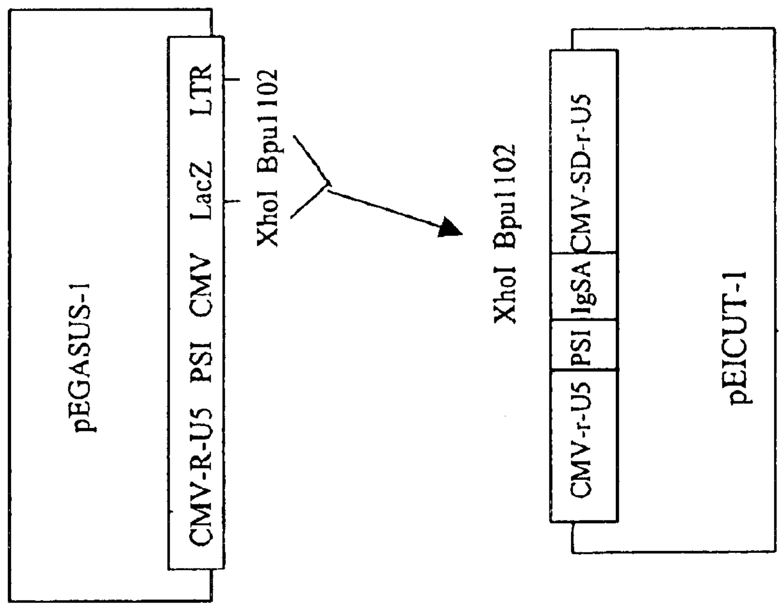
FIG. 10 shows a schematic diagram of the construction of pEICUT-LacZ. It is made by the insertion of the Xho1-Bpu1102 LacZ fragment from pEGASUS-1 and inserting it into the Xho1-Bpu1102 site of pEICUT-1 as outlined below.

To construct pEICUT firstly pEGASUS-1 the Xma1-SexA1 fragment is removed from pEGASUS-1 and the ends 'blunted' with T4 polymerase and plasmid re-ligated to create a plasmid containing only the CMV-R-U5 part of pEGASUS-1 which retains the SV40-Neo cassette in the backbone. This plasmid is named CMVLTR. To insert a splice donor at the CMV-R border PCR is carried out with the two oligonucleotides shown below in FIG. 6 and as outlined in the FIG. 6 legend. The resulting plasmid is named pCMVLTR+SD. The same immunoglobulin based consensus splice acceptor as for MLV pICUT (see earlier) is used in the EIAV version. This is inserted using oligonucleotides described in FIG. 7 into the XhoI-Bpu1102 site of pEGASUS-1 to create the plasmid pEGASUS+SA. The wild-type splice donor of EIAV is removed by carrying out overlapping PCR with the oligonulceotides and methodology as described in FIG. 8, using pEGASUS+SA as a template to generate the plasmid pEGASUS+SA(noSD). To then create pEICUT-1, the Mlu1-Mlu1 fragment from pEGASUS+SA(noSD) is then inserted into the unique Mlu1 site of pCMVLTR+SD to generate pEICUT-1 (see FIG. 9). LacZ can be then transferred from pEGASUS-1 into pEICUT-1 by Xho1-Bpu1102 digest and insertion to create pEICUT-Z (see FIG. 10; for sequence data see FIG. 11).

Both the MLV and EIAV pICUT vectors contain a strong splice acceptor upstream of the splice donor and therefore no functional intron (introns require splice donors positioned 5' of splice acceptors). For this reason, when the vector is transfected into producer cells the resulting transcripts generated will not be spliced. Thus the packaging signal will not be lost and as a consequence maximal packaging is achievable (see FIG. 12).

However because of the unique way by which retroviruses replicate, upon transduction, transcripts generated from the integrated pICUT vector will differ from those of transfected cells described above. This is because during replication the 3'U3 promoter (up to the 5'start of R) is copied and used as the 5' promoter in transduced cells. For this reason transcripts generated from integrated pICUT will now contain a strong splice donor 5' of a strong splice acceptor, both of which being located upstream of the neo ORF. Such transcripts will therefore contain a functional intron in the 5'UTR (untranslated region) and thus be maximally spliced and translated.

Another advantage of such vectors described above is that because the intron is created only upon transduction it is possible to limit gene expression to either packaged or transduced cells. One example of how this is achieved is outlined in FIGS. 13. The strategy entails the cloning of a second gene (in this example hygromycin) upstream of the splice acceptor. This is achieved by taking out the hygromycin cDNA on a SalI fragment from SelctaVector Hygro (Ingenius; Oxfordshire, UK), and cloning this into a Xho1 site (located upstream of the splice acceptor) of pICUT. This vector selectively expresses hygromycin in the transfected cells and neomycin in transduced cells. The reason for this is that in any one mRNA transcript only the first gene is translated by the ribsome without the aid of internal ribosome binding sites (IRESs). In the transfected cell this gene will be hygromycin. However in the transduced cells because the hygromycin open reading frame (ORF) is contained within a functional intron this gene will now be removed from mature mRNA transcripts thus allowing neo ORF translation.

Vectors with such cell specific gene expression maybe of clinical use for a variety of reasons; By way of example, expression of resistance markers can be restricted to producer cells-where they are required and not in transduced cells where they may be immunogenic. By way of another example, expression of toxic genes such as ricin and dominant negative signalling proteins could be restricted to transduced cells where they may be required to optionally arrest cell growth or kill cells but not in producer cells-where such features would prevent high titre virus production. FIG. 14 shows a Neo-p450 MLV pICUT construct such that only Neo is expressed in producer cells and the pro-drug p450 2B6 isoform expressed in transduced cells.

Another benefit of creating an intron upon transduction is that any essential elements required for vector function can now be placed inside a functional intron, which is created upon transduction, and be removed from transduced cell transcripts. By way of example, with both the MLV and the lentivector pICUT vectors, the viral transcript contained the functional Psi packaging signal (see Bender et al 1987 for the position of Psi in MLV; see patent application GB 9727135.7 for position of Psi in EIAV) within an intron which was created upon transduction and removed from the transduced cell transcripts.

The benefits from such an arrangement include:

(i) Enhanced translation from resulting transcripts because ribosomes may "stutter" in the presence of a Psi secondary structure- if present (Krall et al 1996 ibid and reference therein).

(ii) In the absence of the packaging signal, transcript packaging by endogenous retroviruses is prevented.

(iii) Unwanted premature translation initiation is prevented when viral essential elements such as gag (and other potential ATG translation start sites) are removed from the transcripts expressed in transduced cells. This is of particular benefit when packaging signals extend into gag as is the case for both the EIAV and MLV pICUT vectors.

(iv) Promoter, enhancers and suppressors may be placed within an intron created upon transduction thus mimicking other transcript arrangements like those generated from CMV that contain such entities within introns (Chapman et al 1991 ibid)

In summation the novel pICUT vector system described in the present invention facilitates the following arrangments:

(I) Maximal packaging and reduced translation of transcripts in producer cells.

(ii) Maximal splicing and therefore intron enhanced translation of transcripts in transduced cells (iii) Restriction of gene and/or viral essential element expression to either producer or transduced cells.

Example 3

Construction of an MMLV Amphotropic env Gene with Minimal Homology to the pol Gene and a gag-pol Transcription Cassette In the Moloney murine leukaemia virus (MMLV), the first approximately 60 bps of the env coding sequence overlap with sequences at the 3' end of the pol gene. The region of homology between these two genes was removed to prevent the possibility of recombination between them in cells expressing both genes.

The DNA sequence of the first 60 bps of the coding sequence of env was changed while retaining the amino acid sequence of the encoded protein as follows. A synthetic oligonucleotide was constructed to alter the codon usage of the 5'-end of env (See FIG. 15) and inserted into the remainder of env as follows.

The starting plasmid for re-construction of the 5' end of the 4070A gene was the pCI plasmid (Promega) into which had previously been cloned the xba1-Xba1 fragment containing the 4070A gene from pHIT456 (Soneoka et al 1995 ibid) to form pCI-4070A.

A PCR reaction was performed with primers A and B (FIG. 15) on pCI4070A to produce a 600 base pair product. This product was then cloned between the Nhe1 and Xho1 sites of pCI4070A. The resulting construct was sequenced across the Nhe1/Xho1 region. Although the amino acid sequence of the resulting gene is the same as the original 4070A, the region of homology with the pol gene is removed.

The complete sequence of the modified env gene m4070A is given in FIG. 16. This sequence is inserted into the expression vector pCI (Promega) by standard techniques.

The CMV gag-pol transcription unit is obtaind from pHIT60 (Soneoka et al 1995 ibid).

Example 4

Deletion of gag Sequences from the Retroviral Packaging Signal

A DNA fragment containing the LTR and minimal functional packaging signal is obtained from the retroviral vector MFG (Bandara et al 1993 Proc Natl Acad Sci 90: 10764–10768) or MMLV proviral DNA by PCR reaction using the following oligonucleotide primers:

HindIIIR(SEQ ID NO: 9) GCATTAAAGCTTTGCTCT

L523(SEQ ID NO: 10) GCCTCGAGCAAAAATTCAGACGGA

This PCR fragment contains MMLV nucleotides +1 to +523 and thus does not contain gag coding sequences which start at +621 (numbering based on the nucleotide sequence of MMLV Shinnick et al 1981 Nature 293: 543–548).

The PCR fragment can be used to construct a retroviral genome vector by digestion using HindIII and Xho1 restriction enzymes and sub-cloning using standard techniques. Such vectors contain no homology with gag coding sequences.

Example 5

Construction of Defective Retroviral Genome

The transcription unit capable of producing a defective retroviral genome is shown in FIG. 17. It contains the following elements: a hypoxia regulated promoter enhancer comprising 3 copies of the PGK—gene HRE and a SV40 promoter deleted of the 72bp-repeat enhancer from pGL3 (Promega); a MMLV sequence containing R, U5 and the packaging signal; the coding sequence of m4070A (Example 3); a splice acceptor; a cloning site for insertion of a coding sequence for a therapeutic protein; the polypyrimidine tract from MMLV; a second copy of the HRE-containing promoter-enhancer; a splice donor site; and a second copy of R, U5.

On reverse transcription and integration of the vector into the secondary target cell, the splice donor is introduced upstream of the env gene causing it to be removed from mRNA by splicing and thereby permitting efficient expression of the therapeutic gene only in the secondary target cell (See FIG. 17).

Example 6

Construction of a Conditional Expression Vector for Cytochrome P450

FIG. 18 shows the structure of retroviral expression vector cDNA coding sequences from the cytochrome P450 gene in two halves such that only upon transduction is the correct splicing achieved to allow P450 expression. This therefore restricts expression to transduced cells.

1) The starting plasmid for the construction of this vector is pLNSX (Miller and Rosman 1989 BioTechniques 7: 980–990). The natural splice donor ( . . . agGTaag . . . ) contained within the packaging signal of pLNSX (position 781/782) is mutated by PCR mutagenesis using the ALTERED SITES II mutageneisis kit (Promega) and a synthetic oligonucleotide of the sequencer(SEQ ID NO: 11):

5'-caaccaccgggagGCaagctggccagcaacuta-3'

2) A CMV promoter from the pCI expression vector (Promega) is isolated by PCR using the following two oligonucleotides:

Primer 1(SEQ ID NO: 12): 5'-atcggctagcagatcttcaatattggccattagccatat-3'

Primer 2(SEQ ID NO: 13): 5'-atcgagatctgcggccgcttacctgcccagtgcctcacgaccaa-3'

This produces a fragment containing the CMV promoter with a 5'Nhe1 site (Primer 1) and a 3'Not1 and Xba1 site (Primer 2). It is cut with Nhe1 and Xba1 and cloned into pLNSX from which an Nhe1-Nhe1 fragment has been removed.

3) The 5' end of a cytochrome P450 cDNA coding sequence is isolated by RT-PCR from human liver RNA (Clontech) with the following primers:

Primer 3(SEQ ID NO: 14): 5'-atcggcggccgcccaccatggaactcagcgtcctcctcttccttgcaccctagg-3'

Primer 4(SEQ ID NO: 15): 5'-atcggcggccgcacttacCtgtgtgccccaggaaagtatttcaagaagccag-3'

This amplifies the 5' end of the p450 from the ATG to residue 693 (numbering from the translation initiation site Yamano et al 1989 Biochem 28:7340–7348). Contained on the 5' end of the fragment (derived from Primer 3) is also a Not1 site and an optimised "Kozak" translation initiation signal. Contained on the 3' end of the sequence (derived from primer 4) is another Not1 site and a consensus splice donor sequence (also found in pCI and originally derived from the human beta globin gene) with the GT splice donor pair located flush against residue 704 of P450 (the complementary residue is shown in uppercase in Primer 4). This fragment is digested with Not1 and cloned into the Not1 digested plasmid generated in step 2.

The Nhe1-Nhe1 fragment removed during the cloning of step 2 is then re-introduced into the plasmid of step 3. This creates a retroviral vector as described in FIG. 17 but missing the 3' end P450.

The 3'of the P450 coding sequence is isolated by RT-PCR amplification from human liver RNA (Clontech) using the following primers:

Primer 5(SEQ ID NO: 16): actgtgatcataggcacctattggtcttactgacatccactttctctccacagGcaagtttacaaaacctgcaggaaatcaatgcttacatt-3'

Primer 6(SEQ ID NO: 17): actgatcgamccctcagccccttcagcggggcaggaagc-3'

This generates the PCR amplified 3' end of P450 from residue 705 (in uppercase primer 5) and extends past the translation termination codon. Contained within the 5' end of this product and generated by primer 5 is a Bcl1 restriction site and a consensus splice acceptor and branch point (also found in pCI and originally from an immunoglobulin gene) upstream of residue 705. Contained at the 3' end of this product downstream of the stop codon and generated by primer 6 is a Cla1 site. This PCR product is then digested with Bcl1 and Cla1 and cloned into the vector of step 3 with the Bcl1-Cla1 fragment removed to generate the retroviral vector as shown in FIG. 18.

The following examples describe the construction of an adenolentiviral system that can be used for the transient production of lentivirus in vitro or in vivo.

First Generation Recombinant Adenovirus

The first generation adenovirus vectors consist of a deletion of the E1 and E3 regions of the virus allowing insertion of foreign DNA, usually into the left arm of the virus adjacent to the left Inverted Terminal Repeat (ITR). The viral packaging signal (194–358 nt) overlaps with the E1 a enhancer and hence is present in most E1 deleted vectors. This sequence can be translocated to the right end of the viral genome (Hearing & Shenk,1983 Cell 33: 59–74). Therefore, in an E1 deleted vector 3.2 kb can be deleted (358–3525 nt).

Adenovirus is able to package 105% length of the genome, thus allowing for addition of an extra 2.1 kb. Therefore, in an E1/E3 deleted viral vector the cloning capacity becomes 7–8 kb (2.1 kb+1.9 kb (removal of E3)+3.2 kb (removal of E1). Since the recombinant adenovirus lacks the essential E1 early gene it is unable to replicate in non-E1 complementing cell lines. The 293 cell line was developed by Graham et al. (1977 J Gen Virol 36: 59–74) and contains approximately 4 kb from the left end of the Ad5 genome including the ITR, packaging signal, E1a, E1b and pIX. The cells stably express E1a and E1b gene products, but not the late protein IX, even though pIX sequences are within E1b. In non-complementing cells the E1 deleted virus transduces the cell and is transported to the nucleus but there is no expression from the E1 deleted genome.

First Generation Adenovirus Production System

Microbix Biosystems—nbl Gene Sciences

Figure 19:
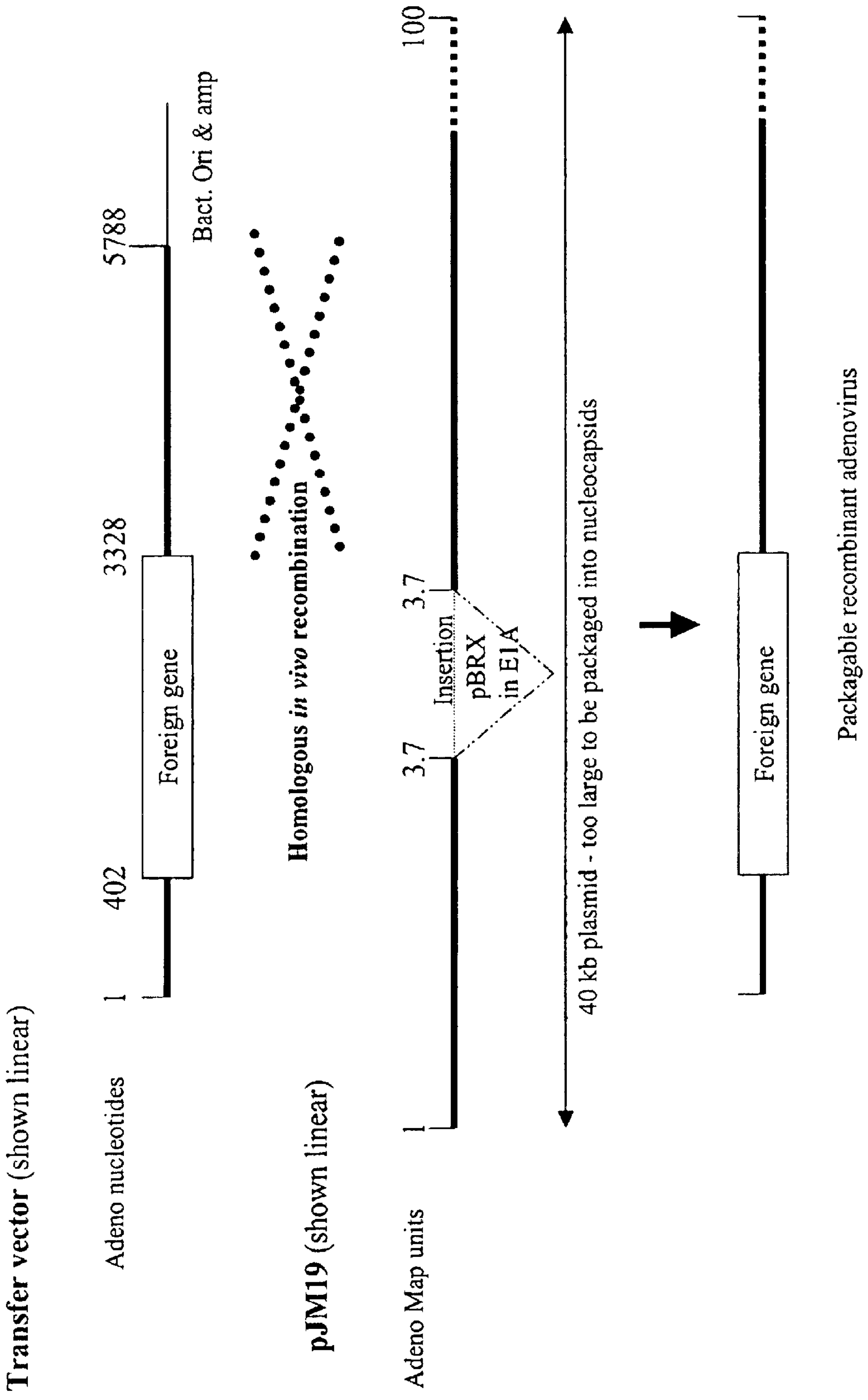

The diagram in FIG. 19 shows the general strategy used to create recombinant adenoviruses using the microbix system The general strategy involves cloning the foreign DNA into an E1 shuttle vector, where the E1 region from 402–3328 bp is replaced by the foreign DNA cassette. The recombinant plasmid is then co-transfected into 293 cells with the pJM17 plasmid. pJM17 contains a deletion of the E3 region and an insertion of the prokaryotic pBRX vector (including the ampicillin resistance and bacterial ori sequences) into the E1 region at 3.7 map units. This 40 kb plasmid is therefore too large to be packaged into adeno nucleocapsids but can be propagated in bacteria Intracellular recombination in 293 cells results in replacement of the $amp^r$ and ori sequences with the insert of foreign DNA.

Example 7

Construction of Transfer Plasmids for the Creation of Adenoviruses Containing EIAV Components In order to produce lentiviral vectors four adenovirus need to be made: genome, gagpol, envelope (rabies G) and Rev. The lentiviral components are expressed from heterologous promoters they contain introns where needed (for high expression of gagpol, Rev and Rabies envelope) and a polyadenylation signal. When these four viruses are transduced into E1a minus cells the adenoviral components will not be expressed but the heterlogous promoters will allow the expression of the lentiviral components. An example is outlined below (example 1) of the construction of an EIAV adenoviral system (Application number: 9727135.7). The EIAV is based on a minimal system that is one lacking any of the non-essential EIAV encoded proteins (S2, Tat or envelope). The envelope used to pseudotype the EIAV is the rabies envelope (G protein). This has been shown to pseudotype EIAV well (Application number. 9811152.9).

Transfer Plasmids

Figure 20:
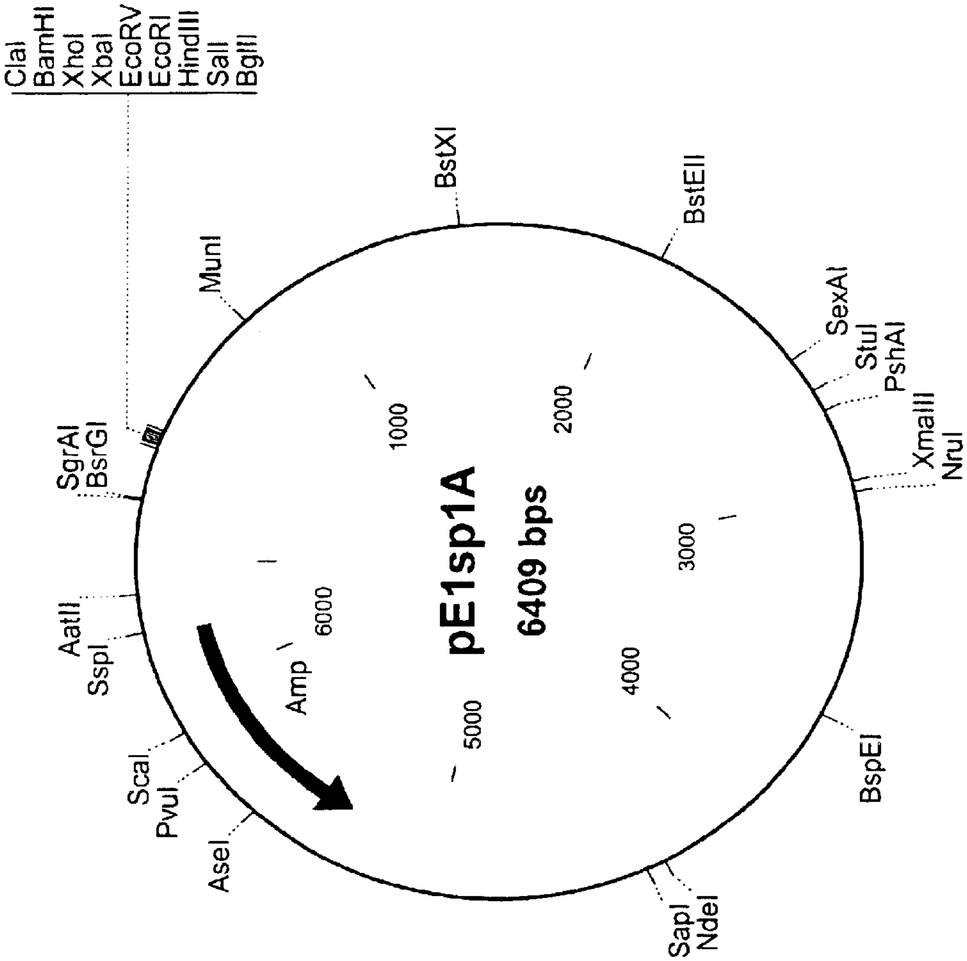

Decribed below is the construction of the transfer plasmids containing the EIAV components. The transfer plamsid is pE1sp1A (FIG. 20).

The recombinant transfer plamsids can the be used to make recombinant adenoviruses by homologous recombination in 293 cells.

A pictorial representation of the following plasmids is attached.

A) pE1RevE—Rev Construct

Figure 21:
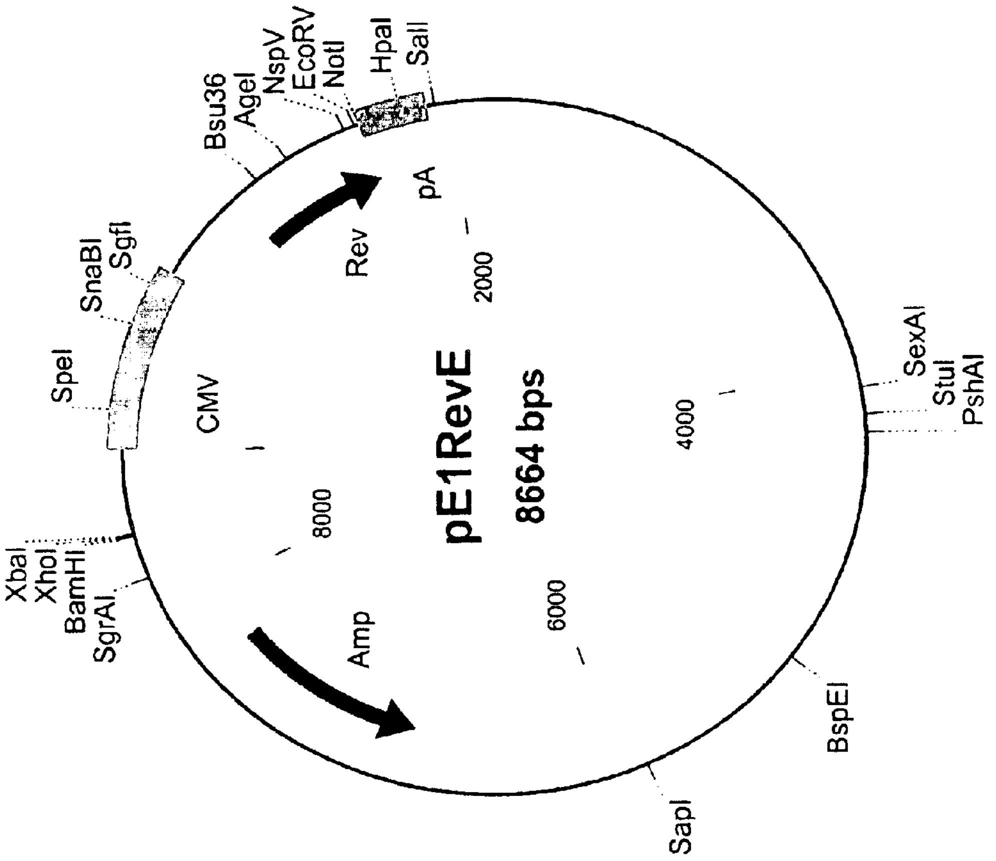

The plasmid pCI-Rev is cut with Apa LI and Cla I. The 2.3 kb band encoding EIAV Rev is blunt ended with Klenow polymerase and inserted into the Eco RV site of pE1 sp1A to give plasmid pE1RevE (FIG. 21).

Figure 22:
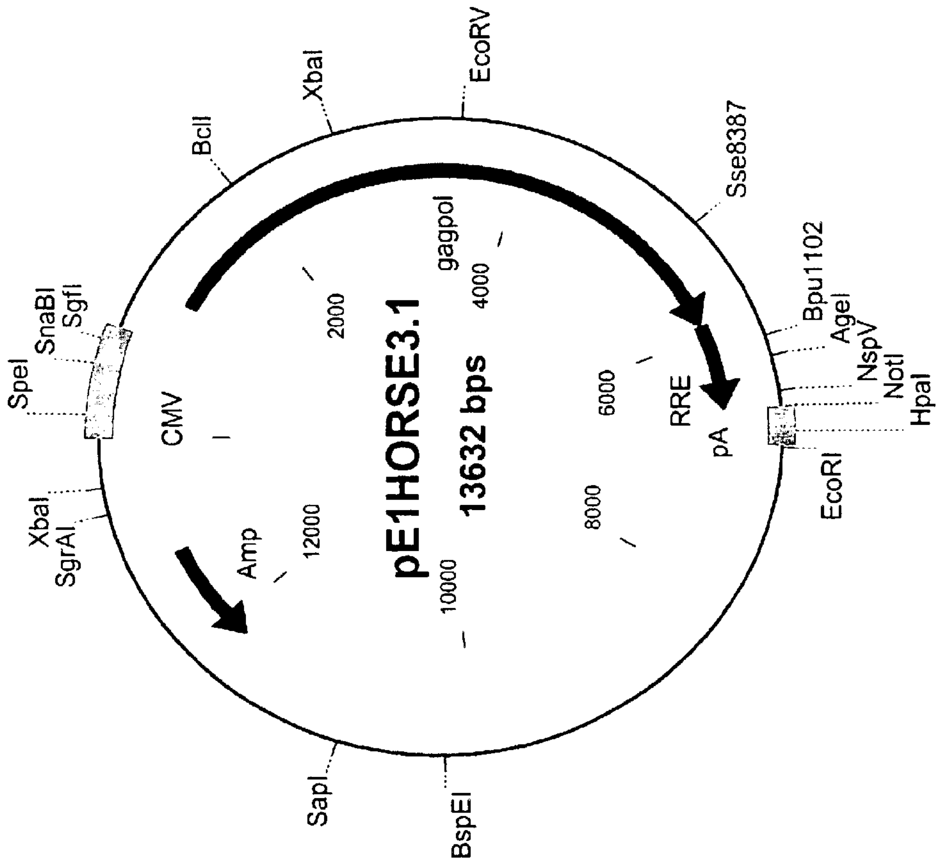

B) pE1HORSE3.1—gagpol Construct pHORSE3.1 was cut with Sna BI and Not I. The 6.1 kb band encoding EIAV gagol was inserted into pE1RevE cut with Sna BI and Not I (7.5 kb band was purified). This gives plasmid pE1HORSE3.1 (FIG. 22).

Figure 23:
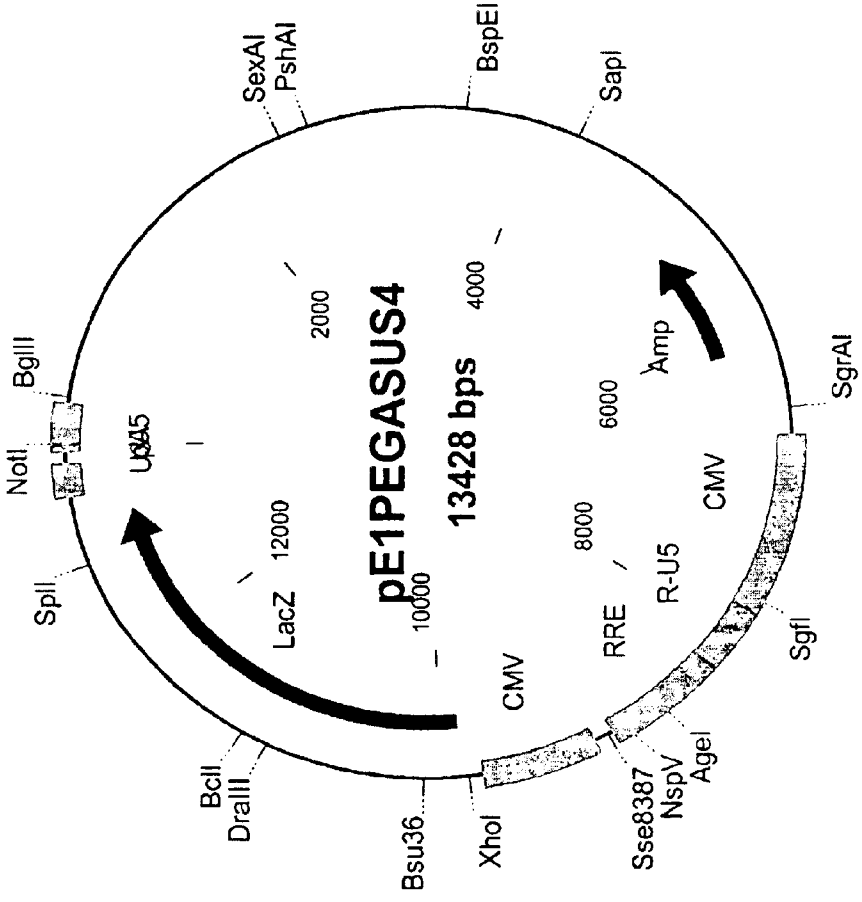

C) pE1PEGASUS—Genome Construct pEGASUS4 was cut with Bgl II and Not I. The 6.8 kb band containing the EIAV vector genome was inserted into pE1RevE cut with Bgl II and Not I (6.7 kb band was purified). This gave plasmid pE1PEGASUS (FIG. 23).

D) pCI-Rab—Rabies Construct

Figure 24:
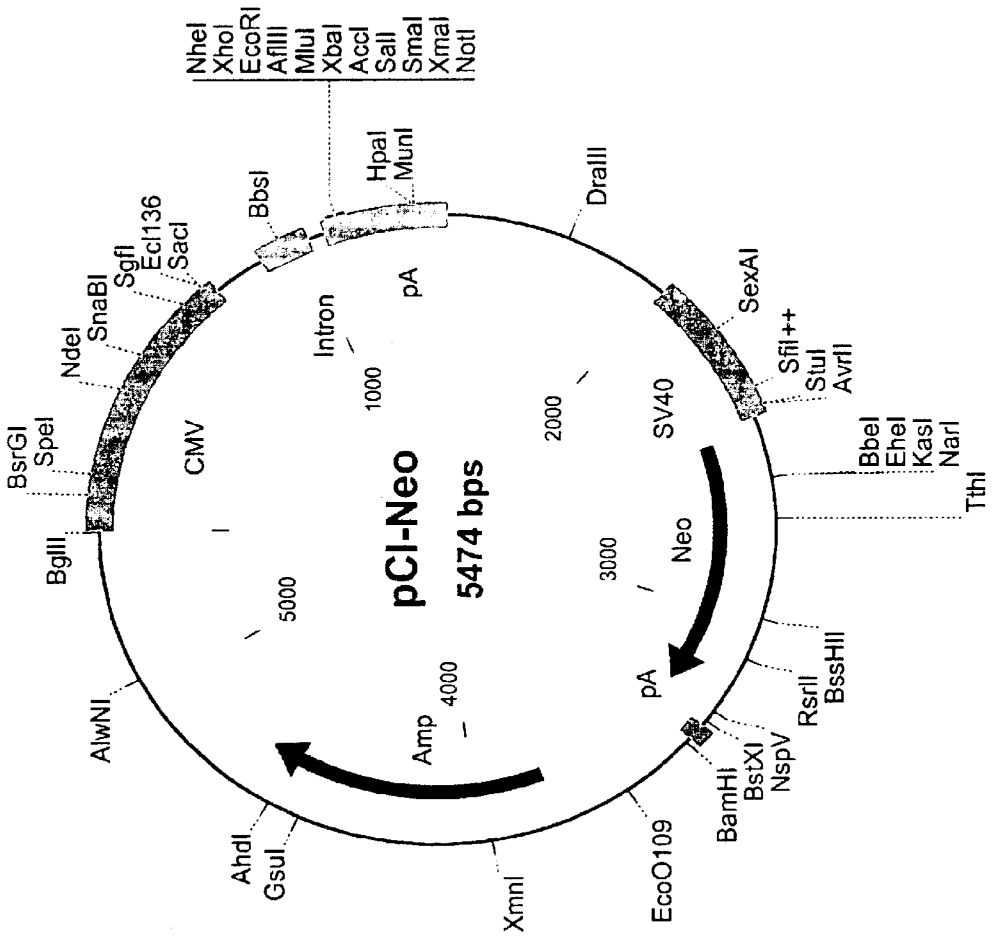
Figure 25:
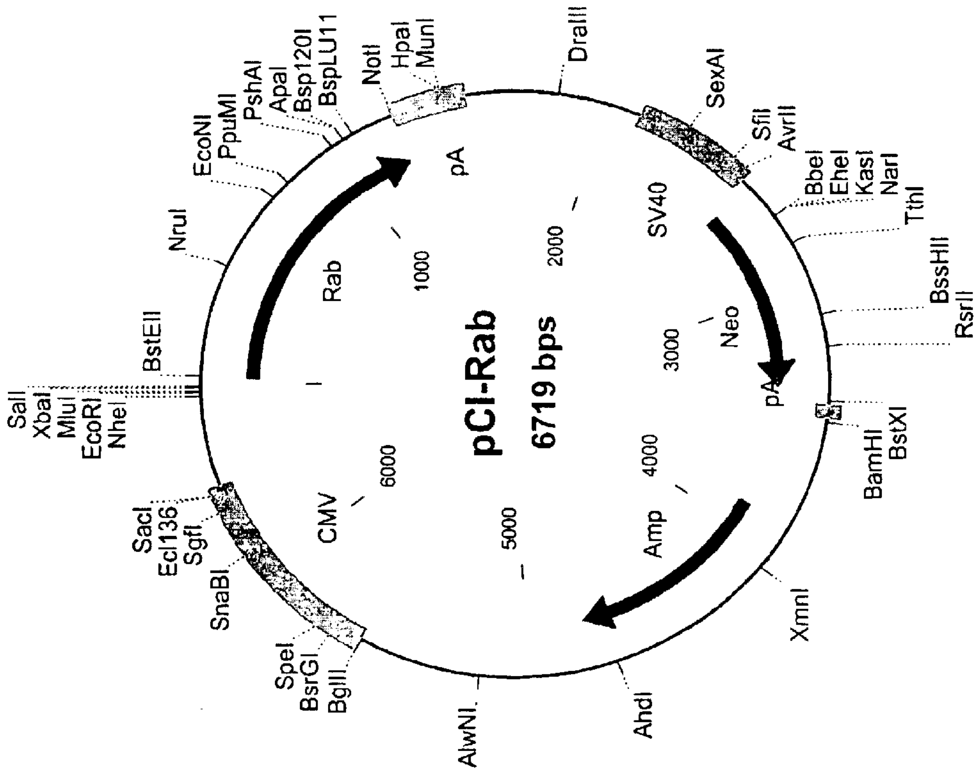

In order to make pE1Rab the rabies open reading frame was inserted into pCI-Neo (FIG. 24) by cutting plasmid pSA91RbG with Nsi I and Ahd I. The 1.25 kb band was bluntended with T4 DNA polymerase and inserted into pCI-Neo cut with Sma I. This gave plasmid pCI-Rab (FIG. 25).

Figure 26:
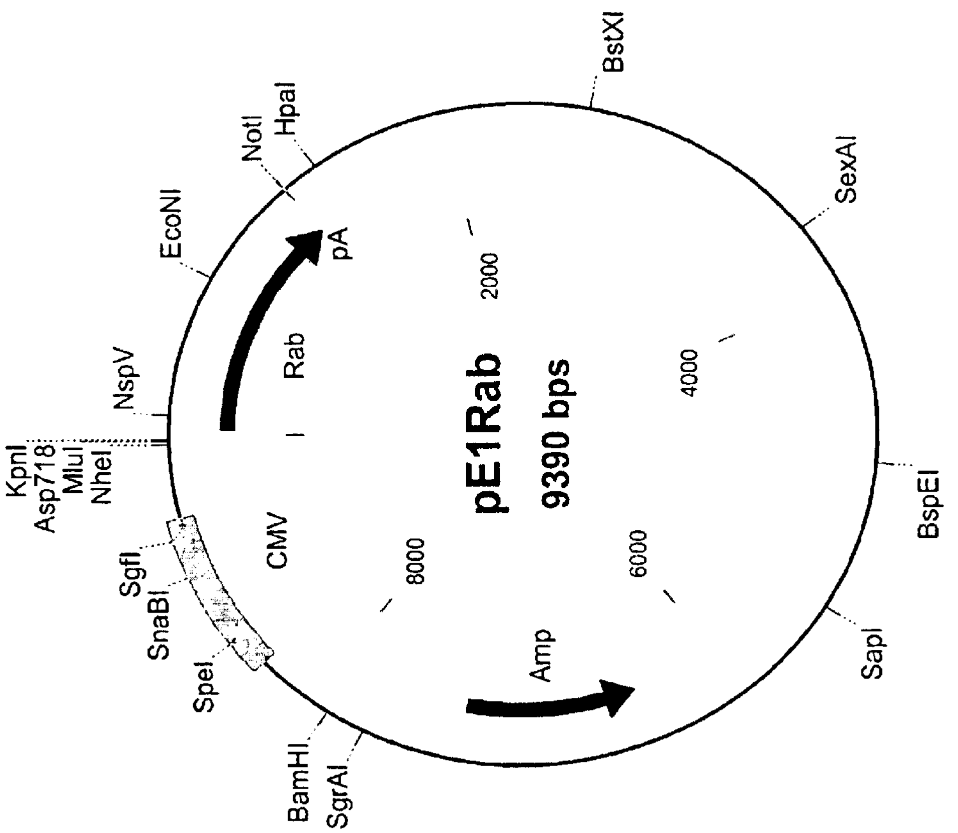

F) pE1Rab—Rabies construct pCI-Rab was cut with Sna BI and Not I. The 1.9 b band encoding Rabies envelope was inserted into pE1RevE cut with Sna BI and Not I (7.5 b band was purified). This gave plasmid pE1Rab (FIG. 26).

SUMMARY

The present invention relates to a novel delivery system suitable for introducing one or more NOIs into a target cell.

In one preferred aspect the present invention covers a retroviral vector comprising a functional splice donor site and a functional splice acceptor site; wherein the functional splice donor site and the functional splice acceptor site flank a first nucleotide sequence of interest ("NOI"); wherein the functional splice donor site is upstream of the functional splice acceptor site; wherein the retroviral vector is derived from a retroviral pro-vector; wherein the retroviral pro-vector comprises a first nucleotide sequence ("NS") capable of yielding the functional splice donor site and a second NS capable of yielding the functional splice acceptor site; wherein the first NS is downstream of the second NS; such that the retroviral vector is formed as a result of reverse transcription of the retroviral pro-vector.

Alternatively expressed, this aspect covers a novel delivery system which comprises one or more NOIs flanked by a functional SD and SA provided that this has been generated from a pro-vector in which the order of the SD and SA is reversed to render the splicing non-functional.

Figure 27A:
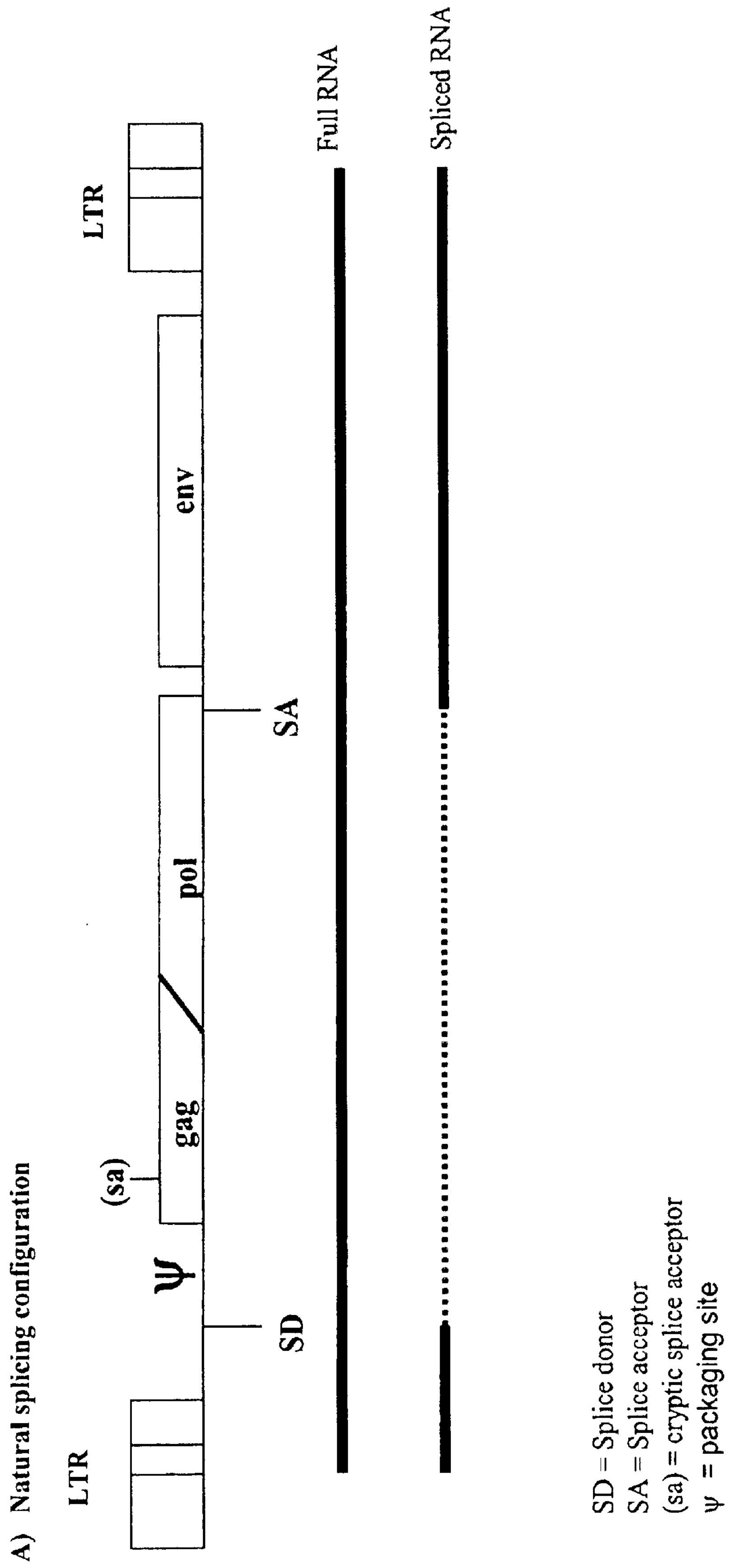
Figure 27B:
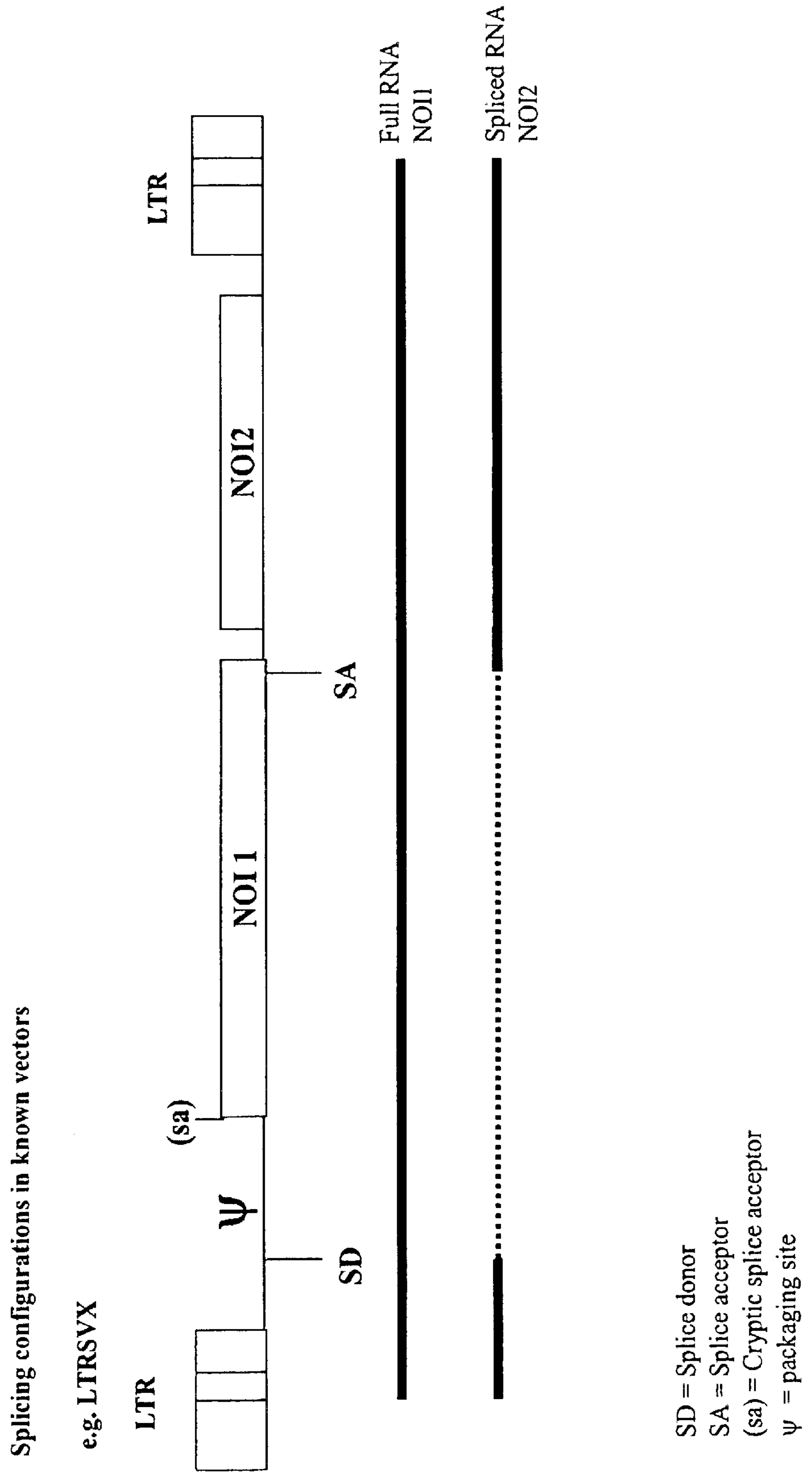
Figure 27B:
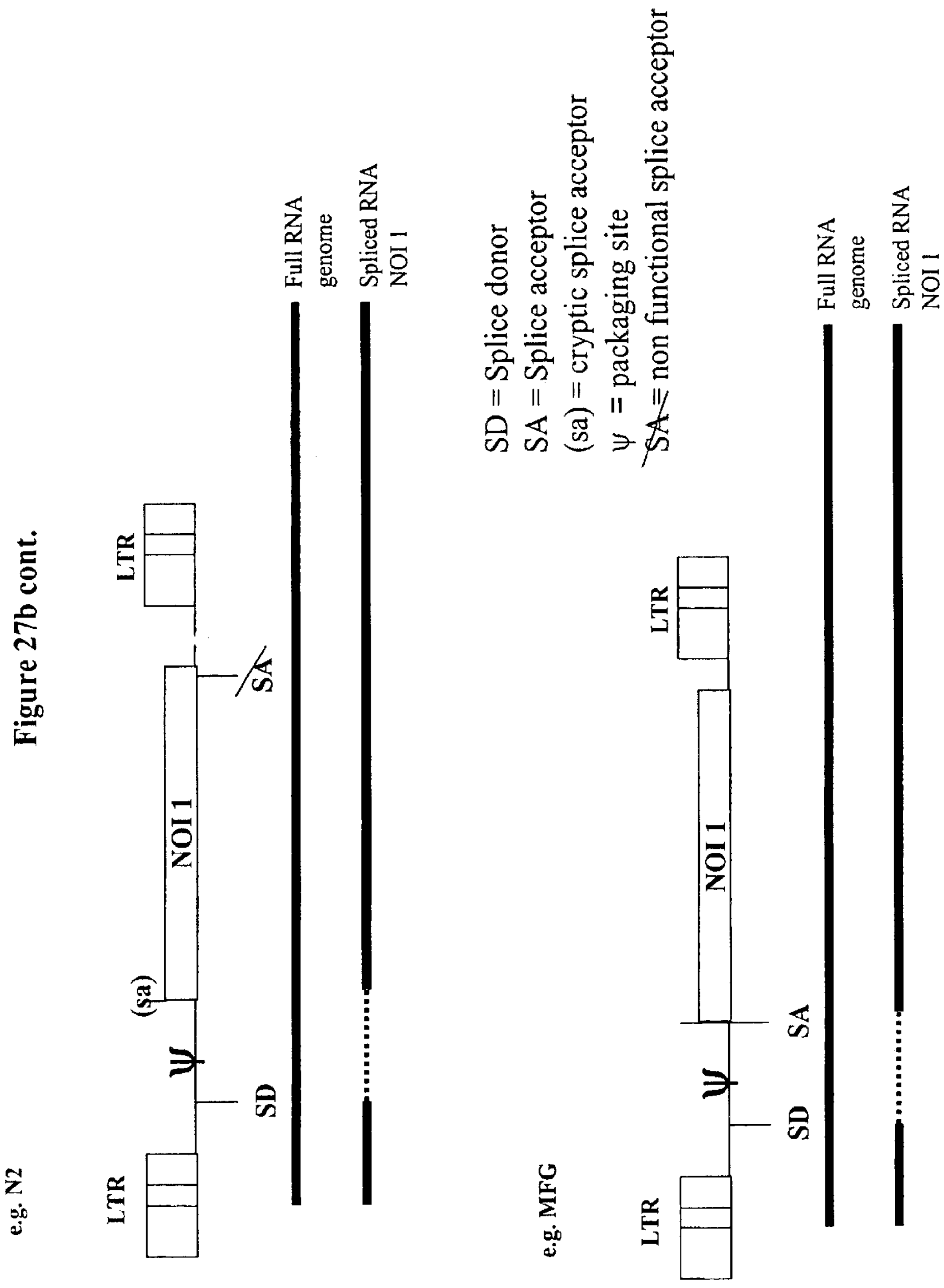
Figure 27B:
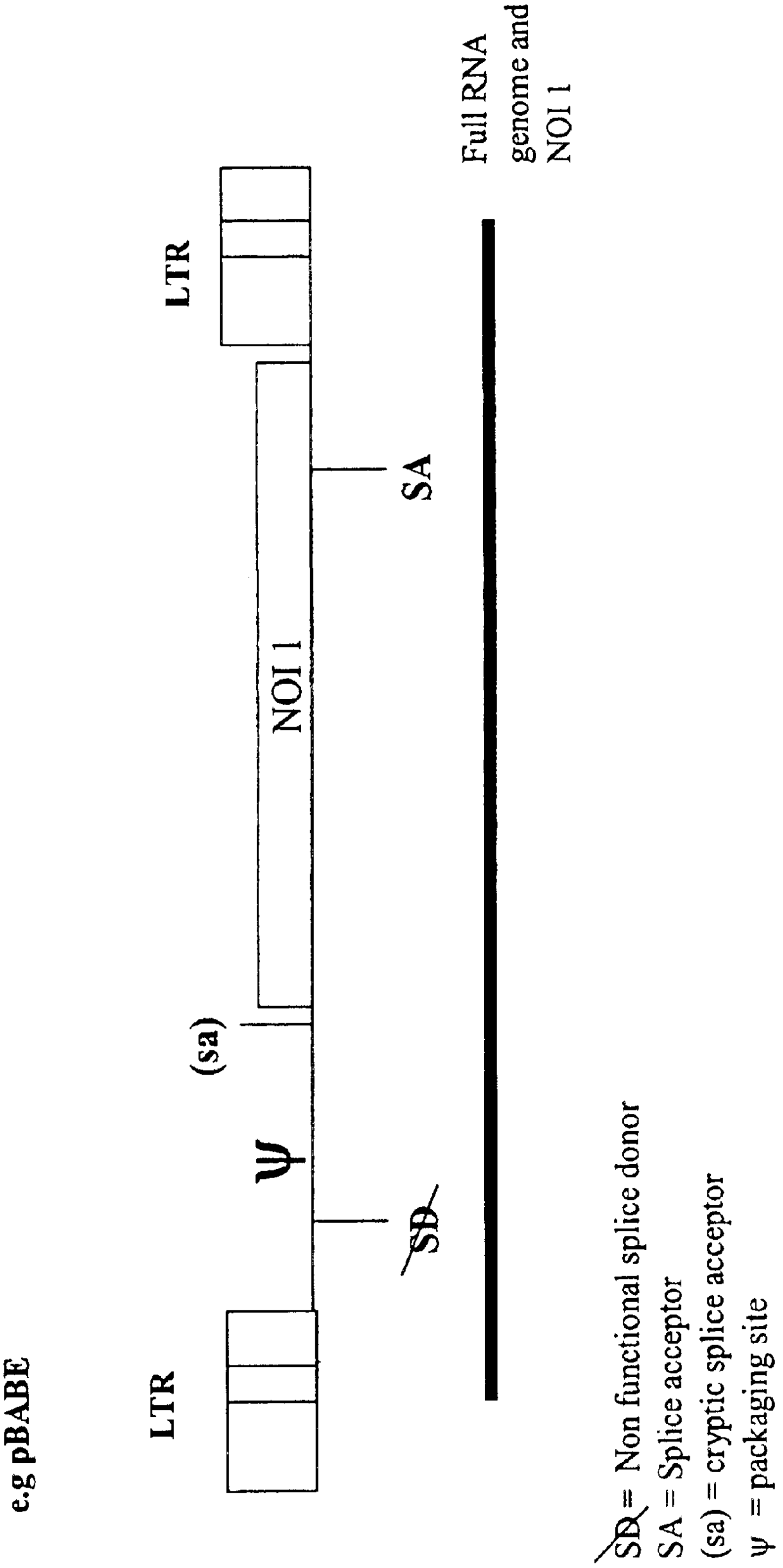
Figure 27C:
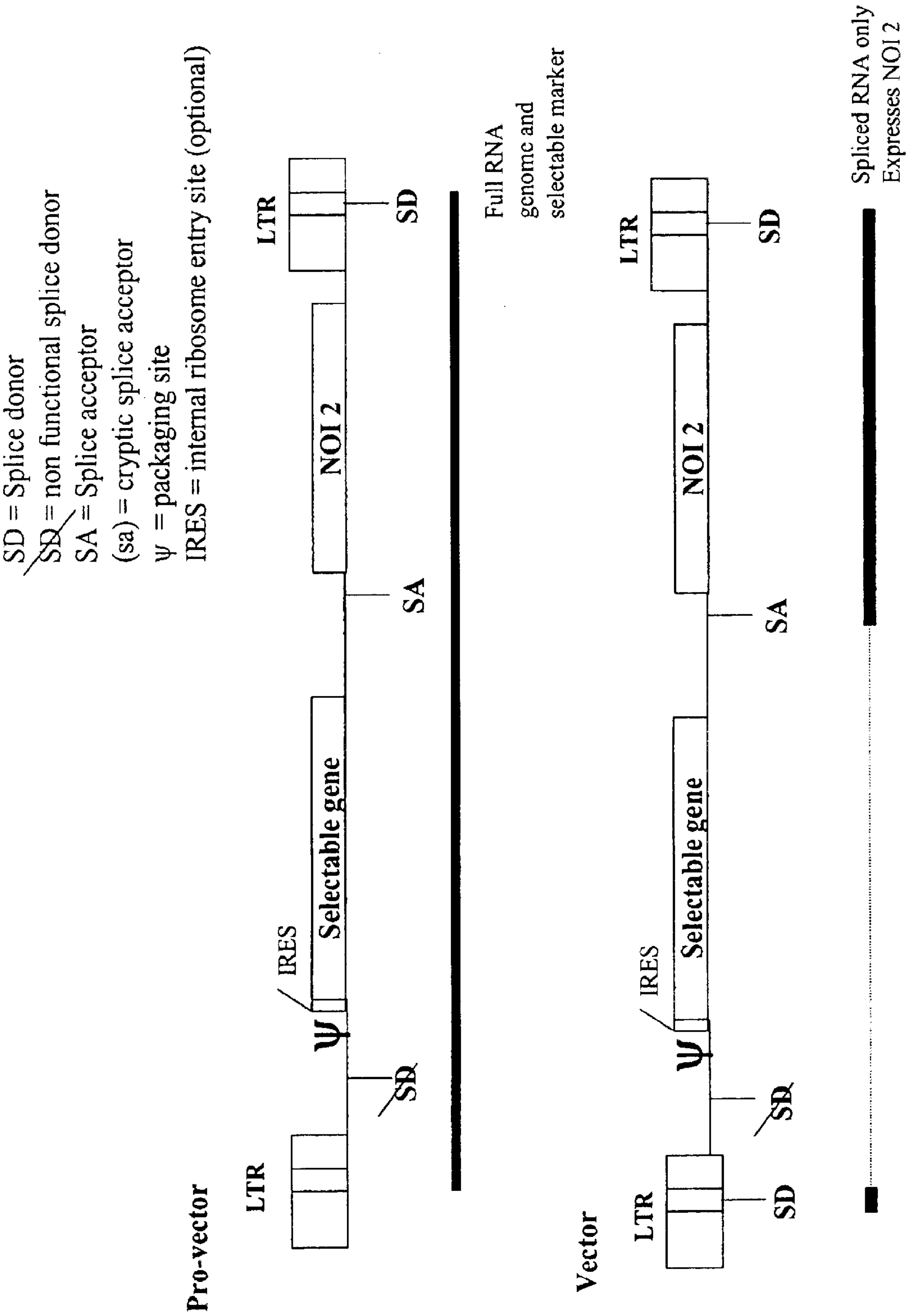
Figure 27C:
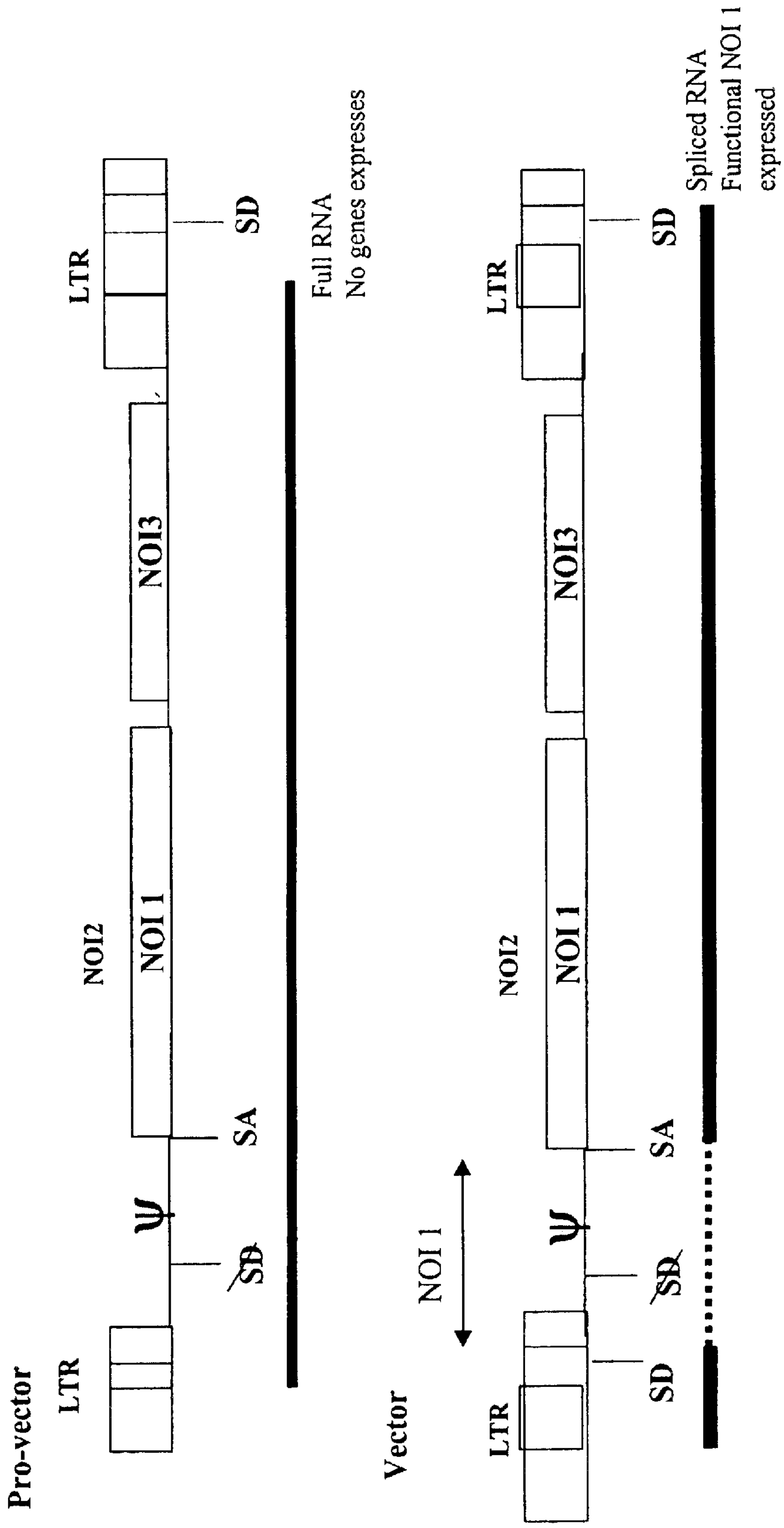

This aspect of the present invention can be called the "split-intron"*aspect. A schematic diagram showing this aspect of the present invention is provided in FIG. 27*c*. In contrast, FIGS. 27*a* and 27*b* show splicing configurations in known retroviral vectors.

Another broad aspects of the present invention include a novel delivery system which comprises one or more adenoviral vector components capable of packaging one or more lentiviral vector components, wherein optionally the lentiviral vector comprises a split intron configuration.

This aspect of the present invention in the general sense can be called a hybrid viral vector system. In this particular case, the combination of an adenoviral component and a lentiviral component can be called a dual hybrid viral vector system.

Figure 28:
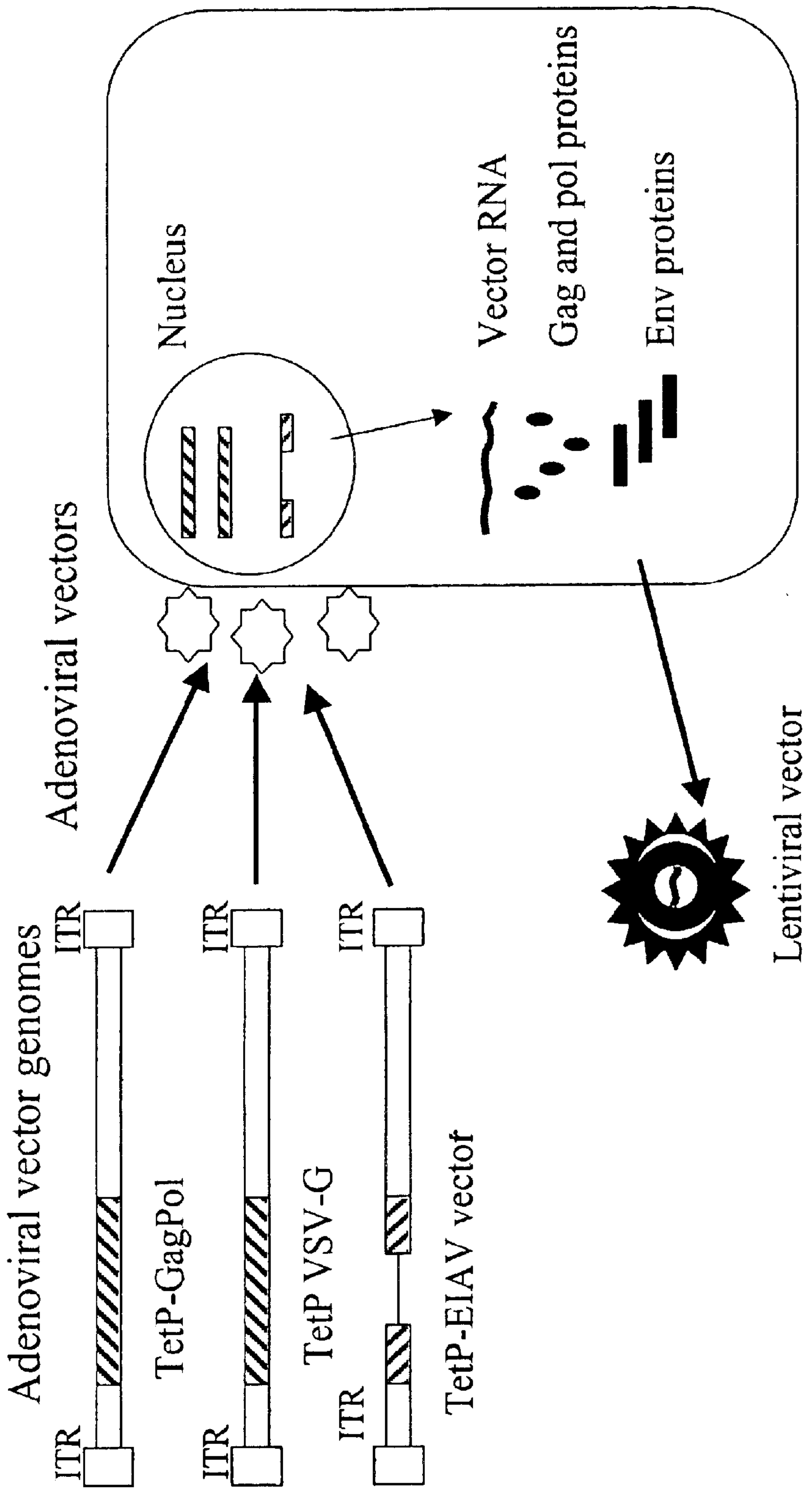

A schematic diagram showing this aspect of the present invention is provided in FIG. 28.

These and other broad aspects of the present invention are discussed herein.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A retroviral vector comprising:

(a) a 3' and 5' long terminal repeat (LTR);

(b) a functional splice donor site within the 5' LTR;

(c) a functional splice donor site;

(d) a first nucleotide sequence of interest (NOI) flanked upstream by the functional splice donor site and downstream by the functional splice acceptor site; and (e) a second NOI downstream of the functional slice acceptor site and upstream of the 3' LTR;

whereby the first NOI is capable of being spliced out of RNA when transcribed from the retroviral vector.

2. The retroviral vector according to claim 1 wherein the second NOI encodes a therapeutic expression product.

3. The retroviral vector according to claim 1 wherein the first NOI, or an expression product thereof, comprises a selectable marker or a viral element.

4. The retroviral vector according to claim 1 wherein the functional splice donor site is from a virus.

5. The retroviral vector according to claim 1 wherein the functional splice donor site is from an intron.

6. The retroviral vector according to claim 5 wherein the intron is the small t-intron of SV40 virus.

7. The retroviral vector according to claim 1 further comprising a multiple cloning site, wherein the functional splice acceptor site is locate upstream of the multiple cloning site.

8. The retroviral vector according to claim 1 wherein the functional splice acceptor site is from a nucleotide sequence coding for an immunological protein.

9. The retroviral vector according to claim 8 wherein the immunological protein is an immunoglobulin.

10. Tho retroviral vector according to claim 9 wherein the immunoglobulin is from an immunoglobulin heavy chain variable region.

11. The retroviral vector according to claim 1 wherein the vector is a murine oncoretrovirus vector or a lentivirus vector.

12. The retroviral vector according to claim 11 wherein the vector is a MMLV, MSV, MMTV, HIV-1 or EIAV retroviral vector.

13. A method of producing a retroviral vector comprising a functional splice donor site within its 5' long terminal repeat (LTR), the method comprising:

(a) introducing, into a packaging cell, a retroviral pro-vector comprising:

(i) a 3' and 5' L' LTR;

(ii) a functional splice donor site located within the 3' LTR;

(iii) a functional splice acceptor site upstream of the splice donor site;

(iv) a first nucleotide sequence of interest (NOI) upstream of the functional splice acceptor site, wherein the first NOI comprises a packaging signal; and (v) a second NOI downstream of the functional splice acceptor site and upstream of the 3' LTR, wherein the retroviral pro-vector is packaged into a viral particle in the packaging cell; and (b) infecting a target cell with the viral particle, wherein the retroviral pro-vector is reverse transcribe;

thereby producing a retroviral vector comprising a functional splice donor site within its 5' LTR.

14. The method according to claim 13 wherein the first NOI is expressed in the packaging cell.

15. The method according to claim 13 wherein the first NOI further comprises a selectable marker or a viral element.

16. The method according to claim 15 wherein the viral element is a retroviral envelope sequence.

17. The method according to claim 13 wherein the retroviral pro-vector is a murine oncoretrovirus pro-vector or a lentivirus retroviral pro-vector.

18. The method according to claim 17 wherein the retroviral pro-vector is a MMLV, MSV, MMTV, HIV-1, or EIAV retroviral pro-vector.

19. The method according to claim 13 wherein the retroviral pro-vector comprises a non-retroviral transcriptional control sequence upstream of the functional splice donor site.

20. The method according to claim 19, wherein the transcriptional control sequence is an internal promoter.

21. The method according to claim 19, wherein the transcriptional control sequence is located in the 5' LTR.

22. The method according to claim 19, wherein the transcriptional control sequence is located in the 3' LTR.

23. A retroviral vector comprising a functional splice donor site with its 5' LTR, wherein the retroviral vector is produced by the method of claim 13.

24. A retroviral vector comprising:

(a) a 3' and 5' long terminal repeat (LTR);

(b) a functional splice donor site located within the 5' LTR;

(c) a functional splice acceptor site located downstream of the functional splice donor site; and (d) an NOI downstream of the functional splice acceptor site and upstream of the 3' LTR;

whereby an intervening sequence between the functional splice donor site and the functional splice acceptor site spliced out of RNA transcribe from the retroviral vector.

25. The retroviral vector according to claim 24, wherein the intervening sequence comprises a viral element.

26. The retroviral vector according to claim 25, wherein the viral element is a package signal.

27. The retroviral vector according to claim 24, wherein the functional splice donor site is from a virus.

28. The retroviral vector according to claim 24, wherein the functional splice donor site is from an intron.

29. The retroviral vector according to claim 28, wherein the intron is the small t-intron of SV40 virus.

30. The retroviral vector according to claim 24, wherein the comprising a multiple cloning site, wherein the functional splice acceptor site is located upstream of the multiple cloning site.

31. The retroviral vector according to claim 24, wherein the functional splice acceptor site is from a nucleotide sequence coding for an immunological protein.

32. The retroviral vector according to claim 31, wherein the immunological protein is an immunoglobulin.

33. The retroviral vector according to claim 32, wherein the immunoglobulin is from an immunoglobulin heavy chain variable region.

34. The retroviral vector according to claim 24, wherein the vector is a murine oncoretrovirus vector or a lentivirus vector.

35. The retroviral vector according to claim 34, wherein the vector is a MMLV, MSV, MMTV, HIV-1 or EIAV retroviral vector.

36. A method of producing a retroviral vector comprising a functional splice donor site within its 5' LTR, the method comprising:

(a) introducing into a packaging cell, a retroviral pro-vector comprising:

(i) a 3' and 5' LTR;

(ii) a functional splice donor site located within the 3' LTR;

(iii) a functional splice acceptor site;

(iv) a packaging signal upstream of the functional splice acceptor site; and (v) an NOI downstream of the functional splice acceptor site and upstream of the 3' LTR, wherein the retroviral pro-vector is packaged into a viral particle in the packaging cell; and (b) infecting a target cell with the viral particle, wherein the retroviral pro-vector is reverse transcribed;

thereby producing a retroviral vector comprising a functional splice donor site within its 5' LTR.

37. The method according to claim 36, wherein the retroviral pro-vector comprises a non-retroviral transcriptional control sequence upstream of the functional splice donor site.

38. The method according to claim 37, wherein the transcriptional control sequence is an internal promoter.

39. The method according to claim 37, wherein the transcriptional control sequence is located in the 5' LTR.

40. The method according to claim 37, wherein the transcriptional control sequence is located in the 3' LTR.

41. A retroviral vector comprising a functional splice donor site within its 5' LTR, wherein the retroviral vector is produced by the method of claim 36.

* * * * *

SEQUENCE LISTING

```
<160> NUMBER OF SEQ ID NOS:  36

<210> SEQ ID NO 1
<211> LENGTH: 5689
<212> TYPE: DNA
<213> ORGANISM: Artificial Sequence
<220> FEATURE:
<223> OTHER INFORMATION: Description of Artificial Sequence: MLV pICUT

<400> SEQUENCE: 1

gctagcttaa gtaacgccac tttgcaaggc atggaaaaat acataactga gaatagaaaa      60

gttcagatca aggtcaggaa caaagaaaca gctgaatacc aaacaggata tctgtggtaa     120

gcggttcctg ccccggctca gggccaagaa cagatgagac agctgagtga tgggccaaac     180

aggatatctg tggtaagcag ttcctgcccc ggctcggggc caagaacaga tggtccccag     240

atgcggtcca gccctcagca gtttctagtg aatcatcaga tgtttccagg gtgccccaag     300

gacctgaaaa tgaccctgta ccttatttga actaaccaat cagttcgctt ctcgcttctg     360

ttcgcgcgct tccgctctcc gagctcaata aaagagccca caacccctca ctcggcgcgc     420

cagtcttccg atagactgcg tcgcccgggt acccgtattc ccaataaagc ctcttgctgt     480

ttgcatccga atcgtggtct cgctgttcct tgggagggtc tcctctgagt gattgactac     540

ccacgacggg ggtctttcat ttgggggctc gtccgggatt tggagacccc tgcccaggga     600

ccaccgaccc accaccggga ggcaagctgg ccagcaactt atctgtgtct gtccgattgt     660

ctagtgtcta tgtttgatgt tatgcgcctg cgtctgtact agttagctaa ctagctctgt     720
```

-continued

```
atctggcgga cccgtggtgg aactgacgag ttctgaacac ccggccgcaa ccctgggaga    780
cgtcccaggg actttggggg ccgtttttgt ggcccgacct gaggaaggga gtcgatgtgg    840
aatccgaccc cgtcaggata tgtggttctg gtaggagacg agaacctaaa acagttcccg    900
cctccgtctg aatttttgct ttcggtttgg aaccgaagcc gcgcgtcttg tctgctgcag    960
cgctgcagca tcgttctgtg ttgtctctgt ctgactgtgt ttctgtattt gtctgaaaat   1020
tagggccaga ctgttaccac tcccttaagt ttgaccttag gtcactggaa agatgtcgag   1080
cggatcgctc acaaccagtc ggtagatgtc aagaagagac gttgggttac cttctgctct   1140
gcagaatggc caacctttaa cgtcggatgg ccgcgagacg gcacctttaa ccgagacctc   1200
atcacccagg ttaagatcaa ggtcttttca cctggcccgc atggacaccc agaccaggtc   1260
ccctacatcg tgacctggga agccttggct tttgaccccc ctccctgggt caagcccttt   1320
gtacacccta agcctccgcc tcctcttcct ccatccgccc cgtctctccc ccttgaacct   1380
cctcgttcga ccccgcctcg atcctccctt tatccagccc tcactccttc tctaggcgcc   1440
ggaattcgtt aactcgagga tctaacctag gtctcgagtg tttaaacact gggcttgtcg   1500
agacagagaa gactcttgcg tttctgatag gcacctattg gtcttactga catccacttt   1560
gcctttctct ccacaggtga ggcctaggct tttgcaaaaa gcttgggctg caggtcgagg   1620
cggatctgat caagagacag gatgaggatc gtttcgcatg attgaacaag atggattgca   1680
cgcaggttct ccggccgctt gggtggagag gctattcggc tatgactggg cacaacagac   1740
aatcggctgc tctgatgccg ccgtgttccg gctgtcagcg caggggcgcc cggttctttt   1800
tgtcaagacc gacctgtccg gtgccctgaa tgaactgcag gacgaggcag cgcggctatc   1860
gtggctggcc acgacgggcg ttccttgcgc agctgtgctc gacgttgtca ctgaagcggg   1920
aagggactgg ctgctattgg gcgaagtgcc ggggcaggat ctcctgtcat ctcaccttgc   1980
tcctgccgag aaagtatcca tcatggctga tgcaatgcgg cggctgcata cgcttgatcc   2040
ggctacctgc ccattcgacc accaagcgaa acatcgcatc gagcgagcac gtactcggat   2100
ggaagccggt cttgtcgatc aggatgatct ggacgaagag catcaggggc tcgcgccagc   2160
cgaactgttc gccaggctca aggcgcgcat gcccgacggc gaggatctcg tcgtgaccca   2220
tggcgatgcc tgcttgccga atatcatggt ggaaaatggc cgcttttctg gattcatcga   2280
ctgtggccgg ctgggtgtgg cggaccgcta tcaggacata gcgttggcta cccgtgatat   2340
tgctgaagag cttggcggcg aatgggctga ccgcttcctc gtgctttacg gtatcgccgc   2400
tcccgattcg cagcgcatcg ccttctatcg ccttcttgac gagttcttct gagcgggact   2460
ctggggttcg ataaaataaa agattttatt tagtctccag aaaaaggggg gaatgaaaga   2520
ccccacctgt aggtttggca agctagctta agtaacgcca ttttgcaagg catggaaaaa   2580
tacataactg agaatagaga agttcagatc aaggtcagga acagatggaa cagctgaata   2640
tgggccaaac aggatatctg tggtaagcag ttcctgcccc ggctcagggc caagaacaga   2700
tggaacagct gaatatgggc caaacaggat atctgtggta agcagttcct gccccggctc   2760
agggccaaga acagatggtc cccagatgcg gtccagccct cagcagtttc tagagaacca   2820
tcagatgttt ccagggtgcc ccaaggacct gaaatgaccc tgtgccttat ttgaactaac   2880
caatcagttc gcttctcgct tctgttcgcg cgcttctgct ccccgagctc aataaaagag   2940
cccacaaccc ctcactcggg gcgccgttaa cactagtaag cttgctctaa ggtaaatatg   3000
tcgacaggcc tgcgccagtc ctccgattga ctgagtcgcc cgggtacccg tgtatccaat   3060
```

-continued

```
aaaccctctt gcagttgcat ccgacttgtg gtctcgctgt tccttgggag ggtctcctct   3120

gagtgattga ctacccgtca gcgggggtct ttcatttggg ggctcgtccg ggatcgggag   3180

acccctgccc agggaccacc gacccaccac cgggaggtaa gctggctgcc tcgcgcgttt   3240

cggtgatgac ggtgaaaacc tctgacacat gcagctcccg gagacggtca cagcttgtct   3300

gtaagcggat gccgggagca gacaagcccg tcagggcgcg tcagcgggtg ttggcgggtg   3360

tcggggcgca gccatgaccc agtcacgtag cgatagcgga gtgtatactg gcttaactat   3420

gcggcatcag agcagattgt actgagagtg caccatatgc ggtgtgaaat accgcacaga   3480

tgcgtaagga gaaaataccg catcaggcgc tcttccgctt cctcgctcac tgactcgctg   3540

cgctcggtcg ttcggctgcg gcgagcggta tcagctcact caaaggcggt aatacggtta   3600

tccacagaat caggggataa cgcaggaaag aacatgtgag caaaaggcca gcaaaaggcc   3660

aggaaccgta aaaaggccgc gttgctggcg tttttccata ggctccgccc ccctgacgag   3720

catcacaaaa atcgacgctc aagtcagagg tggcgaaacc cgacaggact ataaagatac   3780

caggcgtttc cccctggaag ctccctcgtg cgctctcctg ttccgaccct gccgcttacc   3840

ggatacctgt ccgcctttct cccttcggga agcgtggcgc tttctcatag ctcacgctgt   3900

aggtatctca gttcggtgta ggtcgttcgc tccaagctgg gctgtgtgca cgaacccccc   3960

gttcagcccg accgctgcgc cttatccggt aactatcgtc ttgagtccaa cccggtaaga   4020

cacgacttat cgccactggc agcagccact ggtaacagga ttagcagagc gaggtatgta   4080

ggcggtgcta cagagttctt gaagtggtgg cctaactacg gctacactag aaggacagta   4140

tttggtatct gcgctctgct gaagccagtt accttcggaa aaagagttgg tagctcttga   4200

tccggcaaac aaaccaccgc tggtagcggt ggtttttttg tttgcaagca gcagattacg   4260

cgcagaaaaa aaggatctca agaagatcct ttgatctttt ctacggggtc tgacgctcag   4320

tggaacgaaa actcacgtta agggattttg gtcatgagat tatcaaaaag gatcttcacc   4380

tagatccttt taaattaaaa atgaagtttt aaatcaatct aaagtatata tgagtaaact   4440

tggtctgaca gttaccaatg cttaatcagt gaggcaccta tctcagcgat ctgtctattt   4500

cgttcatcca tagttgcctg actccccgtc gtgtagataa ctacgatacg ggagggctta   4560

ccatctggcc ccagtgctgc aatgataccg cgagacccac gctcaccggc tccagattta   4620

tcagcaataa accagccagc cggaagggcc gagcgcagaa gtggtcctgc aactttatcc   4680

gcctccatcc agtctattaa ttgttgccgg gaagctagag taagtagttc gccagttaat   4740

agtttgcgca acgttgttgc cattgctgca ggcatcgtgg tgtcacgctc gtcgtttggt   4800

atggcttcat tcagctccgg ttcccaacga tcaaggcgag ttacatgatc ccccatgttg   4860

tgcaaaaaag cggttagctc cttcggtcct ccgatcgttg tcagaagtaa gttggccgca   4920

gtgttatcac tcatggttat ggcagcactg cataattctc ttactgtcat gccatccgta   4980

agatgctttt ctgtgactgg tgagtactca accaagtcat tctgagaata gtgtatgcgg   5040

cgaccgagtt gctcttgccc ggcgtcaaca cgggataata ccgcgccaca tagcagaact   5100

ttaaaagtgc tcatcattgg aaaacgttct tcggggcgaa aactctcaag gatcttaccg   5160

ctgttgagat ccagttcgat gtaacccact cgtgcaccca actgatcttc agcatctttt   5220

actttcacca gcgtttctgg gtgagcaaaa acaggaaggc aaaatgccgc aaaaaaggga   5280

ataagggcga cacggaaatg ttgaatactc atactcttcc tttttcaata ttattgaagc   5340

atttatcagg gttattgtct catgagcgga tacatatttg aatgtattta gaaaaataaa   5400

caaatagggg ttccgcgcac atttccccga aaagtgccac ctgacgtcta agaaaccatt   5460
```

-continued attatcatga cattaaccta taaaaatagg cgtatcacga ggccctttcg tcttcaagaa 5520
ttcataccag atcaccgaaa actgtcctcc aaatgtgtcc ccctcacact cccaaattcg 5580
cgggcttctg cctcttagac cactctaccc tattccccac actcaccgga gccaaagccg 5640
cggcccttcc gtttctttgc ttttgaaaga ccccacccgt aggtggcaa 5689

<210> SEQ ID NO 2
<211> LENGTH: 9756
<212> TYPE: DNA
<213> ORGANISM: Artificial Sequence
<220> FEATURE:
<223> OTHER INFORMATION: Description of Artificial Sequence: pEICUT-LacZ

<400> SEQUENCE: 2
tgaataataa aatgtgtgtt tgtccgaaat acgcgttttg agatttctgt cgccgactaa 60
attcatgtcg cgcgatagtg gtgtttatcg ccgatagaga tggcgatatt ggaaaaattg 120
atatttgaaa atatggcata ttgaaaatgt cgccgatgtg agtttctgtg taactgatat 180
cgccattttt ccaaaagtga tttttgggca tacgcgatat ctggcgatag cgcttatatc 240
gtttacgggg gatggcgata gacgactttg gtgacttggg cgattctgtg tgtcgcaaat 300
atcgcagttt cgatataggt gacagacgat atgaggctat atcgccgata gaggcgacat 360
caagctggca catggccaat gcatatcgat ctatacattg aatcaatatt ggccattagc 420
catattattc attggttata tagcataaat caatattggc tattggccat tgcatacgtt 480
gtatccatat cgtaatatgt acatttatat tggctcatgt ccaacattac cgccatgttg 540
acattgatta ttgactagtt attaatagta atcaattacg gggtcattag ttcatagccc 600
atatatggag ttccgcgtta cataacttac ggtaaatggc ccgcctggct gaccgcccaa 660
cgacccccgc ccattgacgt caataatgac gtatgttccc atagtaacgc caatagggac 720
tttccattga cgtcaatggg tggagtattt acggtaaact gcccacttgg cagtacatca 780
agtgtatcat atgccaagtc cgccccctat tgacgtcaat gacggtaaat ggcccgcctg 840
gcattatgcc cagtacatga ccttacggga ctttcctact tggcagtaca tctacgtatt 900
agtcatcgct attaccatgg tgatgcggtt ttggcagtac accaatgggc gtggatagcg 960
gtttgactca cggggatttc caagtctcca ccccattgac gtcaatggga gtttgttttg 1020
gcaccaaaat caacgggact ttccaaaatg tcgtaacaac tgcgatcgcc cgccccgttg 1080
acgcaaatgg gcggtaggcg tgtacggtgg gaggtctata taagcagagc tcgtttagtg 1140
aaccgggcac tcagattctg cggtctgagt cccttctctg ctgggctgaa aaggcctttg 1200
taataaatat aattctctac tcagtccctg tctctagttt gtctgttcga gatcctacag 1260
ttggcgcccg aacagggacc tgagaggggc gcagacccta cctgttgaac ctggctgatc 1320
gtaggatccc cgggacagca gaggagaact tacagaagtc ttctggaggt gttcctggcc 1380
agaacacagg aggacaggta agatgggaga ccctttgaca tggagcaagg cgctcaagaa 1440
gttagagaag gtgacggtac aagggtctca gaaattaact actggtaact gtaattgggc 1500
gctaagtcta gtagacttat ttcatgatac caactttgta aaagaaaagg actctagagt 1560 cgacccccctc gacgtttaaa cactgggctt gtcgagacag agaagactct tgcgtttctg 1620
ataggcacct attggtctta ctgacatcca ctttgccttt ctctccacag gtcacgtgaa 1680
gctagcctcg aggatctgcg gatccgggga attccccagt ctcaggatcc accatggggg 1740
atcccgtcgt tttacaacgt cgtgactggg aaaaccctgg cgttacccaa cttaatcgcc 1800

-continued

```
ttgcagcaca tccccctttc gccagctggc gtaatagcga agaggcccgc accgatcgcc   1860
cttcccaaca gttgcgcagc ctgaatggcg aatggcgctt tgcctggttt ccggcaccag   1920
aagcggtgcc ggaaagctgg ctggagtgcg atcttcctga ggccgatact gtcgtcgtcc   1980
cctcaaactg gcagatgcac ggttacgatg cgcccatcta caccaacgta acctatccca   2040
ttacggtcaa tccgccgttt gttcccacgg agaatccgac gggttgttac tcgctcacat   2100
ttaatgttga tgaaagctgg ctacaggaag gccagacgcg aattattttt gatggcgtta   2160
actcggcgtt tcatctgtgg tgcaacgggc gctgggtcgg ttacggccag gacagtcgtt   2220
tgccgtctga atttgacctg agcgcatttt tacgcgccgg agaaaaccgc ctcgcggtga   2280
tggtgctgcg ttggagtgac ggcagttatc tggaagatca ggatatgtgg cggatgagcg   2340
gcattttccg tgacgtctcg ttgctgcata aaccgactac acaaatcagc gatttccatg   2400
ttgccactcg ctttaatgat gatttcagcc gcgctgtact ggaggctgaa gttcagatgt   2460
gcggcgagtt gcgtgactac ctacgggtaa cagtttcttt atggcagggt gaaacgcagg   2520
tcgccagcgg caccgcgcct ttcggcggtg aaattatcga tgagcgtggt ggttatgccg   2580
atcgcgtcac actacgtctg aacgtcgaaa acccgaaact gtggagcgcc gaaatcccga   2640
atctctatcg tgcggtggtt gaactgcaca ccgccgacgg cacgctgatt gaagcagaag   2700
cctgcgatgt cggtttccgc gaggtgcgga ttgaaaatgg tctgctgctg ctgaacggca   2760
agccgttgct gattcgaggc gttaaccgtc acgagcatca tcctctgcat ggtcaggtca   2820
tggatgagca gacgatggtg caggatatcc tgctgatgaa gcagaacaac tttaacgccg   2880
tgcgctgttc gcattatccg aaccatccgc tgtggtacac gctgtgcgac cgctacggcc   2940
tgtatgtggt ggatgaagcc aatattgaaa cccacggcat ggtgccaatg aatcgtctga   3000
ccgatgatcc gcgctggcta ccggcgatga gcgaacgcgt aacgcgaatg gtgcagcgcg   3060
atcgtaatca cccgagtgtg atcatctggt cgctggggaa tgaatcaggc cacggcgcta   3120
atcacgacgc gctgtatcgc tggatcaaat ctgtcgatcc ttcccgcccg gtgcagtatg   3180
aaggcggcgg agccgacacc acggccaccg atattatttg cccgatgtac gcgcgcgtgg   3240
atgaagacca gcccttcccg gctgtgccga aatggtccat caaaaaatgg ctttcgctac   3300
ctggagagac gcgcccgctg atcctttgcg aatacgccca cgcgatgggt aacagtcttg   3360
gcggtttcgc taaatactgg caggcgtttc gtcagtatcc ccgtttacag ggcggcttcg   3420
tctgggactg ggtggatcag tcgctgatta aatatgatga aaacggcaac ccgtggtcgg   3480
cttacggcgg tgattttggc gatacgccga acgatcgcca gttctgtatg aacggtctgg   3540
tctttgccga ccgcacgccg catccagcgc tgacggaagc aaaacaccag cagcagtttt   3600
tccagttccg tttatccggg caaaccatcg aagtgaccag cgaataccgt ttccgtcata   3660
gcgataacga gctcctgcac tggatggtgg cgctggatgg taagccgctg gcaagcggtg   3720
aagtgcctct ggatgtcgct ccacaaggta aacagttgat tgaactgcct gaactaccgc   3780
agccggagag cgccgggcaa ctctggctca cagtacgcgt agtgcaaccg aacgcgaccg   3840
catggtcaga agccgggcac atcagcgcct ggcagcagtg gcgtctggcg gaaaacctca   3900
gtgtgacgct ccccgccgcg tcccacgcca tcccgcatct gaccaccagc gaaatggatt   3960
tttgcatcga gctgggtaat aagcgttggc aatttaaccg ccagtcaggc tttctttcac   4020
agatgtggat tggcgataaa aaacaactgc tgacgccgct gcgcgatcag ttcacccgtg   4080
caccgctgga taacgacatt ggcgtaagtg aagcgacccg cattgaccct aacgcctggg   4140
tcgaacgctg gaaggcggcg ggccattacc aggccgaagc agcgttgttg cagtgcacgg   4200
```

-continued

```
cagatacact tgctgatgcg gtgctgatta cgaccgctca cgcgtggcag catcagggga   4260
aaaccttatt tatcagccgg aaaacctacc ggattgatgg tagtggtcaa atggcgatta   4320
ccgttgatgt tgaagtggcg agcgatacac cgcatccggc gcggattggc ctgaactgcc   4380
agctggcgca ggtagcagag cgggtaaact ggctcggatt agggccgcaa gaaaactatc   4440
ccgaccgcct tactgccgcc tgttttgacc gctgggatct gccattgtca gacatgtata   4500
ccccgtacgt cttcccgagc gaaaacggtc tgcgctgcgg gacgcgcgaa ttgaattatg   4560
gcccacacca gtggcgcggc gacttccagt tcaacatcag ccgctacagt caacagcaac   4620
tgatggaaac cagccatcgc catctgctgc acgcggaaga aggcacatgg ctgaatatcg   4680
acggtttcca tatggggatt ggtggcgacg actcctggag cccgtcagta tcggcggaat   4740
tccagctgag cgccggtcgc taccattacc agttggtctg gtgtcaaaaa taataataac   4800
cgggcagggg ggatccgcag atccggctgt ggaatgtgtg tcagttaggg tgtggaaagt   4860
ccccaggctc cccagcaggc agaagtatgc aaagcatgcc tgcagcccgg gggatccact   4920
agtgtatgtt tagaaaaaca agggggggaac tgtggggttt ttatgagggg ttttataaat   4980
gattataaga gtaaaaagaa agttgctgat gctctcataa ccttgtataa cccaaaggac   5040
tagctcatgt tgctaggcaa ctaaaccgca ataaccgcat ttgtgacgcg agttccccat   5100
tggtgacgcg ttttgagatt tctgtcgccg actaaattca tgtcgcgcga tagtggtgtt   5160
tatcgccgat agagatggcg atattggaaa aattgatatt tgaaaatatg gcatattgaa   5220
aatgtcgccg atgtgagttt ctgtgtaact gatatcgcca tttttccaaa agtgattttt   5280
gggcatacgc gatatctggc gatagcgctt atatcgttta cgggggatgg cgatagacga   5340
ctttggtgac ttgggcgatt ctgtgtgtcg caaatatcgc agtttcgata taggtgacag   5400
acgatatgag gctatatcgc cgatagaggc gacatcaagc tggcacatgg ccaatgcata   5460
tcgatctata cattgaatca atattggcca ttagccatat tattcattgg ttatatagca   5520
taaatcaata ttggctattg gccattgcat acgttgtatc catatcgtaa tatgtacatt   5580
tatattggct catgtccaac attaccgcca tgttgacatt gattattgac tagttattaa   5640
tagtaatcaa ttacggggtc attagttcat agcccatata tggagttccg cgttacataa   5700
cttacggtaa atggcccgcc tggctgaccg cccaacgacc cccgcccatt gacgtcaata   5760
atgacgtatg ttcccatagt aacgccaata gggactttcc attgacgtca atgggtggag   5820
tatttacggt aaactgccca cttggcagta catcaagtgt atcatatgcc aagtccgccc   5880
cctattgacg tcaatgacgg taaatggccc gcctggcatt atgcccagta catgacctta   5940
cgggactttc ctacttggca gtacatctac gtattagtca tcgctattac catggtgatg   6000
cggttttggc agtacaccaa tgggcgtgga tagcggtttg actcacgggg atttccaagt   6060
ctccacccca ttgacgtcaa tgggagtttg ttttggcacc aaaatcaacg ggactttcca   6120
aaatgtcgta acaactgcga tcgcccgccc cgttgacgca aatgggcggt aggcgtgtac   6180
ggtgggaggt ctatataagc agagctcgtt tagtgaaccg acttaagtct tcctgcaggg   6240
gctctaaggt aaatagggca ctcagattct gcggtctgag tcccttctct gctgggctga   6300
aaaggccttt gtaataaata taattctcta ctcagtccct gtctctagtt tgtctgttcg   6360
agatcctaca gttggcgccc gaacagggac ctgagagggg cgcagaccct acctgttgaa   6420
cctggctgat cgtaggatcc ccggccaggt gtggaaagtc cccaggctcc ccagcaggca   6480
gaagtatgca aagcatgcat ctcaattagt cagcaaccat agtcccgccc ctaactccgc   6540
```

-continued

```
ccatcccgcc cctaactccg cccagttccg cccattctcc gccccatggc tgactaattt   6600
tttttattta tgcagaggcc gaggccgcct cggcctctga gctattccag aagtagtgag   6660
gaggcttttt tggaggccta ggcttttgca aaaagcttga ttcttctgac acaacagtct   6720
cgaacttaag gctagagcca ccatgattga acaagatgga ttgcacgcag gttctccggc   6780
cgcttgggtg gagaggctat tcggctatga ctgggcacaa cagacaatcg gctgctctga   6840
tgccgccgtg ttccggctgt cagcgcaggg gcgcccggtt ctttttgtca agaccgacct   6900
gtccggtgcc ctgaatgaac tgcaggacga ggcagcgcgg ctatcgtggc tggccacgac   6960
gggcgttcct tgcgcagctg tgctcgacgt tgtcactgaa gcgggaaggg actggctgct   7020
attgggcgaa gtgccggggc aggatctcct gtcatctcac cttgctcctg ccgagaaagt   7080
atccatcatg gctgatgcaa tgcggcggct gcatacgctt gatccggcta cctgcccatt   7140
cgaccaccaa gcgaaacatc gcatcgagcg agcacgtact cggatggaag ccggtcttgt   7200
cgatcaggat gatctggacg aagagcatca ggggctcgcg ccagccgaac tgttcgccag   7260
gctcaaggcg cgcatgcccg acggcgagga tctcgtcgtg acccatggcg atgcctgctt   7320
gccgaatatc atggtggaaa atggccgctt ttctggattc atcgactgtg gccggctggg   7380
tgtggcggac cgctatcagg acatagcgtt ggctacccgt gatattgctg aagagcttgg   7440
cggcgaatgg gctgaccgct tcctcgtgct ttacggtatc gccgctcccg attcgcagcg   7500
catcgccttc tatcgccttc ttgacgagtt cttctgagcg ggactctggg gttcgaaatg   7560
accgaccaag cgacgcccaa cctgccatca cgatggccgc aataaaatat ctttattttc   7620
attacatctg tgtgttggtt ttttgtgtga atcgatagcg ataaggatcg atccgcgtat   7680
ggtgcactct cagtacaatc tgctctgatg ccgcatagtt aagccagccc cgacacccgc   7740
caacacccgc tgacgcgccc tgacgggctt gtctgctccc ggcatccgct tacagacaag   7800
ctgtgaccgt ctccgggagc tgcatgtgtc agaggttttc accgtcatca ccgaaacgcg   7860
cgagacgaaa gggcctcgtg atacgcctat ttttataggt taatgtcatg ataataatgg   7920
tttcttagac gtcaggtggc acttttcggg gaaatgtgcg cggaacccct atttgtttat   7980
ttttctaaat acattcaaat atgtatccgc tcatgagaca ataaccctga taaatgcttc   8040
aataatattg aaaaaggaag agtatgagta ttcaacattt ccgtgtcgcc cttattccct   8100
tttttgcggc attttgcctt cctgtttttg ctcacccaga aacgctggtg aaagtaaaag   8160
atgctgaaga tcagttgggt gcacgagtgg gttacatcga actggatctc aacagcggta   8220
agatccttga gagttttcgc cccgaagaac gttttccaat gatgagcact tttaaagttc   8280
tgctatgtgg cgcggtatta tcccgtattg acgccgggca agagcaactc ggtcgccgca   8340
tacactattc tcagaatgac ttggttgagt actcaccagt cacagaaaag catcttacgg   8400
atggcatgac agtaagagaa ttatgcagtg ctgccataac catgagtgat aacactgcgg   8460
ccaacttact tctgacaacg atcggaggac cgaaggagct aaccgctttt ttgcacaaca   8520
tgggggatca tgtaactcgc cttgatcgtt gggaaccgga gctgaatgaa gccataccaa   8580
acgacgagcg tgacaccacg atgcctgtag caatggcaac aacgttgcgc aaactattaa   8640
ctggcgaact acttactcta gcttcccggc aacaattaat agactggatg gaggcggata   8700
aagttgcagg accacttctg cgctcggccc ttccggctgg ctggtttatt gctgataaat   8760
ctggagccgg tgagcgtggg tctcgcggta tcattgcagc actggggcca gatggtaagc   8820
cctcccgtat cgtagttatc tacacgacgg ggagtcaggc aactatggat gaacgaaata   8880
gacagatcgc tgagataggt gcctcactga ttaagcattg gtaactgtca gaccaagttt   8940
```

-continued

```
actcatatat actttagatt gatttaaaac ttcattttta atttaaaagg atctaggtga   9000
agatcctttt tgataatctc atgaccaaaa tcccttaacg tgagttttcg ttccactgag   9060
cgtcagaccc cgtagaaaag atcaaaggat cttcttgaga tccttttttt ctgcgcgtaa   9120
tctgctgctt gcaaacaaaa aaaccaccgc taccagcggt ggtttgtttg ccggatcaag   9180
agctaccaac tctttttccg aaggtaactg gcttcagcag agcgcagata ccaaatactg   9240
tccttctagt gtagccgtag ttaggccacc acttcaagaa ctctgtagca ccgcctacat   9300
acctcgctct gctaatcctg ttaccagtgg ctgctgccag tggcgataag tcgtgtctta   9360
ccgggttgga ctcaagacga tagttaccgg ataaggcgca gcggtcgggc tgaacggggg   9420
gttcgtgcac acagcccagc ttggagcgaa cgacctacac cgaactgaga tacctacagc   9480
gtgagctatg agaaagcgcc acgcttcccg aagggagaaa ggcggacagg tatccggtaa   9540
gcggcagggt cggaacagga gagcgcacga gggagcttcc agggggaaac gcctggtatc   9600
tttatagtcc tgtcgggttt cgccacctct gacttgagcg tcgatttttg tgatgctcgt   9660
caggggggcg gagcctatgg aaaaacgcca gcaacgcggc ctttttacgg ttcctggcct   9720
tttgctggcc ttttgctcac atggctcgac agatct                             9756
```

<210> SEQ ID NO 3
<211> LENGTH: 1964
<212> TYPE: DNA
<213> ORGANISM: Artificial Sequence
<220> FEATURE:
<223> OTHER INFORMATION: Description of Artificial Sequence: m4070A

<400> SEQUENCE: 3

```
atggccagaa gcaccctgag caagccaccc caggacaaaa tcaatccctg gaaacctctg     60
atcgtcatgg gagtcctgtt aggagtaggg atggcagaga gcccccatca ggtctttaat    120
gtaacctgga gagtcaccaa cctgatgact gggcgtaccg ccaatgccac ctccctcctg    180
ggaactgtac aagatgcctt cccaaaatta tattttgatc tatgtgatct ggtcggagag    240
gagtgggacc cttcagacca ggaaccgtat gtcgggtatg gctgcaagta ccccgcaggg    300
agacagcgga cccggacttt tgacttttac gtgtgccctg ggcataccgt aaagtcgggg    360
tgtgggggac caggagaggg ctactgtggt aaatgggggt gtgaaaccac cggacaggct    420
tactggaagc ccacatcatc gtgggaccta atctccctta agcgcggtaa caccccctgg    480
gacacgggat gctctaaagt tgcctgtggc ccctgctacg acctctccaa agtatccaat    540
tccttccaag gggctactcg agggggcaga tgcaaccctc tagtcctaga attcactgat    600
gcaggaaaaa aggctaactg ggacgggccc aaatcgtggg gactgagact gtaccggaca    660
ggaacagatc ctattaccat gttctccctg acccggcagg tccttaatgt gggaccccga    720
gtccccatag ggcccaaccc agtattaccc gaccaaagac tcccttcctc accaatagag    780
attgtaccgg ctccacagcc acctagcccc ctcaatacca gttacccccc ttccactacc    840
agtacaccct caacctcccc tacaagtcca agtgtcccac agccaccccc aggaactgga    900
gatagactac tagctctagt caaaggagcc tatcaggcgc ttaacctcac caatcccgac    960
aagacccaag aatgttggct gtgcttagtg tcgggacctc cttattacga aggagtagcg   1020
gtcgtgggca cttataccaa tcattccacc gctccggcca actgtacggc cacttcccaa   1080
cataagctta ccctatctga agtgacagga cagggcctat gcatgggggc agtacctaaa   1140
actcaccagg ccttatgtaa caccacccaa agcgccggct caggatccta ctaccttgca   1200
```

-continued

```
gcacccgccg gaacaatgtg ggcttgcagc actggattga ctccctgctt gtccaccacg   1260

gtgctcaatc taaccacaga ttattgtgta ttagttgaac tctggcccag agtaatttac   1320

cactcccccg attatatgta tggtcagctt gaacagcgta ccaaatataa aagagagcca   1380

gtatcattga ccctggccct tctactagga ggattaacca tgggagggat tgcagctgga   1440

atagggacgg ggaccactgc cttaattaaa acccagcagt ttgagcagct tcatgccgct   1500

atccagacag acctcaacga agtcgaaaag tcaattacca acctagaaaa gtcactgacc   1560

tcgttgtctg aagtagtcct acagaaccgc agaggcctag atttgctatt cctaaaggag   1620

ggaggtctct gcgcagccct aaaagaagaa tgttgttttt atgcagacca cacggggcta   1680

gtgagagaca gcatggccaa attaagagaa aggcttaatc agagacaaaa actatttgag   1740

acaggccaag gatggttcga agggctgttt aatagatccc cctggtttac caccttaatc   1800

tccaccatca tgggacctct aatagtactc ttactgatct tactctttgg accttgcatt   1860

ctcaatcgat tggtccaatt tgttaaagac aggatctcag tggtccaggc tctggttttg   1920

actcagcaat atcccagcta aaacccatag agtacgagcc atga                    1964
```

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: wild type MMLV

<400> SEQUENCE: 4

```
atgcgttcaa cgctctcaaa accccttaaa aataaggtta acccgcgagg ccccctaatc     60

ccc                                                                    63
```

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: mutant env (m4070A)

<400> SEQUENCE: 5

```
atggccagaa gcaccctgag caagccaccc caggacaaaa atccctggaa acctctgatc     60

gtc                                                                    63
```

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 6

```
tattaataac tagt                                                        14
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 7

```
gctacgcaga gctcgtttag tgaaccgggc actcagattc tg                        42
```

-continued

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 8
gctgagctct agagtccttt tcttttacaa agttgg 36

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 9
gcattaaagc tttgctct 18

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 10
gcctcgagca aaaattcaga cgga 24

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: synthetic
oligonucleotide

<400> SEQUENCE: 11
caaccaccgg gaggcaagct ggccagcaac tta 33

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 12
atcggctagc agatcttcaa tattggccat tagccatat 39

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 13
atcgagatct gcggccgctt acctgcccag tgcctcacga ccaa 44

<210> SEQ ID NO 14
<211> LENGTH: 54
<212> TYPE: DNA
<213> ORGANISM: Artificial Sequence -continued
<220> FEATURE:
<223> OTHER INFORMATION: Description of Artificial Sequence: primer

<400> SEQUENCE: 14
atcggcggcc gcccaccatg gaactcagcg tcctcctctt ccttgcaccc tagg 54

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 15
atcggcggcc gcacttacct gtgtgcccca ggaaagtatt tcaagaagcc ag 52

<210> SEQ ID NO 16
<211> LENGTH: 92
<212> TYPE: DNA
<213> ORGANISM: Artificial Sequence
<220> FEATURE:
<223> OTHER INFORMATION: Description of Artificial Sequence: primer

<400> SEQUENCE: 16
actgtgatca taggcaccta ttggtcttac tgacatccac tttctctcca caggcaagtt 60
tacaaaacct gcaggaaatc aatgcttaca tt 92

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 17
actgatcgat ttccctcagc cccttcagcg gggcaggaag c 41

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 18
gactacgact agtgtatgtt tagaaaaaca agg 33

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 19
ctaggctact agtactgtag gatctcgaac ag 32

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 20

-continued gggctatatg agatcttgaa taataaaatg tgt 33

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 21
ttcgatgatc accaccatgg aactcagcgt cctcctcttc cttgcac 47

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 22
ttcgagccgg ctcatcagcg gggcaggaag cggatctggt atgttg 46

<210> SEQ ID NO 23
<211> LENGTH: 82
<212> TYPE: DNA
<213> ORGANISM: Artificial Sequence
<220> FEATURE:
<223> OTHER INFORMATION: Description of Artificial Sequence: pLTR

<400> SEQUENCE: 23
cgttaacact agtaagcttg ctctaaggta aatagtcgac aggcctgcgc cagtcctccg 60
attgactgag tcgcccgggt ac 82

<210> SEQ ID NO 24
<211> LENGTH: 83
<212> TYPE: DNA
<213> ORGANISM: Artificial Sequence
<220> FEATURE:
<223> OTHER INFORMATION: Description of Artificial Sequence: pLTR

<400> SEQUENCE: 24
cccgggcgac tcagtcaatc ggaggactgg cgcaggcctg tcgactattt accttagagc 60
aagcttacta gtgttaacgg cgc 83

<210> SEQ ID NO 25
<211> LENGTH: 124
<212> TYPE: DNA
<213> ORGANISM: Artificial Sequence
<220> FEATURE:
<223> OTHER INFORMATION: Description of Artificial Sequence: pL-SA-N

<400> SEQUENCE: 25
gatctaacct aggtctcgag tgtttaaaca ctgggcttgt cgagacagag aagactcttg 60
cgtttctgat aggcacctat tggtcttact gacatccact ttgcctttct ctccacaggt 120
gagg 124

<210> SEQ ID NO 26
<211> LENGTH: 120
<212> TYPE: DNA
<213> ORGANISM: Artificial Sequence
<220> FEATURE:
<223> OTHER INFORMATION: Description of Artificial Sequence: pL-SA-N

<400> SEQUENCE: 26

-continued

```
cctcacctgt ggagagaaag gcaaagtgga tgtcagtaag accaataggt gcctatcaga     60

aacgcaagag tcttctctgt ctcgacaagc ccagtgttta aacactcgag acctaggtta    120
```

<210> SEQ ID NO 27
<211> LENGTH: 99
<212> TYPE: DNA
<213> ORGANISM: Artificial Sequence
<220> FEATURE:
<223> OTHER INFORMATION: Description of Artificial Sequence: pL-SA-N with a splice donor deletion

<400> SEQUENCE: 27

```
ttagctaact agtacagacg caggcgcata acatcaaaca tagacactag acaatcggac     60

agacacagat aagttgctgg ccagcttgcc tcccggtgg                            99
```

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: pL-SA-N with a splice donor deletion

<400> SEQUENCE: 28

```
ccctcactcg gcgcgccagt cttccga                                         27
```

<210> SEQ ID NO 29
<211> LENGTH: 79
<212> TYPE: DNA
<213> ORGANISM: Artificial Sequence
<220> FEATURE:
<223> OTHER INFORMATION: Description of Artificial Sequence: CMV/R junction of EIAV LTR plasmid

<400> SEQUENCE: 29

```
agcagagctc gtttagtgaa ccgacttaag tcttcctgca ggggctctaa ggtaaatagg     60

gcactcagat tctgcggtc                                                  79
```

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: CMV/R junction of EIAV LTR plasmid

<400> SEQUENCE: 30

```
cacacctggc cggggatcct acgatcagcc agg                                  33
```

<210> SEQ ID NO 31
<211> LENGTH: 129
<212> TYPE: DNA
<213> ORGANISM: Artificial Sequence
<220> FEATURE:
<223> OTHER INFORMATION: Description of Artificial Sequence: pEGASUS-1

<400> SEQUENCE: 31

```
tcgacgttta aacactgggc ttgtcgagac agagaagact cttgcgtttc tgataggcac     60

ctattggtct tactgacatc cactttgcct ttctctccac aggtcacgtg aagctagcct    120

cgagttggc                                                            129
```

<210> SEQ ID NO 32

-continued

```
<211> LENGTH: 128
<212> TYPE: DNA
<213> ORGANISM: Artificial Sequence
<220> FEATURE:
<223> OTHER INFORMATION: Description of Artificial Sequence: pEGASUS-1

<400> SEQUENCE: 32

tcagccaact cgaggctagc ttcacgtgac ctgtggagag aaaggcaaag tggatgtcag     60

taagaccaat aggtgcctat cagaaacgca agagtcttct ctgtctcgac aagcccagtg    120

tttaaacg                                                             128


<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: EIAV vector

<400> SEQUENCE: 33

aggaggacag gcaagatggg agaccctttg ac                                   32


<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: EIAV vector

<400> SEQUENCE: 34

ggggtcgact ctagagtcct tttc                                            24


<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: EIAV vector

<400> SEQUENCE: 35

gtcaaagggt ctcccatctt gcctgtcctc ct                                   32


<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: EIAV vector

<400> SEQUENCE: 36

ctatataagc agagctcgtt tagtg                                           25
```